(12) United States Patent
Byzova et al.

(10) Patent No.: US 8,080,252 B2
(45) Date of Patent: Dec. 20, 2011

(54) COMPOUNDS AND METHODS OF MODULATING ANGIOGENESIS

(75) Inventors: Tatiana Byzova, Pepper Pike, OH (US); Ganapati H. Maha Baleshuar, Cleveland, OH (US); Weiyi Feng, Woodmere, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 120 days.

(21) Appl. No.: 12/357,186

(22) Filed: Jan. 21, 2009

(65) Prior Publication Data
US 2009/0298769 A1 Dec. 3, 2009

Related U.S. Application Data

(63) Continuation-in-part of application No. PCT/US2007/073877, filed on Jul. 19, 2007.

(60) Provisional application No. 60/831,992, filed on Jul. 19, 2006.

(51) Int. Cl.
| | |
|---|---|
| *C07K 14/00* | (2006.01) |
| *C07K 7/00* | (2006.01) |
| *C07K 7/06* | (2006.01) |
| *C07K 7/08* | (2006.01) |
| *A61K 39/00* | (2006.01) |
| *A61K 38/08* | (2006.01) |
| *A61K 38/10* | (2006.01) |

(52) U.S. Cl. .................. 424/185.1; 514/21.3; 514/21.4; 514/21.6

(58) Field of Classification Search ........................ None
See application file for complete search history.

(56) References Cited

U.S. PATENT DOCUMENTS

| | | | | |
|---|---|---|---|---|
| 5,177,188 | A | * | 1/1993 | Ginsberg et al. ............... 530/324 |
| 6,210,913 | B1 | * | 4/2001 | Phillips et al. ................. 435/7.8 |
| 6,706,709 | B2 | | 3/2004 | Tang et al. |
| 6,958,340 | B2 | | 10/2005 | Bilodeau et al. |
| 7,422,883 | B2 | * | 9/2008 | Agrez et al. ................... 435/194 |

FOREIGN PATENT DOCUMENTS
| | | | |
|---|---|---|---|
| WO | WO 98/16241 | A1 | 4/1998 |
| WO | WO 02/051993 | A1 * | 7/2002 |

OTHER PUBLICATIONS

Borges et al, J Biol Chem 275(51): 39867-39873, 2000.*

* cited by examiner

*Primary Examiner* — Phuong Huynh
(74) *Attorney, Agent, or Firm* — Tarolli, Sundheim, Covell & Tummino LLP

(57) ABSTRACT

A method of modulating angiogenesis in a tissue comprises administering to the tissue a therapeutically effective amount of an agent that modulates complex formation of $\alpha_v\beta_3$ integrin and VEGFR2.

26 Claims, 25 Drawing Sheets

SEQUENCE LISTING

<160> NUMBER OF SEQ ID NOS: 17

<210> SEQ ID NO 1
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 1

Asp Thr Ala Asn Asn Pro Leu Tyr Lys Glu Ala Thr Ser Thr Phe Thr
1               5                   10                  15

<210> SEQ ID NO 2
<211> LENGTH: 28
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION

<400> SEQUENCE: 2

Tyr Gly Arg Lys Lys Arg Arg Gln Arg Arg Gly Asp Thr Ala Asn
1               5                   10                  15

Asn Pro Leu Tyr Lys Glu Ala Thr Ser Thr Phe Thr
            20                  25

<210> SEQ ID NO 3
<211> LENGTH: 23
<212> TYPE: PRT
<213> ORGANISM: Homo sapiens

<400> SEQUENCE: 3

Asp Thr Ala Asn Asn Pro Leu Tyr Lys Glu Ala Thr Ser Thr Phe Thr
1               5                   10                  15

Asn Ile Thr Tyr Arg Gly Thr
            20

<210> SEQ ID NO 4
<211> LENGTH: 10
<212> TYPE: PRT
<213> ORGANISM: Homo sapiens

<400> SEQUENCE: 4

Lys Glu Phe Ala Lys Phe Glu Glu Glu Arg
1               5                   10

<210> SEQ ID NO 5
<211> LENGTH: 10
<212> TYPE: PRT
<213> ORGANISM: Homo sapiens

<400> SEQUENCE: 5

Ala Arg Ala Lys Trp Asp Thr Ala Asn Asn
1               5                   10

<210> SEQ ID NO 6
<211> LENGTH: 20
<212> TYPE: PRT
<213> ORGANISM: Homo sapiens

<400> SEQUENCE: 6

```
Cys Met Glu Glu Glu Val Cys Asp Pro Lys Phe His Tyr Asp Asn
1               5                   10                  15

Thr Ala Gly Ile
            20

<210> SEQ ID NO 7
<211> LENGTH: 20
<212> TYPE: PRT
<213> ORGANISM: Homo sapiens

<400> SEQUENCE: 7

Gln Thr Ser Gly Tyr Gln Ser Gly Tyr His Ser Asp Asp Thr Asp Thr
1               5                   10                  15

Thr Val Tyr Ser
            20

<210> SEQ ID NO 8
<211> LENGTH: 20
<212> TYPE: PRT
<213> ORGANISM: Homo sapiens

<400> SEQUENCE: 8

Arg Asp Ile Tyr Lys Asp Pro Asp Tyr Val Arg Lys Gly Asp Ala Arg
1               5                   10                  15

Leu Pro Leu Lys
            20

<210> SEQ ID NO 9
<211> LENGTH: 23
<212> TYPE: PRT
<213> ORGANISM: Homo sapiens

<400> SEQUENCE: 9

Trp Met Ala Pro Glu Thr Ile Phe Asp Arg Val Tyr Thr Ile Gln Ser
1               5                   10                  15

Asp Val Trp Ser Phe Gly Val
            20

<210> SEQ ID NO 10
<211> LENGTH: 20
<212> TYPE: PRT
<213> ORGANISM: Homo sapiens

<400> SEQUENCE: 10

Leu Gly Ala Ser Pro Tyr Pro Gly Val Lys Ile Asp Glu Glu Phe Cys
1               5                   10                  15

Arg Arg Leu Lys
            20

<210> SEQ ID NO 11
<211> LENGTH: 20
<212> TYPE: PRT
<213> ORGANISM: Homo sapiens

<400> SEQUENCE: 11

Glu Gly Thr Arg Met Arg Ala Pro Asp Tyr Thr Thr Pro Glu Met Tyr
1               5                   10                  15

Gln Thr Met Leu
            20

<210> SEQ ID NO 12
<211> LENGTH: 30
```

```
<212> TYPE: PRT
<213> ORGANISM: Homo sapiens

<400> SEQUENCE: 12

Gly Asn Leu Leu Gln Ala Asn Ala Gln Gln Asp Gly Lys Asp Tyr Ile
1               5                   10                  15

Val Leu Pro Ile Ser Glu Thr Leu Ser Met Glu Glu Asp Ser
            20                  25                  30

<210> SEQ ID NO 13
<211> LENGTH: 27
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: PHOSPHORYLATION

<400> SEQUENCE: 13

Tyr Gly Arg Lys Lys Arg Arg Gln Arg Arg Gly Lys Glu Ala Thr
1               5                   10                  15

Ser Thr Phe Thr Asn Ile Thr Tyr Arg Gly Thr
            20                  25

<210> SEQ ID NO 14
<211> LENGTH: 28
<212> TYPE: PRT
<213> ORGANISM: Homo sapiens

<400> SEQUENCE: 14

Tyr Gly Arg Lys Lys Arg Arg Gln Arg Arg Gly Asp Thr Ala Asn
1               5                   10                  15

Asn Pro Leu Phe Lys Glu Ala Thr Ser Thr Phe Thr
            20                  25

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION

<400> SEQUENCE: 15

Lys Glu Ala Thr Ser Thr Phe Thr Asn Ile Thr Tyr Arg Gly Thr
1               5                   10                  15

<210> SEQ ID NO 16
<211> LENGTH: 16
<212> TYPE: PRT
<213> ORGANISM: Homo sapiens

<400> SEQUENCE: 16

Asp Thr Ala Asn Asn Pro Leu Phe Lys Glu Ala Thr Ser Thr Phe Thr
1               5                   10                  15

<210> SEQ ID NO 17
<211> LENGTH: 15
<212> TYPE: PRT
<213> ORGANISM: Homo sapiens

<400> SEQUENCE: 17

Lys Glu Ala Thr Ser Thr Phe Thr Asn Ile Thr Phe Arg Gly Thr
1               5                   10                  15
```

COMPOUNDS AND METHODS OF MODULATING ANGIOGENESIS

RELATED APPLICATION

This application is a Continuation-in-Part of International Application No. PCT/US2007/073877, filed Jul. 19, 2007 and claims priority from U.S. Provisional Application No. 60/831,992 filed Jul. 19, 2006, both of which are incorporated herein by reference in their entirety.

GOVERNMENT FUNDING

This invention was made with government support under Grant No. NIH Grant PPG HL073311 awarded by National Institute of Health. The government has certain rights in the invention.

FIELD OF THE INVENTION

The present invention relates to compounds and methods of modulating angiogenesis and particularly relates to compounds and methods of modulating tumor growth and angiogenesis.

BACKGROUND

The process of angiogenesis involves coordinated endothelial cell (EC) proliferation, invasion, migration, and tube formation. This process is known to be induced by vascular growth factors and its receptors in coordination with extracellular matrix interacting molecules such as integrins. Integrins are heterodimeric transmembrane receptors, which play central roles in cell adhesion, migration, proliferation, differentiation and programmed cell death. $\alpha_v\beta_3$ integrin is a major integrin expressed on proliferating endothelial cells during angiogenesis and vascular remodeling. The disruption of $\alpha_v\beta_3$ integrin ligation either by blocking antibody (LM609 or Vitaxin) or by cyclic peptide antagonists (RGD) prevents blood vessel formation in mouse retina, rabbit cornea, chick chorioallantoic membrane, and human skin transplanted onto athymic mice. More importantly, function-blocking anti-$\beta_3$ antibody that recognizes at least three integrins ($\alpha_{IIb}\beta_3$, $\alpha_v\beta_3$ and $\alpha_M\beta_2$) has been shown to be beneficial in high risk angioplasty patients in part due to the blockade of $\alpha_v\beta_3$. In the studies on the role of $\alpha_v\beta_3$ in tumor vasculature and survival, histological examination of the tumor tissue treated with the $\alpha_v\beta_3$ blockers revealed reduction not only in the tumor cell viability but also in the vascular density.

Mice lacking $\alpha_v$ integrin showed relatively normal blood vessel development $\alpha_v$ integrin knockout mice died at early stages of development due to extensive vasculature). Furthermore, studies using $\beta_3$ and $\beta_5$ null mice demonstrated an enhanced tumor growth, tumor angiogenesis and VEGF-A-induced vascular permeability due to the elevated levels of VEGFR-2 on EC. Therefore, it has been concluded that $\alpha_v\beta_3$ and $\alpha_v\beta_5$ integrin function as the negative regulators of angiogenesis by restricting the VEGF receptor-2 expression.

SUMMARY OF THE INVENTION

The present invention relates to a method of modulating angiogenesis in a cell population. The method includes contacting a cell population that comprises cells expressing $\alpha_v\beta_3$ integrin and VEGFR2 with a therapeutically effective amount of an agent that stimulates or inhibits complexing of $\alpha_v\beta_3$ integrin and VEGFR2. In the method, the agent does not substantially inhibit natural or native ligand (e.g., vitronectin) binding to the $\alpha_v\beta_3$ integrin.

In an aspect of the invention, the agent can inhibit tyrosine phosphorylation of the $\alpha_v\beta_3$ integrin and/or tyrosine phosphorylation of VEGFR2 upon VEGF stimulation. The agent can also compete with $\alpha_v\beta_3$ integrin for interaction with VEGFR2.

In another aspect of the invention, the agent can inhibit tyrosine phosphorylation of a tyrosine of the $\beta_3$ subunit of the $\alpha_v\beta_3$ integrin. In a particular aspect, the agent can inhibit tyrosine phosphorylation of a tyrosine of the cytoplasmic tail of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In yet another aspect of the invention, the agent can comprise a peptide having a peptide sequence of about 5 to about 50 amino acids in length. The peptide can have a sequence that corresponds to a portion of the peptide sequence of at least one of $\alpha_v\beta_3$ integrin or VEGFR2. The portion of the peptide sequence of at least one of $\alpha_v\beta_3$ integrin or VEGFR2 can contain a tyrosine residue, which is capable of being phosphorylated upon complex formation of the $\alpha_v\beta_3$ integrin and VEGFR2.

In a further aspect, the agent can comprise a peptide that has a sequence that corresponds to a portion of the peptide sequence of the cytoplasmic domain of the $\beta_3$ subunit of the $\alpha_v\beta_3$ integrin. The portion of the peptide sequence of the cytoplasmic domain of the $\beta_3$ subunit of the $\alpha_v\beta_3$ integrin can contain a tyrosine residue (e.g., tyrosine-747), which is capable of being phosphorylated upon complex formation of the $\alpha_v\beta_3$ integrin and VEGFR2.

In another aspect of the invention, the peptide can comprise, for example, a sequence selected from the group consisting of: SEQ ID NO:1, SEQ ID NO:2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

In another aspect, the agent can comprise a c-SRC kinase inhibitor that inhibits tyrosine phosphorylation of $\alpha_v\beta_3$ integrin. The c-SRC kinase inhibitor can include a 3-(4,5,6,7-tetrahydroinol-2-ylmethylidene)-2-indolinone derivative. Examples of a 3-(4,5,6,7-tetrahydroinol-2-ylmethylidene)-2-indolinone derivatives include 2-oxo-3(4,5,6,7-tetrahydro-1-H-indol-2-ylmethylene)-2,3-dihydro-1H-indole-5-sulfonic acid dimethylamide and 2-oxo-3(4,5,6,7-tetrahydro-1-H-indol-2-ylmethylene)-2,3-dihydro-1H-indole-5-sulfonic acid amide.

In a further aspect, the agent can comprise an antisense oligonucleotide, interfering nucleotide, or antibody that inhibits expression or activity of SRC-kinase.

The present invention also relates to a method of inhibiting angiogenesis in a tissue. The method comprises administering to the tissue a therapeutically effective amount of an agent that inhibits complex formation of $\alpha_v\beta_3$ integrin and VEGFR2. The agent does not inhibit natural ligand binding to the $\alpha_v\beta_3$ integrin.

In an aspect of the invention, the agent can inhibit complexing of the cytoplasmic regions of $\alpha_v\beta_3$ integrin and VEGFR2.

In another aspect of the invention, the agent can inhibit tyrosine phosphorylation of the $\alpha_v\beta_3$ integrin and/or tyrosine phosphorylation of VEGFR2 upon VEGF stimulation. The agent can also compete with $\alpha_v\beta_3$ integrin for interaction with VEGFR2.

In still another aspect of the invention, the agent can inhibit tyrosine phosphorylation of a tyrosine of the $\beta_3$ subunit of the $\alpha_v\beta_3$ integrin. In a particular aspect, the agent can inhibit tyrosine phosphorylation of a tyrosine of the cytoplasmic tail of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In yet another aspect of the invention, the agent can comprise a peptide having a peptide sequence of about 5 to about 50 amino acids in length. The peptide can have a sequence that corresponds to a cytoplasmic portion of the peptide sequence of at least one of $\alpha_v\beta_3$ integrin or VEGFR2. The portion of the peptide sequence of at least one of $\alpha_v\beta_3$ integrin or VEGFR2 can contain a tyrosine residue, which is capable of being phosphorylated upon complex formation of the $\alpha_v\beta_3$ integrin and VEGFR2.

In a further aspect, the agent can comprise a peptide that has a sequence that corresponds to a portion of the peptide sequence of the cytoplasmic domain of the $\beta_3$ subunit of the $\alpha_v\beta_3$ integrin. The portion of the peptide sequence of the cytoplasmic domain of the $\beta_3$ subunit of the $\alpha_v\beta_3$ integrin can contain a tyrosine residue (e.g., tyrosine-747), which is capable of being phosphorylated upon complex formation of the $\alpha_v\beta_3$ integrin and VEGFR2.

In another aspect of the invention, the peptide can comprise, for example, a sequence selected from the group consisting of: SEQ ID NO:1, SEQ ID NO:2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

In another aspect, the agent can comprise a c-SRC kinase inhibitor that inhibits tyrosine phosphorylation of $\alpha_v\beta_3$ integrin. The c-SRC kinase inhibitor can include a 3-(4,5,6,7-tetrahydroinol-2-ylmethylidene)-2-indolinone derivative. Examples of a 3-(4,5,6,7-tetrahydroinol-2-ylmethylidene)-2-indolinone derivatives include 2-oxo-3(4,5,6,7-tetrahydro-1-H-indol-2-ylmethylene)-2,3-dihydro-1H-indole-5-sulfonic acid dimethylamide and 2-oxo-3(4,5,6,7-tetrahydro-1-H-indol-2-ylmethylene)-2,3-dihydro-1H-indole-5-sulfonic acid amide.

In a further aspect, the agent can comprise an antisense oligonucleotide, interfering nucleotide, or antibody that inhibits expression or activity of SRC-kinase.

The present invention also relates to a method of treating an angiogenic disorder in a subject. The angiogenic disorder can include, for example, aberrant tumor growth and age-related macular degeneration. The method includes administering to cells expressing $\alpha_v\beta_3$ integrin and VEGFR2 of the subject a therapeutically effective amount of agent that inhibits complexing of the expressed $\alpha_v\beta_3$ integrin and VEGFR2. In the method, the agent does not inhibit natural ligand binding to the $\alpha_v\beta_3$ integrin.

In an aspect of the invention, the agent can inhibit tyrosine phosphorylation of the $\alpha_v\beta_3$ integrin and/or tyrosine phosphorylation of VEGFR2 upon VEGF stimulation. The agent can also compete with $\alpha_v\beta_3$ integrin for interaction with VEGFR2.

In another aspect of the invention, the agent can inhibit tyrosine phosphorylation of a tyrosine of the $\beta_3$ subunit of the $\alpha_v\beta_3$ integrin. In a particular aspect, the agent can inhibit tyrosine phosphorylation of a tyrosine of the cytoplasmic tail of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In yet another aspect of the invention, the agent can comprise a peptide having a peptide sequence of about 5 to about 50 amino acids in length. The peptide can have a sequence that corresponds to a portion of the peptide sequence of at least one of $\alpha_v\beta_3$ integrin or VEGFR2. The portion of the peptide sequence of at least one of $\alpha_v\beta_3$ integrin or VEGFR2 can contain a tyrosine residue, which is capable of being phosphorylated upon complex formation of the $\alpha_v\beta_3$ integrin and VEGFR2.

In a further aspect, the agent can comprise a peptide that has a sequence that corresponds to a portion of the peptide sequence of the cytoplasmic domain of the $\beta_3$ subunit of the $\alpha_v\beta_3$ integrin. The portion of the peptide sequence of the cytoplasmic domain of the $\beta_3$ subunit of the $\alpha_v\beta_3$ integrin can contain a tyrosine residue (e.g., tyrosine-747), which is capable of being phosphorylated upon complex formation of the $\alpha_v\beta_3$ integrin and VEGFR2.

In another aspect of the invention, the peptide can comprise, for example, a sequence selected from the group consisting of: SEQ ID NO:1, SEQ ID NO:2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO:11, and SEQ ID NO: 12.

In another aspect, the agent can comprise a c-SRC kinase inhibitor that inhibits tyrosine phosphorylation of $\alpha_v\beta_3$ integrin. The c-SRC kinase inhibitor can include a 3-(4,5,6,7-tetrahydroinol-2-ylmethylidene)-2-indolinone derivative. Examples of a 3-(4,5,6,7-tetrahydroinol-2-ylmethylidene)-2-indolinone derivatives include 2-oxo-3(4,5,6,7-tetrahydro-1-H-indol-2-ylmethylene)-2,3-dihydro-1H-indole-5-sulfonic acid dimethylamide and 2-oxo-3(4,5,6,7-tetrahydro-1-H-indol-2-ylmethylene)-2,3-dihydro-1H-indole-5-sulfonic acid amide.

In a further aspect, the agent can comprise an antisense oligonucleotide, interfering nucleotide, or antibody that inhibits expression or activity of SRC-kinase.

The present invention further relates to a pharmaceutical composition that includes a synthetic peptide that modulates complex formation of $\alpha_v\beta_3$ integrin and VEGFR2 in tumor cells. The synthetic peptide can have a sequence that corresponds to a portion of the peptide sequence of at least one of $\alpha_v\beta_3$ integrin or VEGFR2. The portion of the peptide sequence of at least one of $\alpha_v\beta_3$ integrin or VEGFR2 can contain a tyrosine residue, which is capable of being phosphorylated upon complex formation of the $\alpha_v\beta_3$ integrin and VEGFR2. The synthetic peptide can include a sequence selected from the group consisting of SEQ ID NO:1, SEQ ID NO:2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

Densitometry analysis was performed using KODAK 1D image analysis software and fold changes over control are shown.

Figure 2:
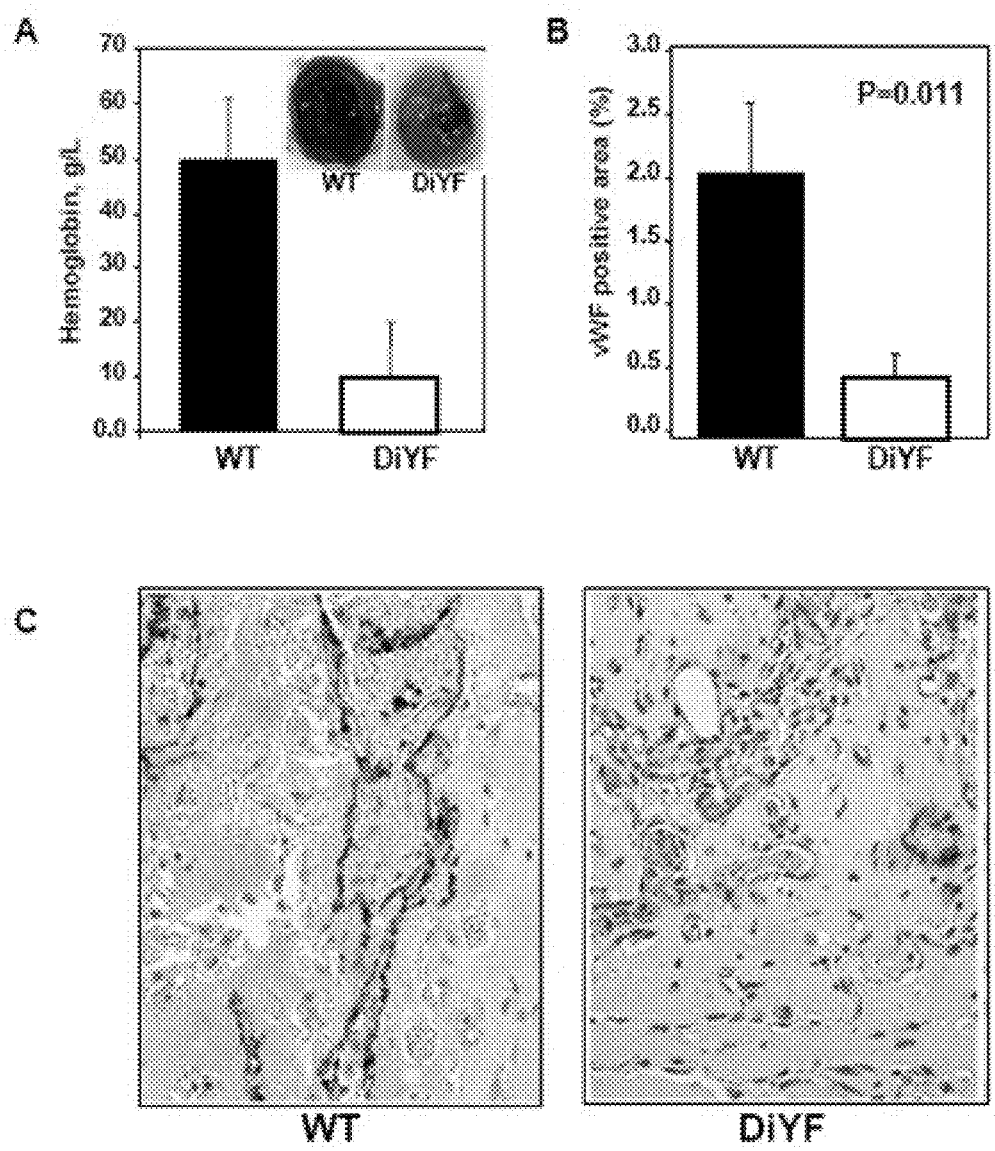

FIG. 2 illustrates $\beta_3$ integrin cytoplasmic tyrosine motif is critical for endothelial cell adhesion, spreading and migration. (A-B) Adhesion and spreading of WT and DiYF endothelial cells on various integrin ligands. Plates were coated with 10 μg/ml vitronectin (VN), fibronectin (FN), laminin-1 (LM-1), collagen (COLL) or bovine serum albumin (BSA) over night at 4° C. Wild type and DiYF mouse lung EC were harvested and re-suspended in serum free media at 5×10$^5$ cells/ml. 100 μl cell suspension was plated on each well coated with integrin ligands. After incubation at 37° C. for 45 min wells were gently washed three times with DMEM and photographs were taken. The numbers of attached and spread cells per field were counted. Adhesion and spreading of WT EC on vitronectin was assigned a value of 100%. (P values were 0.000017 and 0.00003 for cell adhesion and spreading, respectively.) (C). Migration of WT and DiYF endothelial cells on various integrin ligands. Tissue culture inserts were coated with various integrin ligands. WT and DiYF mouse lung EC were trypsinized and seeded into the top chamber. Cells were allowed to migrate, fixed and stained with crystal violet. The non-migrated cells adhered to the top surface were removed and three random fields were photographed using Leica inverted phase contrast microscope. Number of cells migrated onto vitronectin-coated insert was assigned 100% (P=0.00004). (D) VEGF-induced migration of WT and DiYF mouse lung EC. Migration assay was performed as described above using vitronectin as a substrate. The lower chamber contained 0-20 ng/ml of VEGFA165. Cells were allowed to migrate, fixed, stained and photographed. Number of WT EC migrated in the absence of VEGF was referred as 100%. (E-F) Reduced migration of DiYF endothelial cells on $\beta_3$ integrin ligand. Wild type and DiYF EC were serum starved and wounded across the cell monolayer by scraping away a swath of cells. Wells were rinsed twice with sterile PBS and further cultured in DMEM medium containing 2% FBS. After wounding sites were photographed immediately (time zero) and 12 h later using phase contrast microscope (Leica) (P=0.00004). The data represents the results of three independent experiments. Images were acquired using a Leica DMIRB phase contrast microscope, objective 5×, and a Micromax RTE/CCD-1300-V-HS camera.

Figure 3:
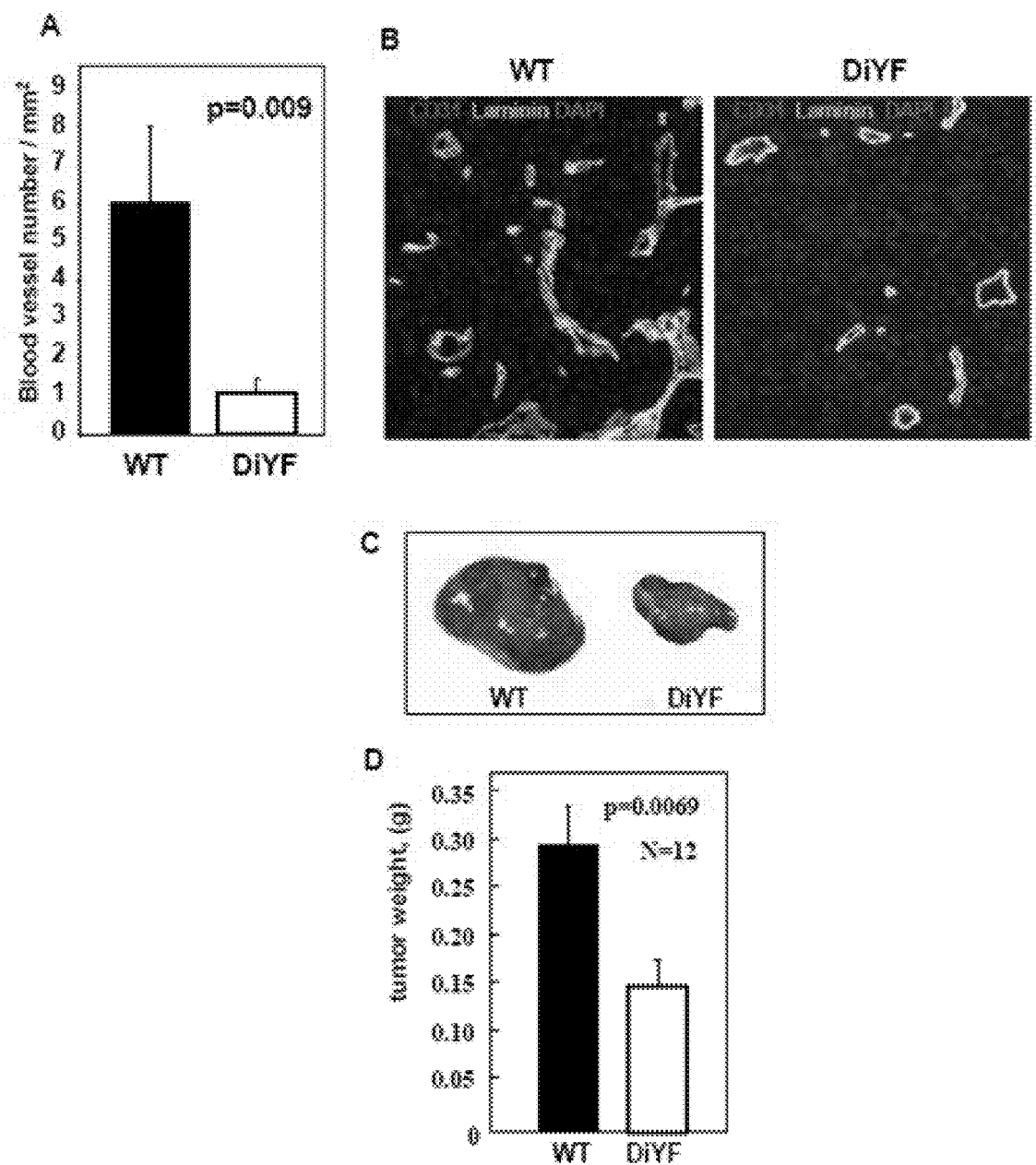

FIG. 3 illustrates $\beta_3$ integrin tyrosine 747 and 759 mutations impair angiogenic properties of EC. (A-B) Functional $\beta_3$ integrin is essential for endothelial cell organization into precapillary cords. WT and DiYF mouse lung endothelial cells were collected and re-suspended in DMEM containing 10% FCS. Equal numbers of cells were seeded on Matrigel coated plates and cells were allowed to adhere. After 24 h cells were overlaid with Matrigel with or without 40 ng/ml VEGF and maintained in culture for 6-8 days. Three random fields were photographed periodically using phase contrast microscope (Leica) (panel A). Results of quantification of cords numbers per field are presented (panel B) (P=0.0004). (C-D) $\beta_3$ integrin cytoplasmic tyrosine residues are critical for capillary tube formation. Single cell suspension of WT and DiYF mouse lung EC were transferred on Matrigel coated plates and further incubated at 37° C. for 8 h with or without 20 ng/ml VEGF. Endothelial capillary tubes formed in Matrigel were observed using an inverted phase contrast microscope (Leica) and photographs were taken. The length of tubes in random fields from each well was analyzed using ImagePro software and shown in panel D. The data represents the results of three independent experiments. Images were acquired using a Leica DMIRB phase contrast microscope, objective 5×, and a Micromax RTE/CCD-1300-V-HS camera.

Figure 4:
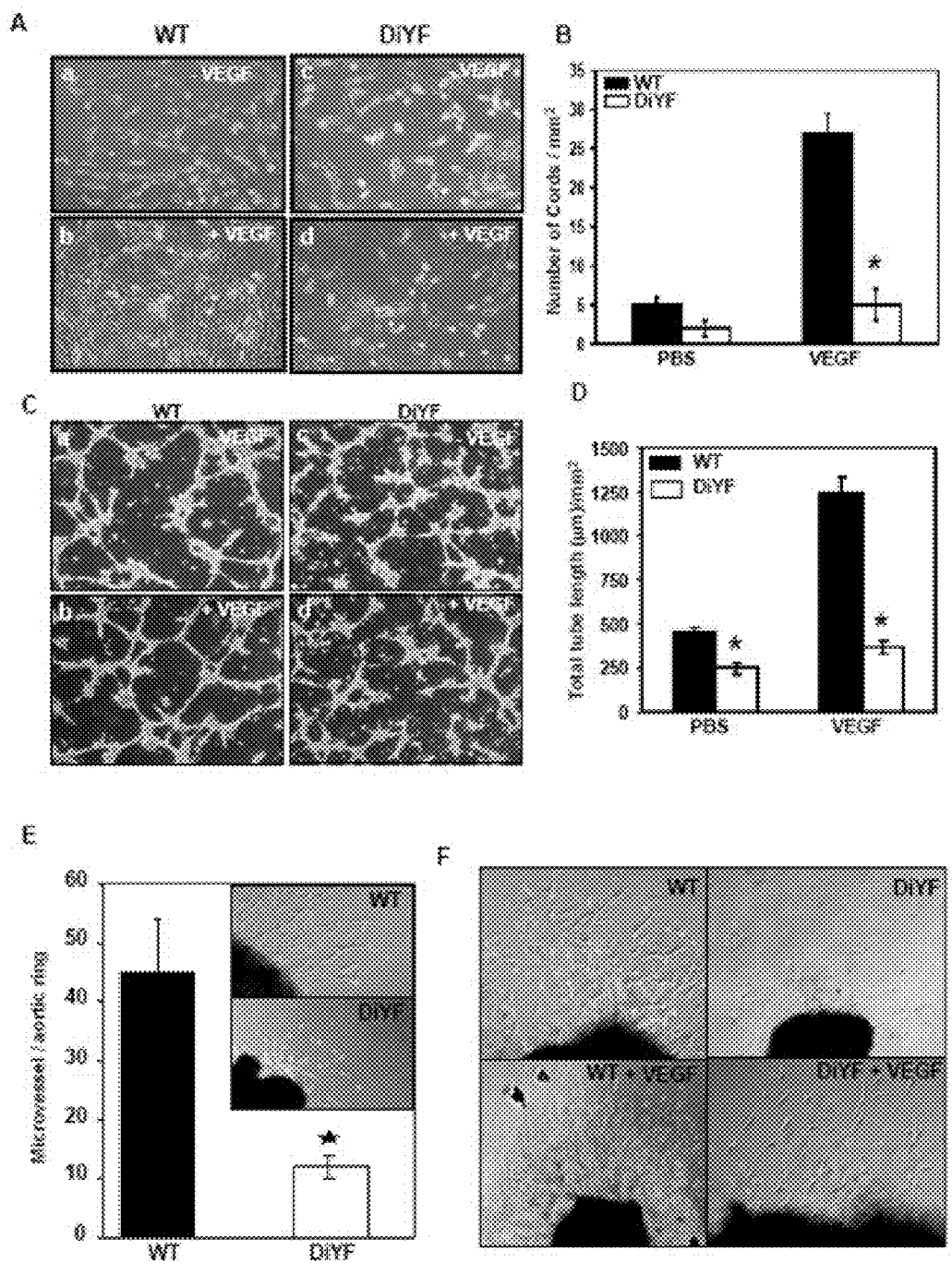
Figure 4:
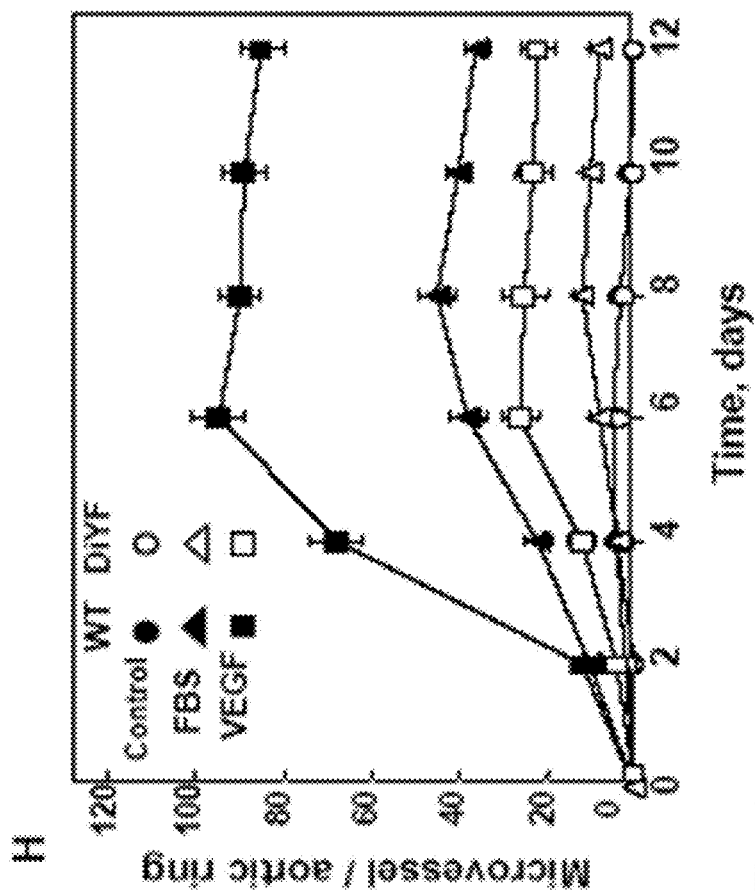
Figure 4:
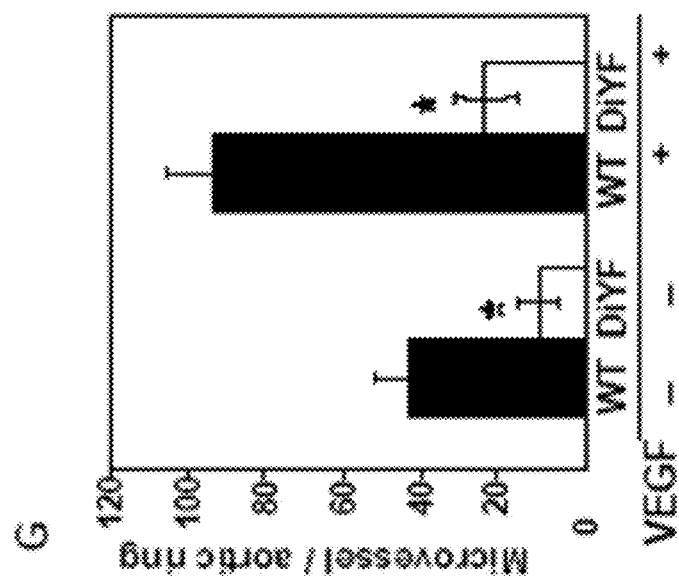

FIG. 4 illustrates $\beta_3$ integrin cytoplasmic tyrosine mutations result in impaired capillary growth ex vivo. (A-B) $\beta_3$ integrin cytoplasmic tyrosine motif is required for normal microvessel growth. Wild type (upper panel) and DiYF (lower panel) mouse aortic rings were embedded in Matrigel and maintained at 37° C. for six days. Microvessels outgrowths from aortic rings were observed periodically and photographed using Leica DMIRB phase contrast microscope. Numbers of microvessel sprouts from aortic rings were counted and represented as bar diagram (panel B). (C-D) Defective $\beta_3$ integrin tyrosine phosphorylation reduces VEGF-induced microvessel outgrowth. Wild type and DiYF mouse aortic rings were implanted in Matrigel with or without 40 ng/ml VEGF and maintained under aseptic condition for six days. Microvessel growths from implants were observed periodically and microphotographed. Representative images were shown in panel C. Numbers of microvessel outgrowth from aortic implants were counted and shown in panel D). (E-G) In ex vivo aortic ring assay using WT and DiYF aortic rings was performed in the presence of DMEM without any supplements (panel E), with endothelial growth supplement (panel F), or with 40 ng/ml VEGF together with endothelial growth supplement (panel G). Aortic rings were observed every two days, numbers of sprouts from each implant were counted and photographs were taken. Growth kinetics of wild type and DiYF aortic rings under various conditions were analyzed and represented as growth curves. The data represents the results of three independent experiments performed in triplicates. Images were acquired using a Leica DMIRB phase contrast microscope, objective 5×, and a Micromax RTE/CCD-1300-V-HS camera.

Figure 5:
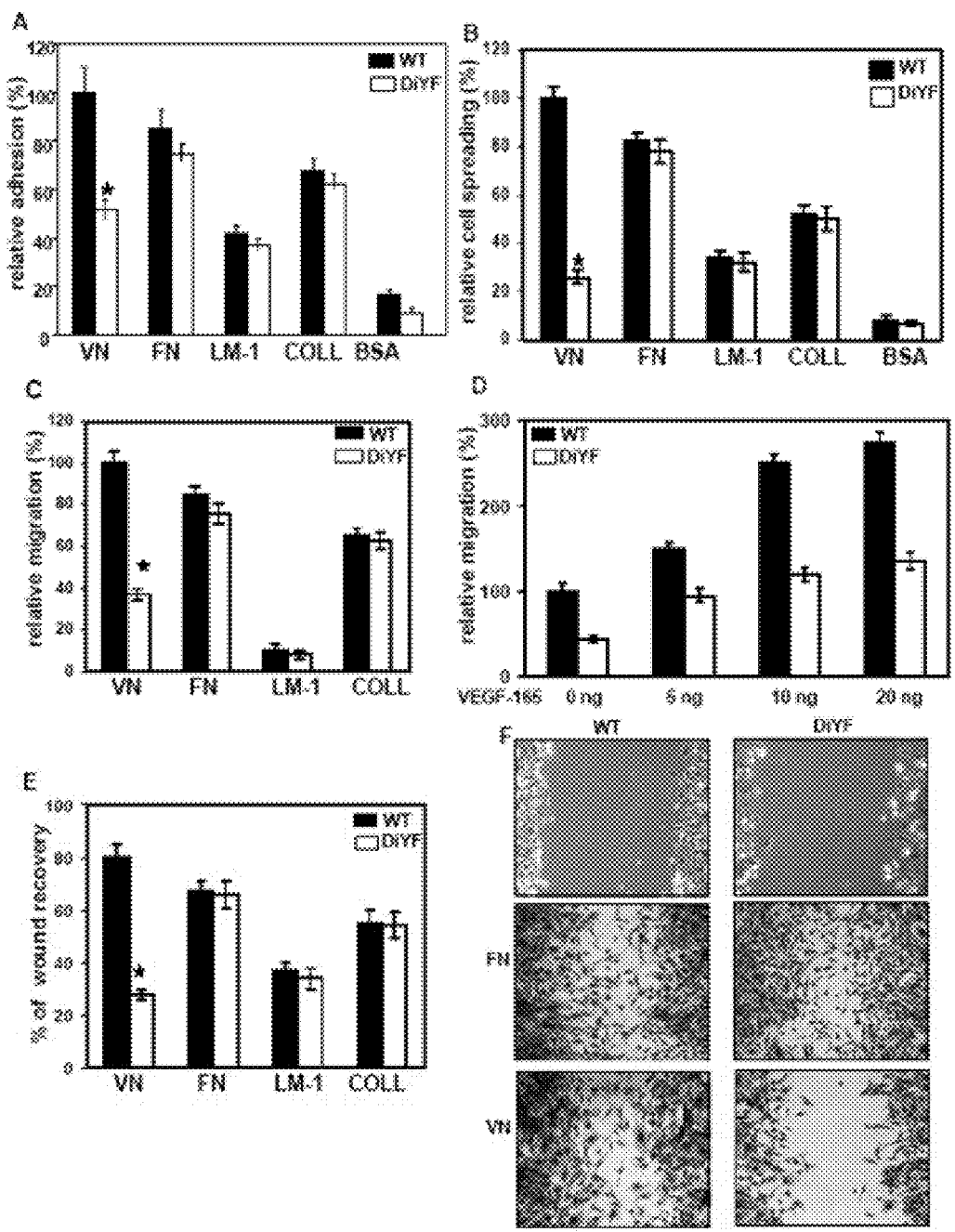

FIG. 5 illustrates $\beta_3$ integrin phosphorylation controls integrin activation. (A-B) DiYF EC exhibit reduced fibrinogen binding in response to growth factors. Wild type and DiYF mouse lung EC were serum starved for 4 h and washed twice with 1×PBS. These cells were incubated with FITC-fibrinogen in the presence or absence of 20 ng/ml VEGF for 45 min at 37° C. Cells were fixed with 0.4% formaldehyde, washed and analyzed by flow cytometry. Bars represent mean fluorescence intensity of three independent experiments performed in triplicates (panel A). Wild type and DiYF mouse lung endothelial cells were stimulated with 1 mM MnCl$_2$. MnCl$_2$ induced fibrinogen binding was diminished by 10 fold excess of unlabelled fibrinogen showing specificity of binding (panel B). *Indicates significant difference between WT and DiYF EC (P<0.05). (C-D) $\beta_3$ integrin cytoplasmic tyrosine motif is essential for interaction with monovalent ligand WOW-1 Fab. Wild type and DiYF mouse lung endothelial cells were serum starved for 4 h, washed twice with PBS and incubated with WOW-1 Fab in the presence or absence of 20 ng/ml VEGF for 45 min at 37° C. Cells were washed and incubated with FITC-conjugated goat anti-mouse IgG for 30 min at room temperature. Cells were fixed with 0.4% formaldehyde, washed and analyzed by flow cytometry. Bars represent mean fluorescence intensity of three independent experiments performed in triplicates (panel C). Wild type and DiYF mouse lung endothelial cells were also induced with 1 mM MnCl$_2$ as positive control (panel B). *Indicates significant difference between wild type and DiYF endothelial cells (P<0.05).

Figure 6:
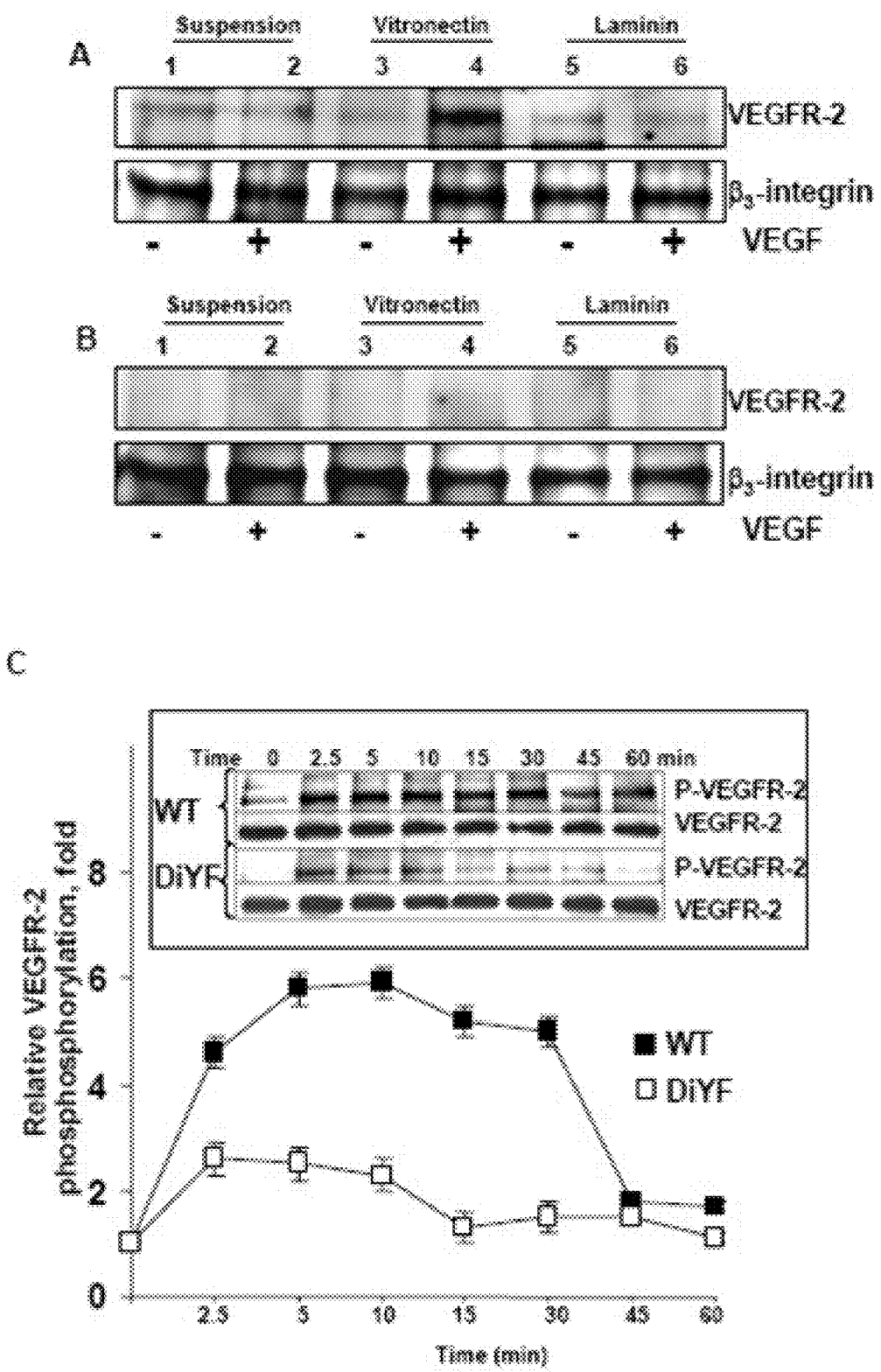
Figure 6:
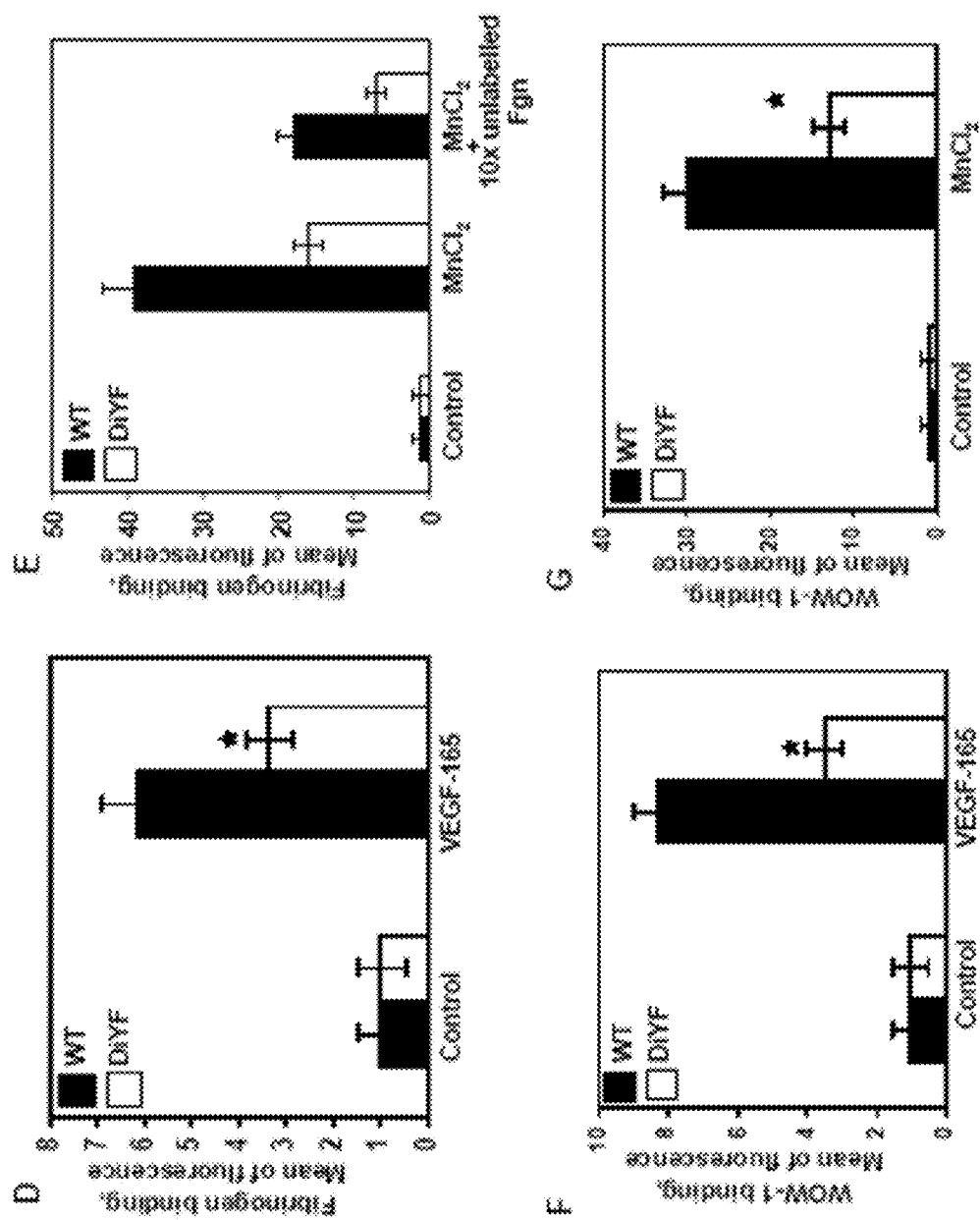

FIG. 6 illustrates $\beta_3$ integrin cytoplasmic tyrosine residues are required for VEGF induced VEGF receptor and $\beta_3$ integrin interaction. Wild type (C) and DiYF (D) mouse lung endothelial cells were either kept in suspension (lanes 1 and 2) or plated on vitronectin coated (lanes 3 and 4) or laminin coated (lanes 5 and 6) plates. These cells were treated with 20 ng/ml VEGF for 15 min (lanes 2, 4 and 6), cells were lysed, immunoprecipitated with rabbit-anti mouse $\beta_3$ integrin antibody and analyzed Western blot using rabbit-anti mouse VEGF receptor antibody. The same blots were reprobed with rabbit-anti mouse $\beta_3$ integrin antibody to conform equal loading (middle panel of C and D). IgG bands also conform equal amount of antibody have been used for immunoprecipitation (Lower panel of C and D).

Figure 7:
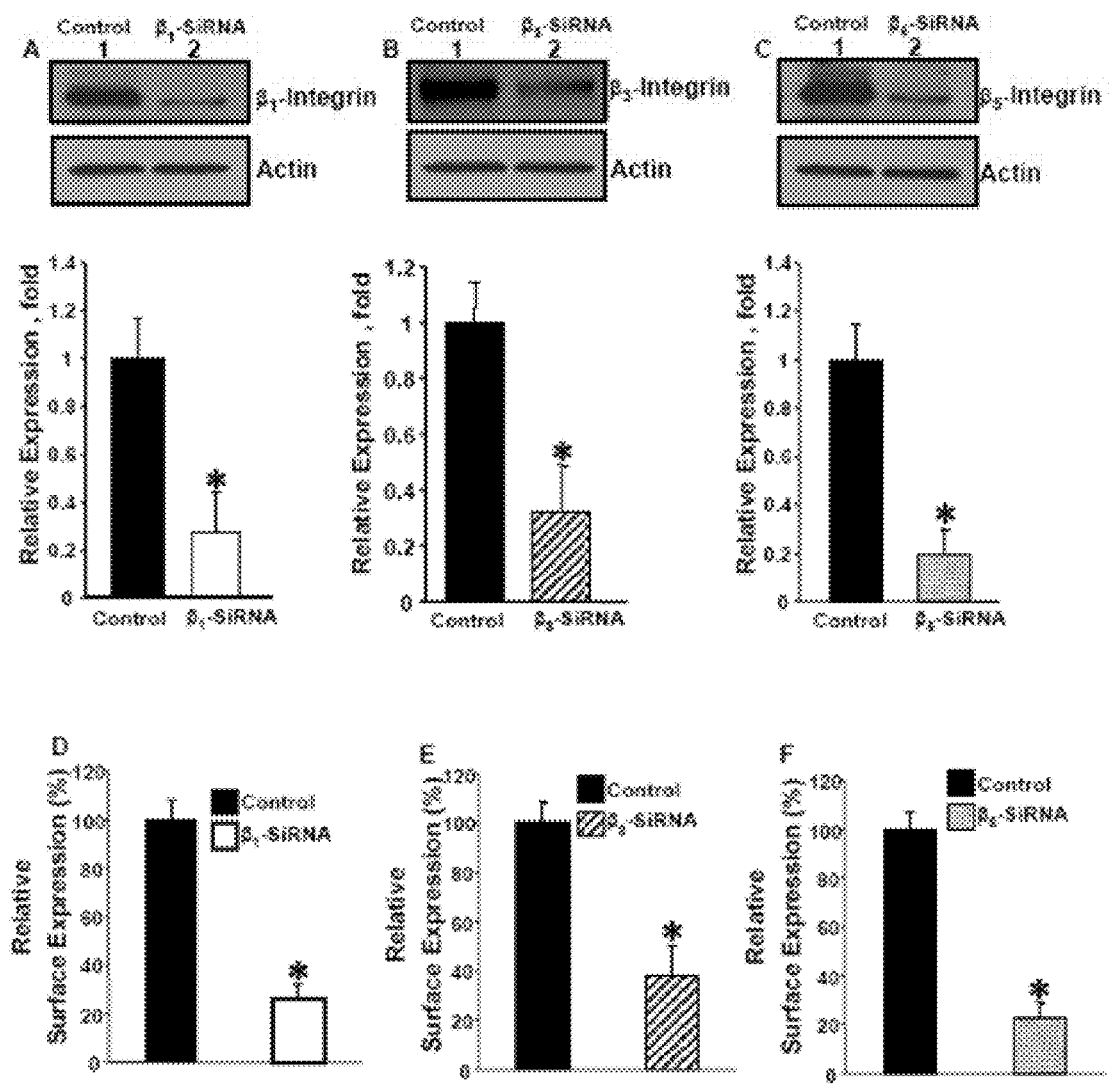

FIG. 7 illustrates knockdowns of beta subunits of integrins on endothelial cells by specific siRNAs. A-C, HUVECs were transfected with control siRNA or integrin specific siRNA and cell lysates were analyzed for expression of $\beta1$ (A), $\beta3$ (B), or $\beta5$ (C) integrin subunits using specific antibody. Densitometry analysis was performed and results are shown in bar graphs (lower panel). D-E, Cell surface expression of $\beta1$ (D), $\beta3$ (E), or $\beta5$ (F) integrin subunits in endothelial cells was assessed by FACS analysis. Cells were fixed with 3% paraformaldehyde, stained with primary antibody against corresponding integrin and with secondary antibody labeled with Alexa 488. Mean of fluorescence intensity was measured; the value obtained using control cells was assigned 100%. Asterisks indicate significant difference over control ($P<0.0038$).

Figure 8:
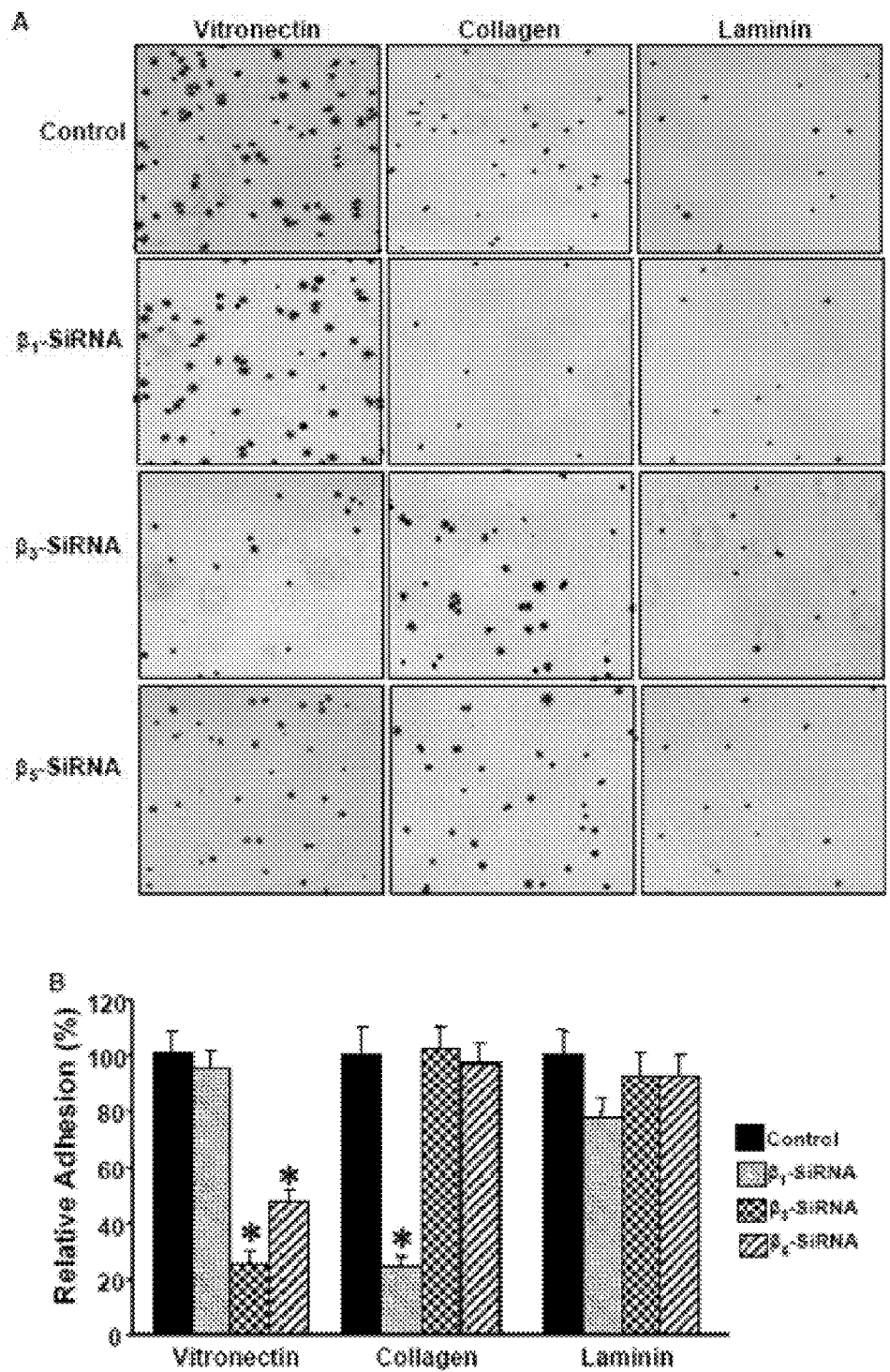

FIG. 8 illustrates specificity of integrins in reorganization on distinct ECM ligands. (A-B) HUVECs were transfected with control siRNA or siRNA specific for $\beta1$, $\beta3$, or $\beta5$ integrin. Wells of the microtiter plates were coated with vitronectin, collagen, or laminin-1 and were incubated overnight at 4° C. siRNA-transfected EC were harvested and resuspended in serum-free media at $5 \times 10^5$ cells/mL. The cell suspension (100 µL) was plated on a microtiter well coated with integrin ligand. After incubation at 37° C. for 45 min, wells were gently washed three times with DMEM and photographs were taken (panel A). The numbers of attached cells per field were counted and untransfected cells adhered on the individual ECM ligand were assigned a value of 100% (panel B). Asterisks indicate significant difference over control ($P<0.0046$).

Figure 9:
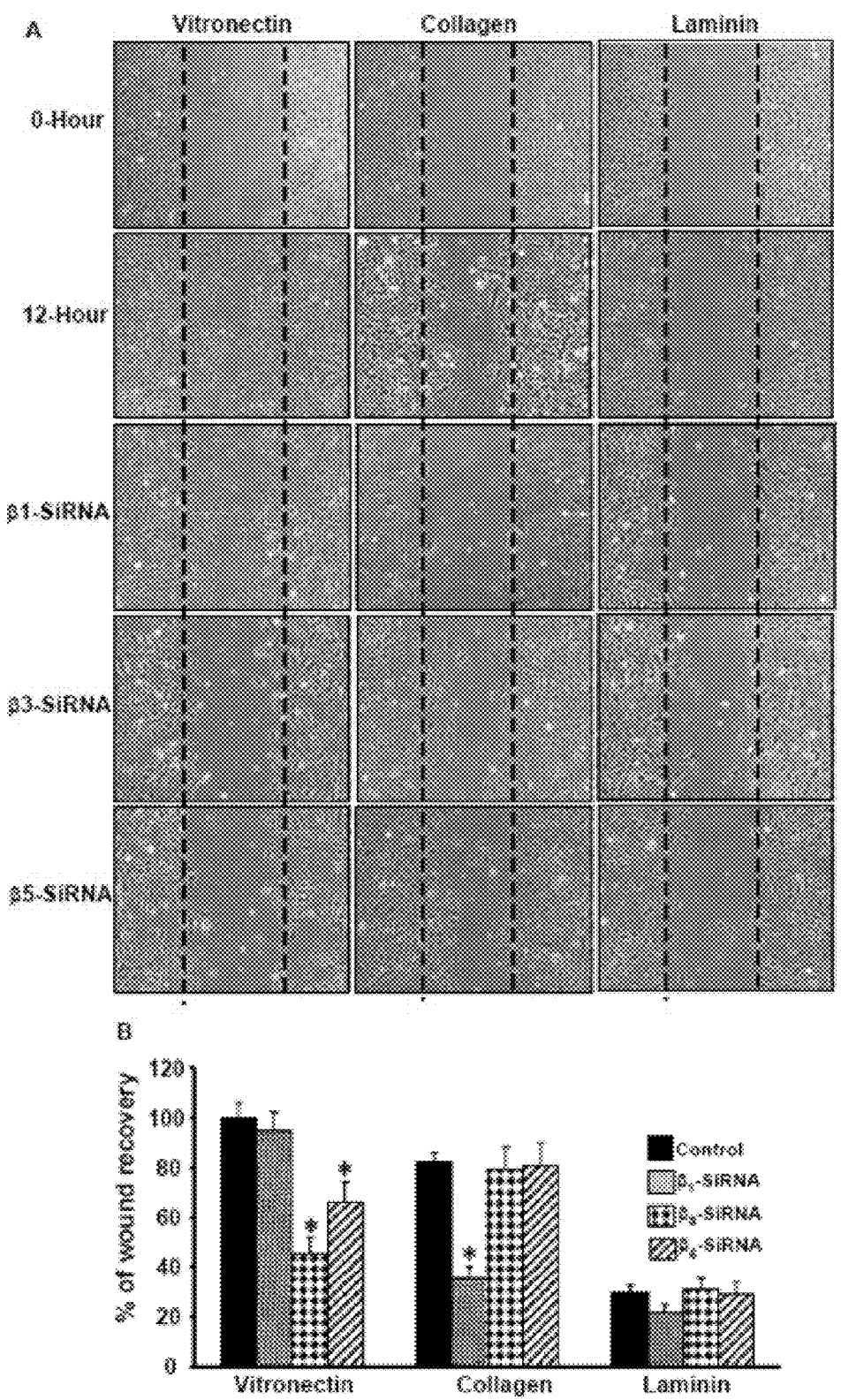

FIG. 9 illustrates Vitronectin ($\alpha_v\beta_3$) and collagen ($\alpha5\beta1$) receptors regulate endothelial cell migration. (A-B) HUVECs were transfected with control siRNA or siRNA specific for $\beta1$, $\beta3$, or $\beta5$ integrin. These cells were grown to confluence on 12-well plates precoated with individual integrin ligand. Cells were serum starved and wounded across the cell monolayer by scraping away a swath of cells. Wells were rinsed twice with sterile PBS and further cultured in DMEM medium containing 2% FBS. Sites were photographed immediately after wounding (zero hour) and 12 h later using a phase contrast microscope (panel A). Images were acquired using a Leica DMIRB phase contrast microscope, objective 5×, and a Micromax RTE/CCD-1300-V-HS camera. The mean wound area recovery by nontransfected endothelial cells on vitronectin for 12 hours was designated as 100% and relative % of wound recovery for siRNA-transfected EC were determined (panel B). Asterisks indicate significant difference over control ($P<0.0058$).

Figure 10:
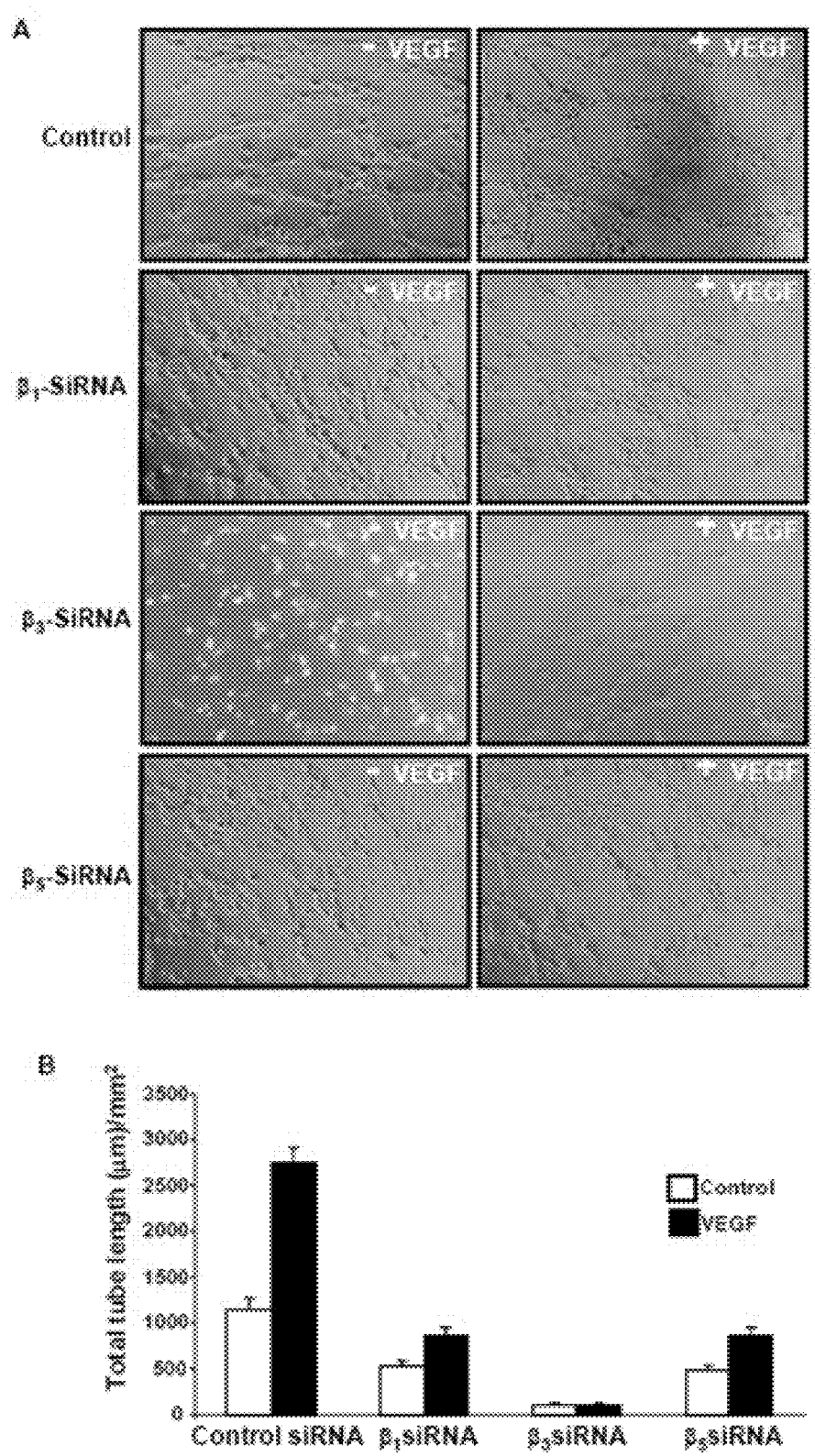

FIG. 10 illustrates $\beta3$ integrin regulates endothelial cell morphogenesis in vitro. (A-B) HUVECs were transfected with control siRNA or siRNA specific for $\beta1$, $\beta3$, or $\beta5$ integrin. Cells were transferred to Matrigel coated plates and further incubated at 37° C. for 8 h with or without 20 ng/mL VEGF. Endothelial capillary tubes formed in Matrigel were observed using an inverted phase contrast microscope and photographs were taken (panel A). Mean length of tubes from five random fields were measured using ImagePro software (panel B). Asterisks indicate significant difference over control.

Figure 11:
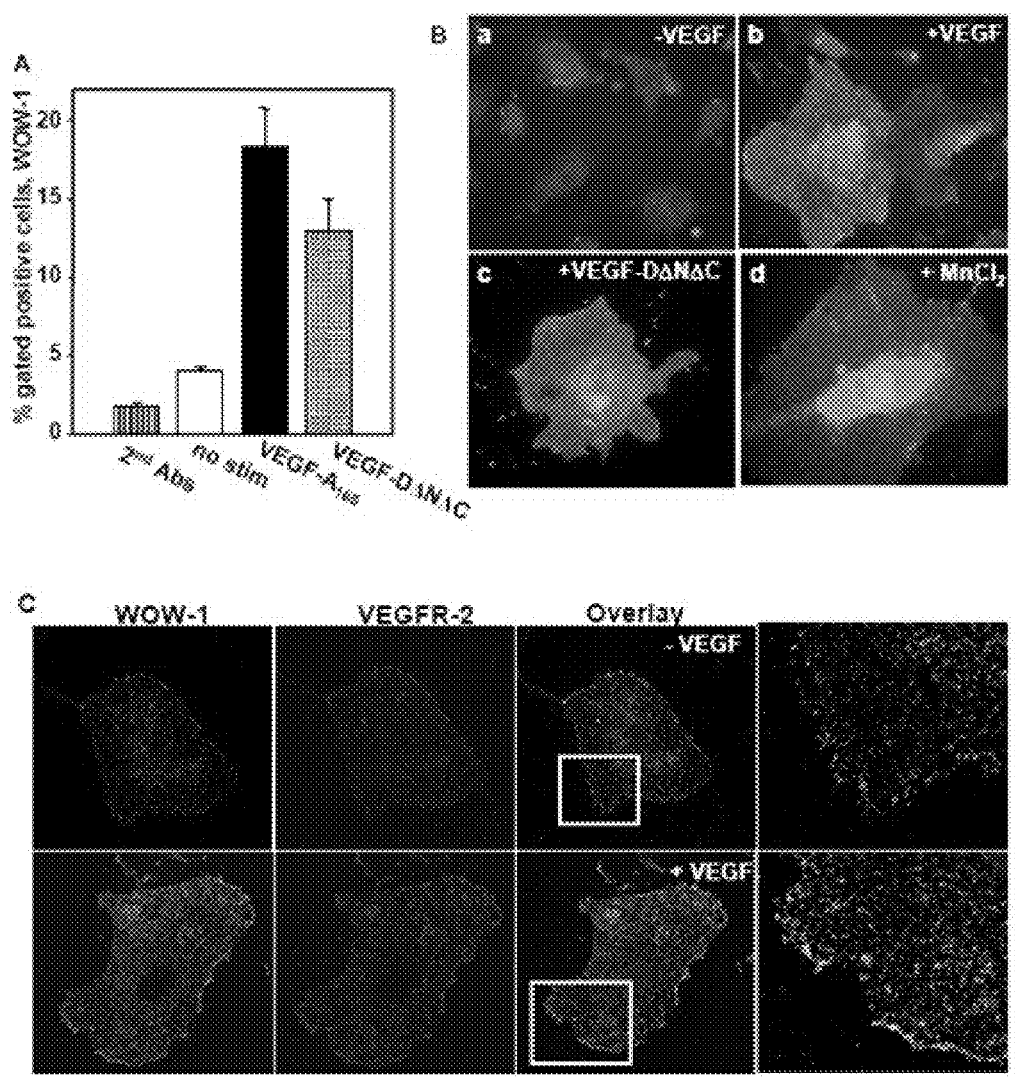

FIG. 11 illustrates activated $\alpha_v\beta_3$ integrin co-localizes with VEGFR-2 on endothelial cells. (A) To evaluate VEGF/VEGFR-2 dependent activation of $\alpha_v\beta_3$ integrin, semiconfluent, serum starved HUVECs were induced with VEGF-A165 or VEGFDΔNΔC. These cells were further incubated with WOW-1 Fab fragment and goat anti-mouse IgG labeled with AlexaFluor 488. Fixed cells were then analyzed by flow cytometry. (B) HUVECs were grown on the gelatin-coated glass coverslips. These cells were serum starved and induced with VEGF-A165, VEGF-DΔNΔC, or MnCl2 in presence of WOW-1 Fab fragment. Cells were washed and further incubated with goat anti-mouse IgG labeled with AlexaFluor 488. Cells were fixed, observed under fluorescence microscope and photographs were taken. (C) $\alpha_v\beta_3$ integrin and VEGFR-2 co-localize on endothelial cells. HUVECs were serum-starved overnight and stimulated with 20 ng/mL VEGF for 5 minutes. These cells were stained with WOW-1 and anti-VEGFR-2, followed by the incubation with goat anti-mouse IgG labeled with AlexaFluor 488 and goat anti-rabbit IgG conjugated with AlexaFluor 594. Without stimulatory signal (upper panel), very little co-localization of $\beta3$ integrin and VEGFR-2 was observed. Upon VEGF stimulation (lower panel), the affinity of $\alpha_v\beta_3$ increases and co-localized with VEGFR-2.

Figure 12:
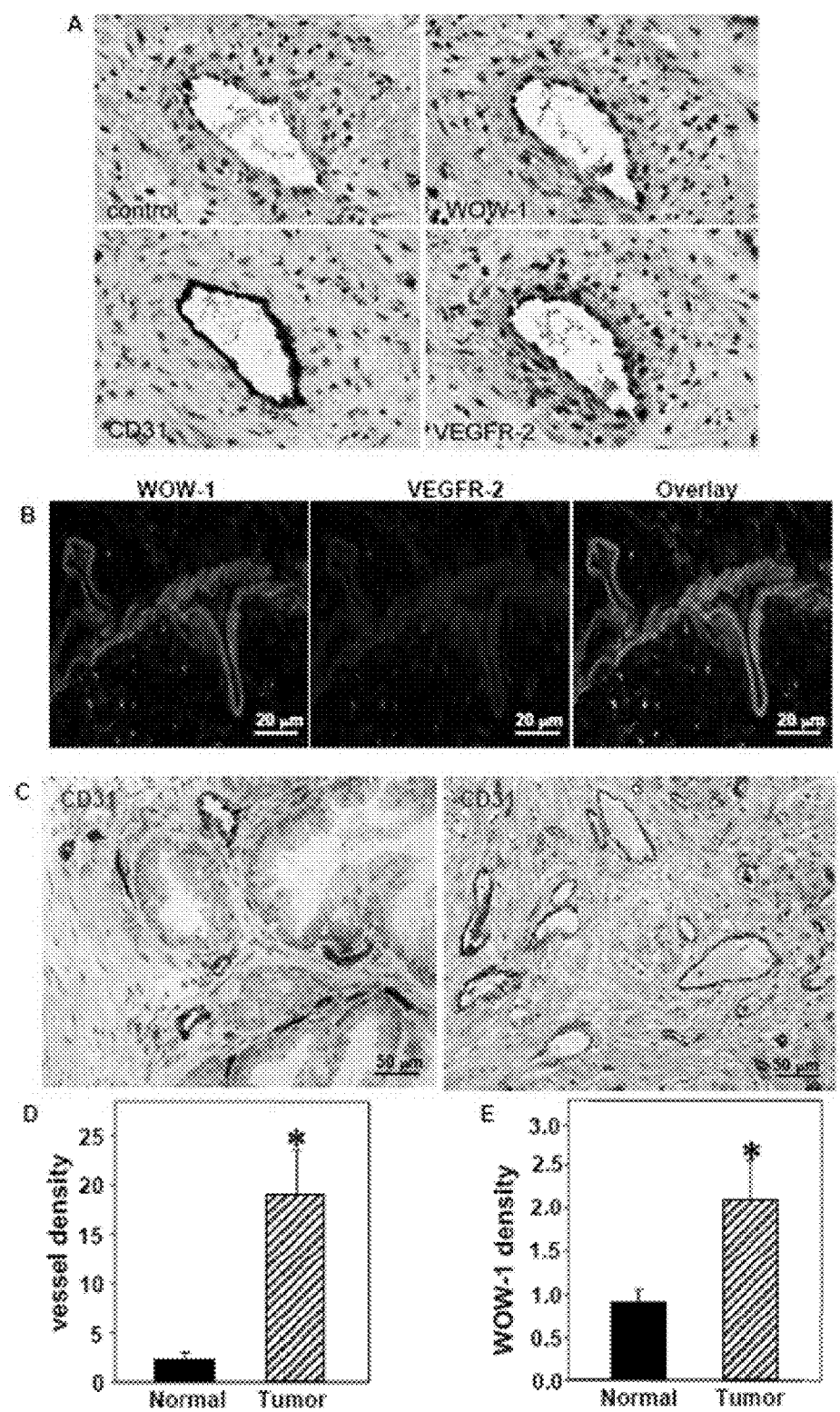

FIG. 12 illustrates the level of $\alpha_v\beta_3$ integrin activation is index for degree of tumor angiogenesis. (A) Activated $\alpha_v\beta_3$ integrin co-localizes with VEGFR-2 on endothelial cells of proliferating blood vessel. Parallel prostate tumor tissue sections were cut and stained for WOW-1 (activated $\alpha_v\beta_3$ integrin), CD31 (endothelial cell marker), and VEGFR-2. Blood vessels (revealed by CD31 staining) were positively stained for both WOW-1 and VEGFR-2, indicating the co-localization of activated $\alpha_v\beta_3$ with VEGFR-2 in tumor vasculature. (B) Frozen parallel prostate tumor sections were stained for activated αVβ3 integrin (WOW-1 Fab) and VEGFR-2. Tissue sections were analyzed under a confocal microscope and photographs were taken. (C-D) Normal prostate tissue (panel C) and prostate tumor sections (panel D) were stained for CD-31 and WOW-1. Vascular density was increased at least by 6 times in prostate tumors compared to normal prostate tissue. (E) Vascular density was positively correlated with the density of WOW-1-positive vasculature in the two tissue samples. Asterisks indicate significant difference over normal tissue.

Figure 13:
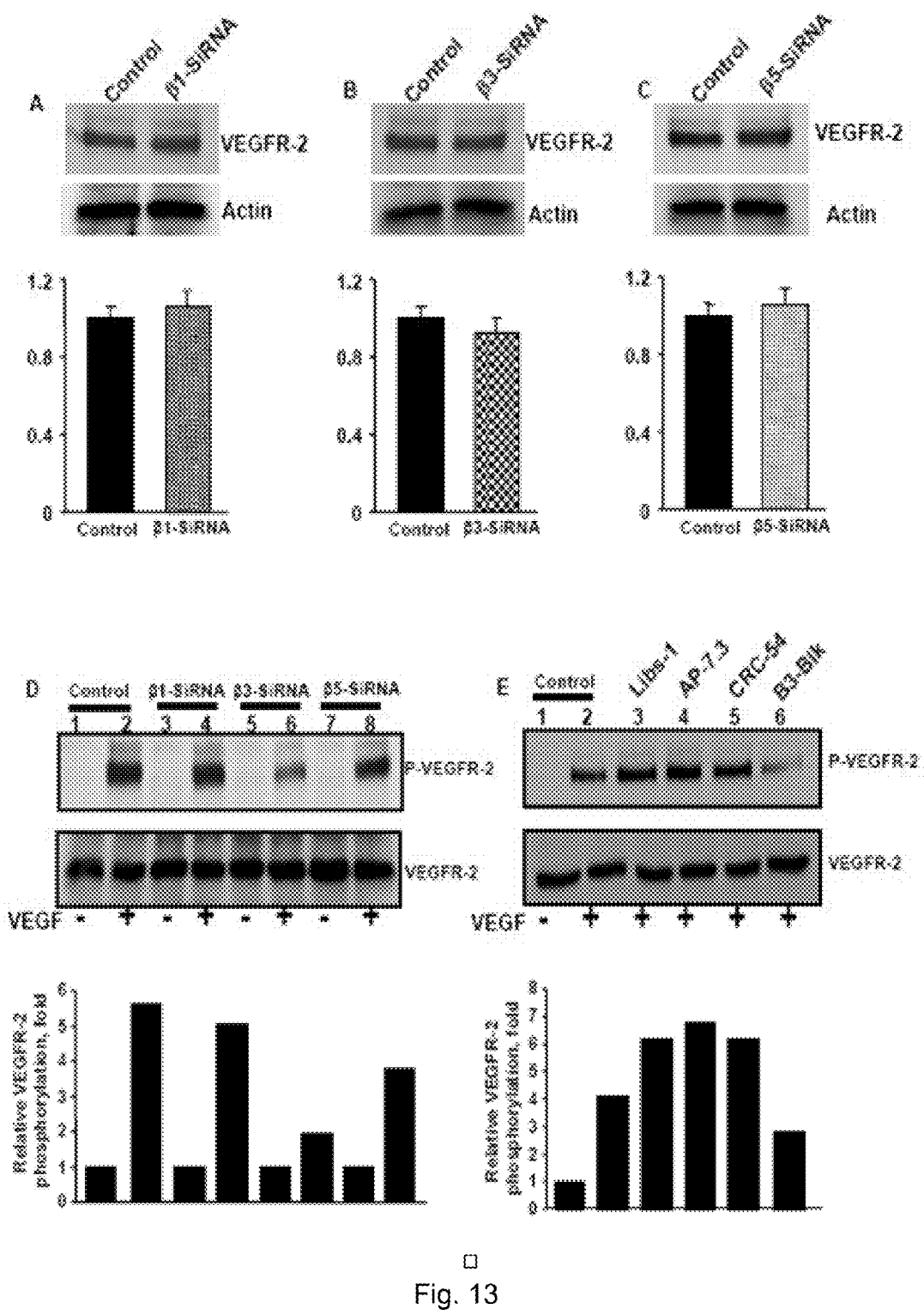

FIG. 13 illustrates VEGF-induced VEGFR-2 phosphorylation is subordinate to αvβ3 integrin activation status. (A-C) Effect of integrin knockdown on VEGFR-2 expression was evaluated by transfecting HUVECs with siRNA specific for (A) $\beta1$, (B) $\beta3$, or (C) $\beta5$ integrin. Cell lysates were analyzed for expression of VEGFR-2. Densitometry analysis was performed and results are shown as bar graphs (lower panels). (D-E) αvβ3 integrin activation dependent phosphorylation of VEGFR-2. HUVECs were transfected with $\beta1$, $\beta3$, or $\beta5$ integrin-specific siRNA and induced with 20 ng/mL VEGF for 5 min. (D) Cell lysates were analyzed for phosphorylation of VEGFR-2 using specific antibody. Densitometry analysis was performed and results are shown as bar graphs (lower panel). (E) HUVECs were incubated with αvβ3 integrin-activating antibody (Libs-1, AP-7.3, CRC-54) or β3 integrin blocking antibody. These cells were induced with VEGF for 5 min and cell lysates were analyzed for phosphorylation of VEGFR-2 using specific antibody. Densitometry analysis was performed and results are shown as bar graphs (lower panel).

Figure 14:
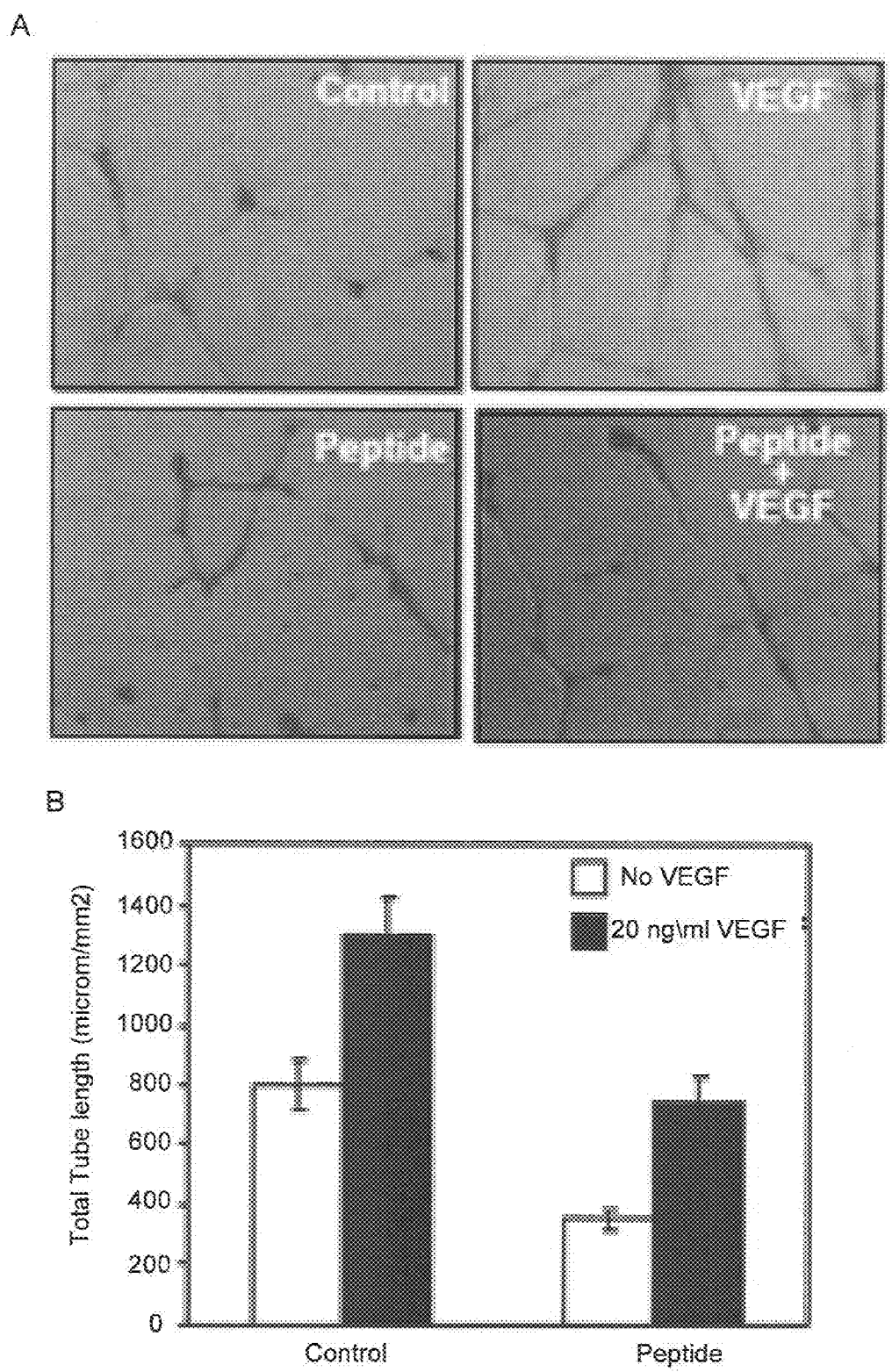

FIG. 14 illustrates (A) photographs of endothelial cell tube formation in a matrigel assay for endothelial cells subjected to VEGF, a peptide in accordance with the present invention, and VEGF in conjunction with a peptide in accordance with the present invention; and (B) a graph showing the results.

Figure 15:
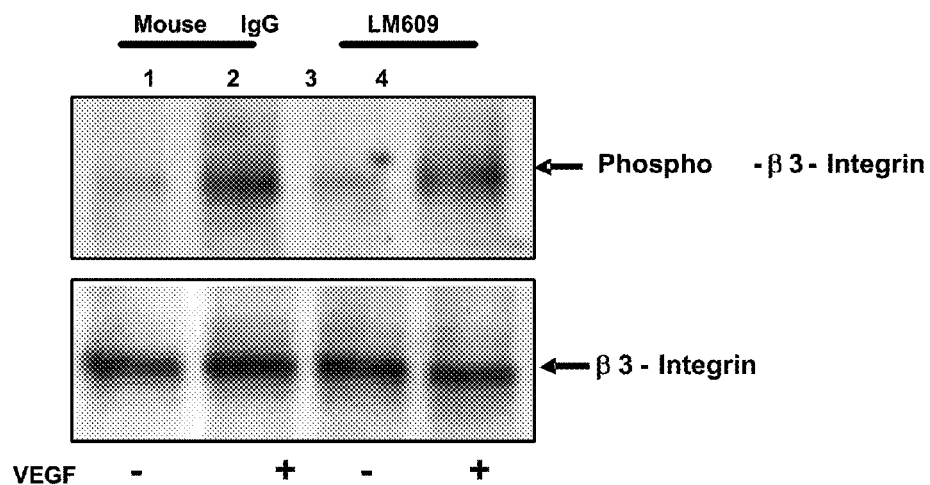

FIG. 15 are blots illustrating the phosphorylation status of $\beta_3$ integrin upon treatment with LM609 antibody (vitaxin).

Figure 16:
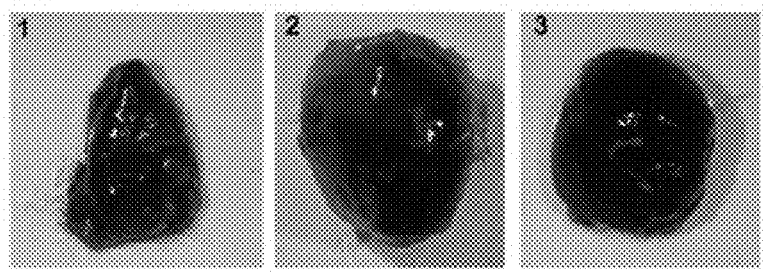
Figure 16:
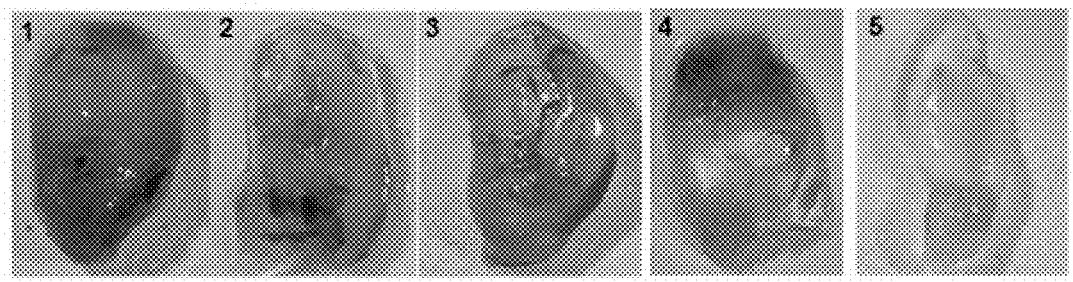

FIG. 16 illustrates photographs of matrigel plugs in accordance with an aspect of the invention.

Figure 17:
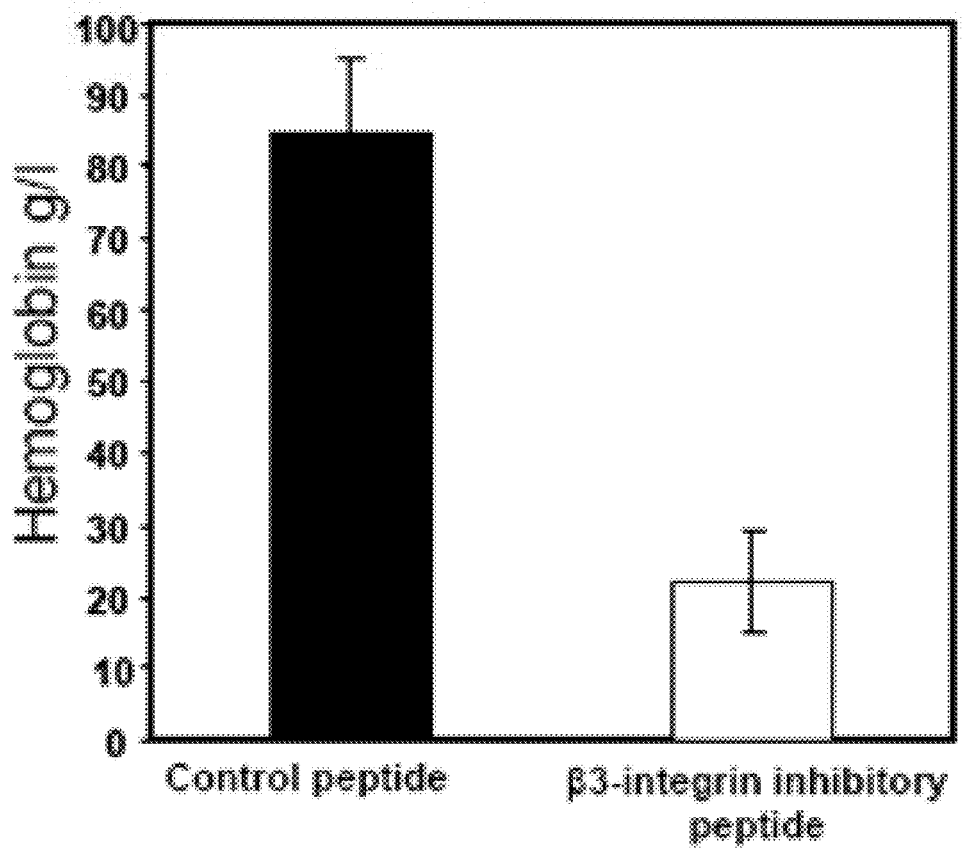

FIG. 17 illustrates a graph showing that $\beta_3$ cytoplasmic tail peptide inhibits angiogenesis in vivo.

Figure 18:
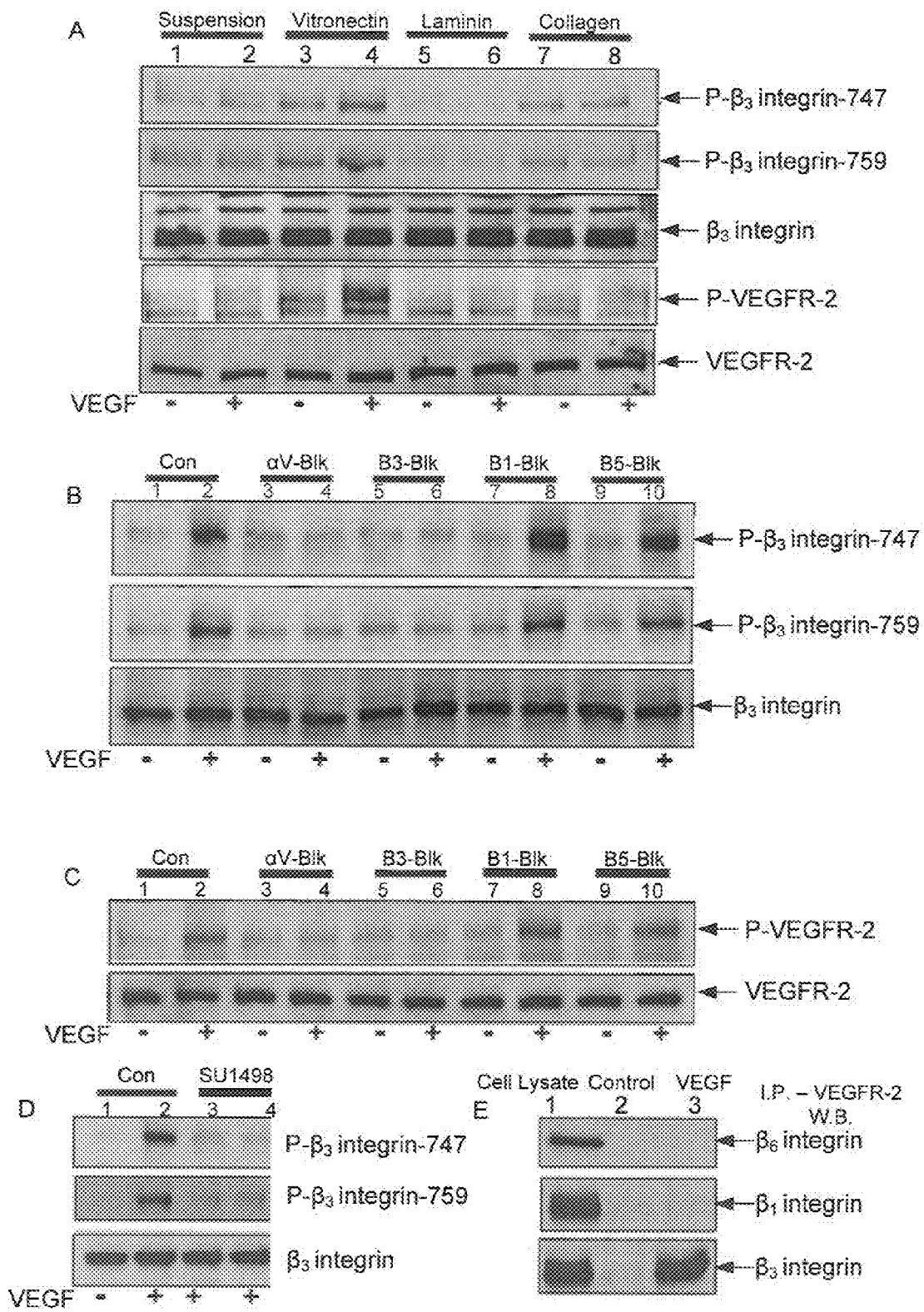

FIG. 18 illustrates phosphorylation β3 integrin cytoplasmic tyrosine motifs is crucial for VEGF induced VEGFR-2 activation. (A) HUVECs were either kept in suspension (lane 1 and 2) or plated on vitronectin (lane 3 and 4), laminin (lane 5 and 6), collagen (lane 7 and 8). These cells were induced with 20 ng/mL VEGF and cell lysates were analyzed for phosphorylation of cytoplasmic tyrosine motifs on β3 integrin and p-VEGFR-2 using specific antibodies. Cell lysates were also analyzed for equal levels of β3 integrin (middle panel) and VEGFR-2 (lower panel) as loading controls. (B-C) Effects of anti-αv and anti-β3 integrin blocking antibodies on β3 integrin and VEGFR-2 tyrosine phosphorylation. Semiconfluent HUVECs were incubated with specific or control antibody at 4° C. for 1 h. These cells were induced with VEGF and cell lysates were analyzed for phosphorylation of β3 integrin (upper panels B) and VEGFR-2 (upper panels C) using specific antibody. Cell lysates were also analyzed for β3 integrin and VEGFR-2 as loading control. (D) Serum starved HUVECs were treated with 400 nm and 800 nm of VEGFR-2 inhibitor SU1498 (lane 3 and 4) and these cells were induced with VEGF. Cell lysates were analyzed for tyrosine phosphorylation of β3-integrin using specific antibodies. (E) β3 interacts with VEGFR-2 following VEGF stimulation. Serum starved HUVECs were induced with VEGF and cell lysates were immunoprecipitated with anti-VEGFR-2 antibody and immunoblotted with anti-β5 (upper panel), anti-β1 (middle panel), anti-β3 (lower panel) integrin antibody separately.

Figure 19:
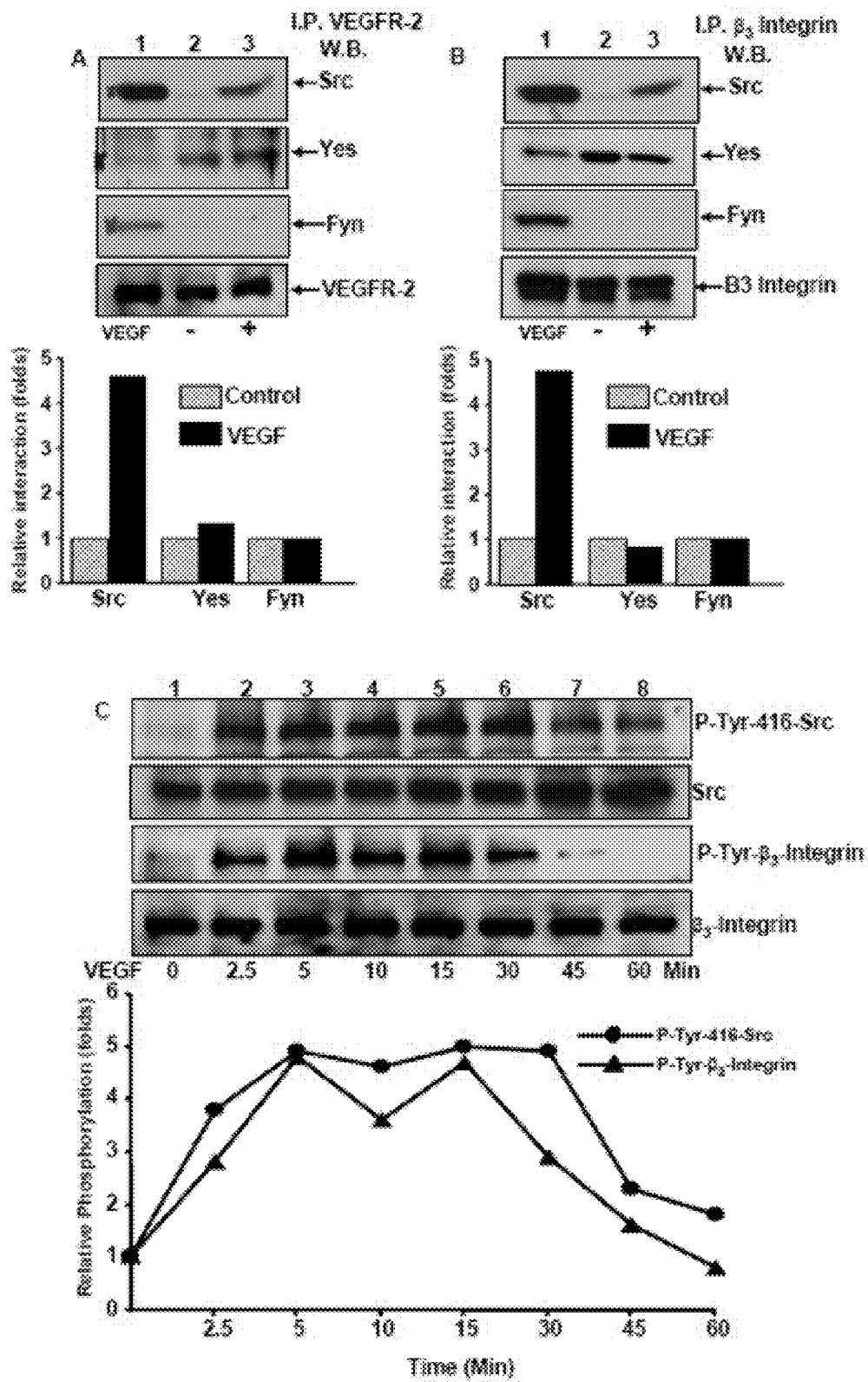

FIG. 19 illustrates VEGF differentially induces SFK interactions with β3 integrin and VEGFR-2. (A-B) Semiconfluent serum-starved HUVECs were induced with 20 ng/mL VEGF for 10 min. Cell lysates were immunoprecipitated with anti-VEGFR2 (A) or anti-β3 integrin (B) antibody. Immunocomplexes were resolved by SDSPAGE and analyzed for Src, Yes and Fyn using specific antibodies (lane 2 and 3). HUVECs lysate was used as positive control (lane 1). Densitometry analysis was performed and fold changes were indicated (lower panel A and B). (C) VEGF induced β3 integrin phosphorylation follows c-Src phosphorylation. Serum-starved HUVECs were induced with 20 ng/mL VEGF for 0-60 min. A portion of cell lysate was analyzed for activation phosphorylation of c-Src (Tyr-416) using specific antibody (upper panel C). Another portion of the cell lysate was immunoprecipitated with anti-β3 integrin antibody and immunoblotted with antiphosphotyrosine antibody (middle lower panel C). Densitometry analysis was performed and fold changes over control are indicated (lower panel C).

Figure 20:
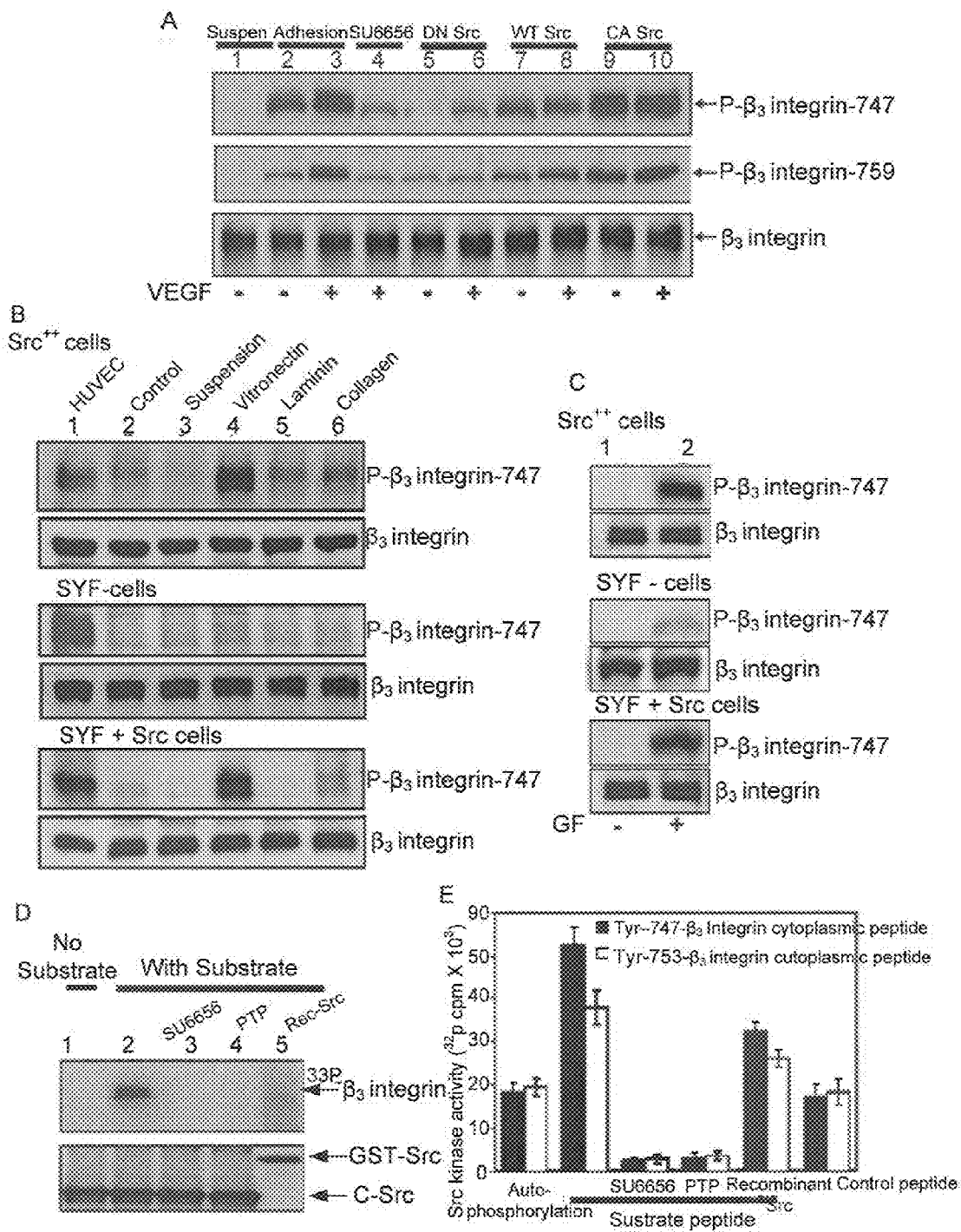

FIG. 20 illustrates c-Src directly phosphorylates β3 integrin on cytoplasmic tyrosine motifs. (A) HUVECs were either kept in suspension (lane 1) or in adhesion (lane 2 and 3) in presence of SU6656 (lane 4). HUVECs were also transfected with wild-type Src (lane 5 and 6), dominant negative Src (lane 7 and 8), or catalytically-active Src (lane 9 and 10) and these cells were induced with 20 ng/mL VEGF. Cell lysates were resolved by SDS-PAGE and analyzed for phosphorylation of β3 integrin using specific antibodies (upper and middle panel). (B-C) Semiconfluent serum-starved Src++, SYF, and SYF+Src cells were either kept in suspension (lane 3) or plated on uncoated plastic surface (lane 2), vitronectin- (lane 4), laminin- (lane 5), or collagen- (lane 6) coated surface. HUVECs plated on vitronectin-coated surface were used as positive control (lane 1). These cell lysates were analyzed for phosphorylation of β3 integrin using specific antibody (upper panels B). Cell lysates were also analyzed for β3 integrin as a loading control (lower panels B). Src++, SYF, and SYF+Src cells plated on plastic surface were also induced with bFGF and levels of β3 integrin phosphorylation were detected using a specific antibody (upper panels C). Cell lysates were also analyzed for β3 integrin as loading control (lower panels C). (DE) A kinase assay was performed either using recombinant β3 integrin cytoplasmic tail-GST fusion protein (panel C) or peptide derived from distinct cytoplasmic region of β3 integrin (panel D). Kinase assay were performed as described in "material and methods". Densitometry analysis was performed and fold changes over control are indicated.

Figure 21:
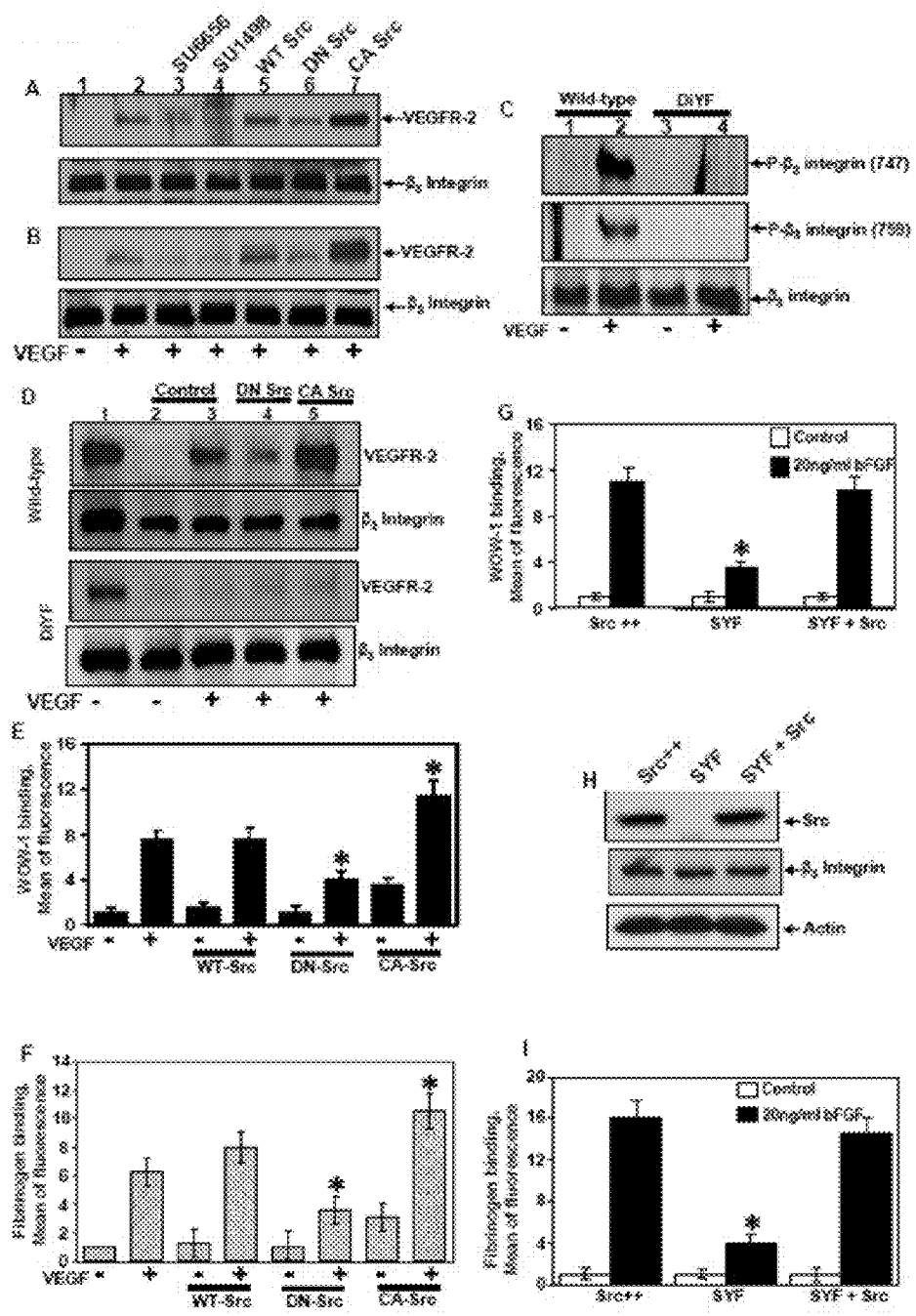

FIG. 21 illustrates c-Src-dependent β3 integrin cytoplasmic tyrosine motifs phosphorylation required for β3 integrin/VEGFR-2 interaction and β3 integrin activation and ligand binding. (A-B) HUVECs treated with various pharmacological inhibitors or over expressed with various Src constructs were surface labeled with membrane-impermeable sulpho-NHS biotin and these cells were induced with 20 ng/mL VEGF. Cell lysates were immunoprecipitated with anti-β3 integrin antibody and immunoblotted with anti-streptavidin antibody (upper panel A). Under similar condition, HUVECs were induced with VEGF and cell lysates were immunoprecipitated with anti-β3 integrin antibody and immunoblotted with anti-VEGFR-2 antibody (upper panel B). Blots were also analyzed for β3 integrin as loading control (lower panel A and B). (C-D) Wild type and DiYF mouse lung microvascular endothelial cells were stimulated with 20 ng/mL VEGF. Cell lysates were analyzed for phosphorylation of β3 integrin using specific antibodies (upper and middle panel of C). Wild type and DiYF mouse lung microvascular endothelial cells were transfected with DN Src and CA Src constructs and plated on vitronectin-coated plates. These cells were induced with VEGF. Cell lysates were immunoprecipitated with anti-β3 integrin antibody and immunoblotted with anti-VEGFR-2 antibody (upper panel D). Blots were also analyzed for β integrin as loading control (lower panels of C and D). (E-F) HUVECs were transiently transfected with various Src constructs. These cells were stimulated with VEGF and incubated with WOW-1 Fab fragments (panel E) or FITC-fibrinogen (panel F) for 30 min at 37° C. Cells were fixed, washed, and analyzed by flow cytometry. Bars represent mean fluorescence intensity of three independent experiments performed in triplicate (panel E and F). (G-I) Src++, SYF, SYF+Src cells were stimulated with bFGF and incubated with WOW-1 Fab fragments (panel G) or FITC-fibrinogen (panel I) for 30 min at 37° C. Cells were fixed with 4% formaldehyde, washed, and analyzed by flow cytometry. Expression levels of β3 integrin and Src in these cells were conformed by Western blot analysis (panel H). Asterisks indicate significant difference over control (P<0.034).

Figure 22:
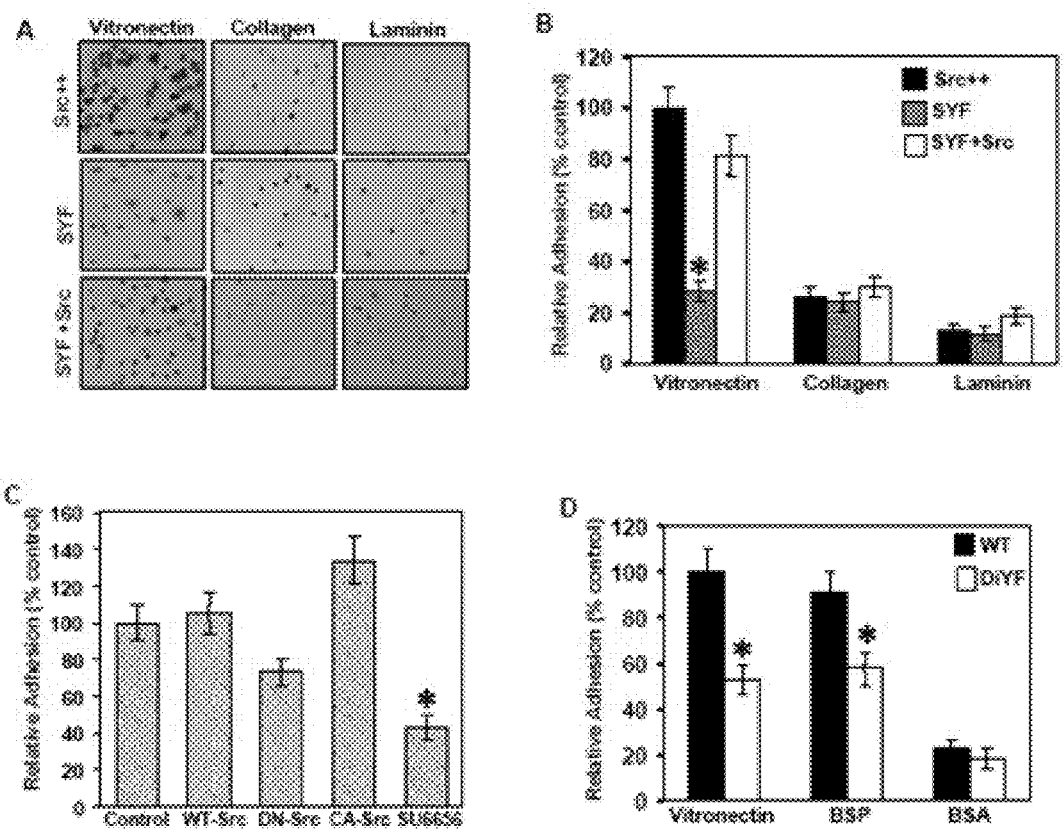

FIG. 22 illustrates c-Src mediated phosphorylation of β3 integrin cytoplasmic tyrosine motifs required for αvβ3 integrin outside-in signaling. (A-B) Src++, SYF, SYF+Src cells were washed and plated on vitronectin-, collagen-, or laminin-coated plates. Numbers of attached cells per field were counted. Number of Src++ cells adhered on vitronectin was assigned a value of 100%. (C) HUVECs were either transfected with various forms of Src or treated with SU6656. These cells were suspended on vitronectin-coated plates.

Number of untransfected HUVECs adhered on vitronectin was assigned a value of 100%. (D) Wild type and DiYF mouse lung microvascular endothelial cells were suspended on vitronectin- or bone sialoprotein-coated plates. Numbers of attached cells per field were counted and wild-type cells adhered on vitronectin was assigned a value of 100%. Asterisks indicate significant difference over control (P<0.028).

Figure 23:
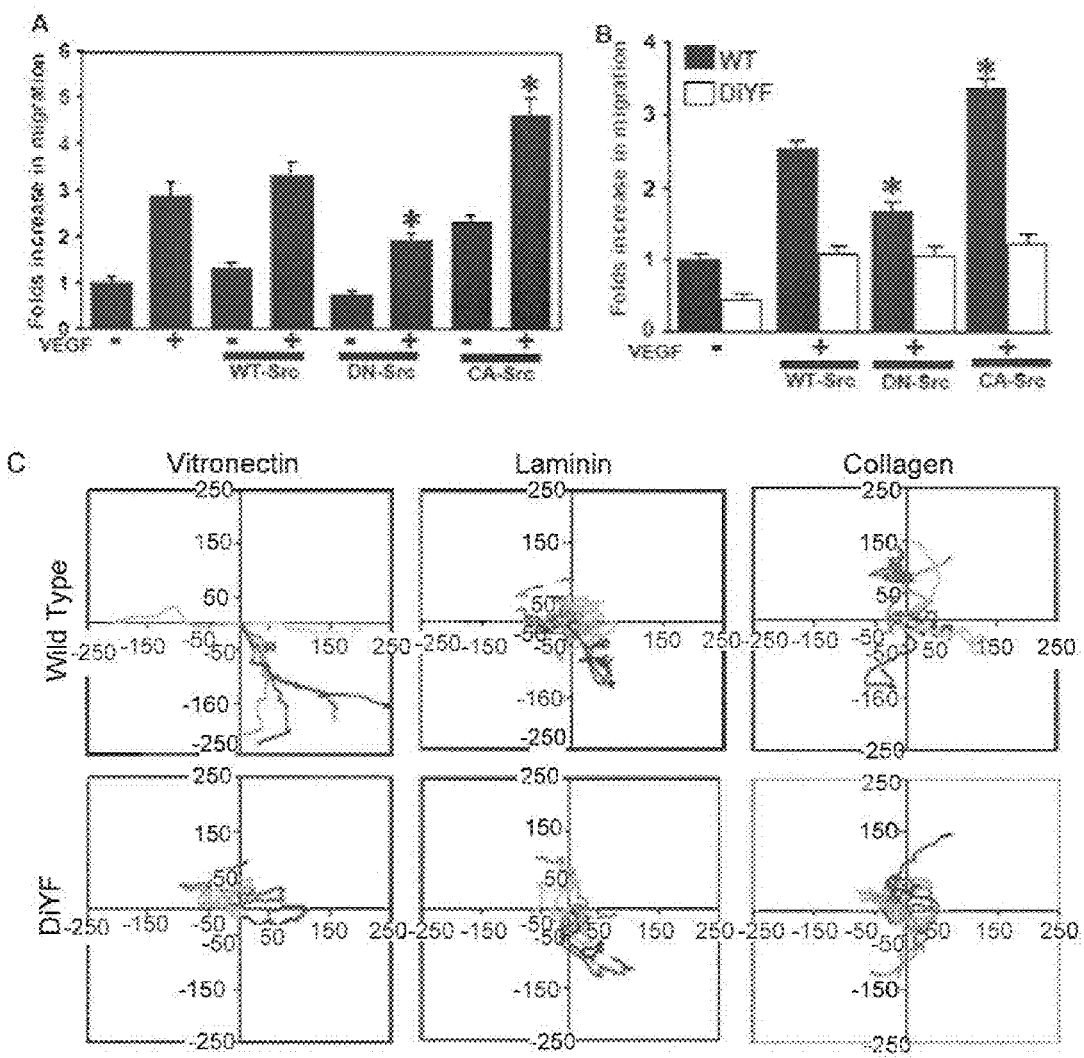

FIG. 23 illustrates c-Src dependent phosphorylation of β3 integrin cytoplasmic tyrosine motifs required for αvβ3 integrin-dependent directional migration of endothelial cells. (A-B) HUVECs (panel A) or wild type and DiYF mouse lung microvascular endothelial cells (panel B) were transfected with various forms of Src. These cells were seeded on vitronectin-coated upper wells of Boyden-type migration chamber. Cells were allowed to migrate and non-migrated cells adhered to the top surface were removed. Migrated cells were stained and number of cells per field was counted. Numerical values are represented as bar diagram and fold changes over control are indicated. (C) Wild type and DiYF mouse lung microvascular endothelial cells were grown on vitronectin-, laminin or collagen-coated plates. A wound was created across the cell monolayer by scraping away a swath of cells. Representative cell paths (n=6) are shown tracked by videolapse microscopy in presence of 20 ng/mL VEGF over period of 10 h. Cell paths are reconstituted such that all paths starts from origin. Unit of measures on axes is μm/h. Asterisks indicate significant difference over WT-Src transfected cells (P<0.039).

Figure 24:
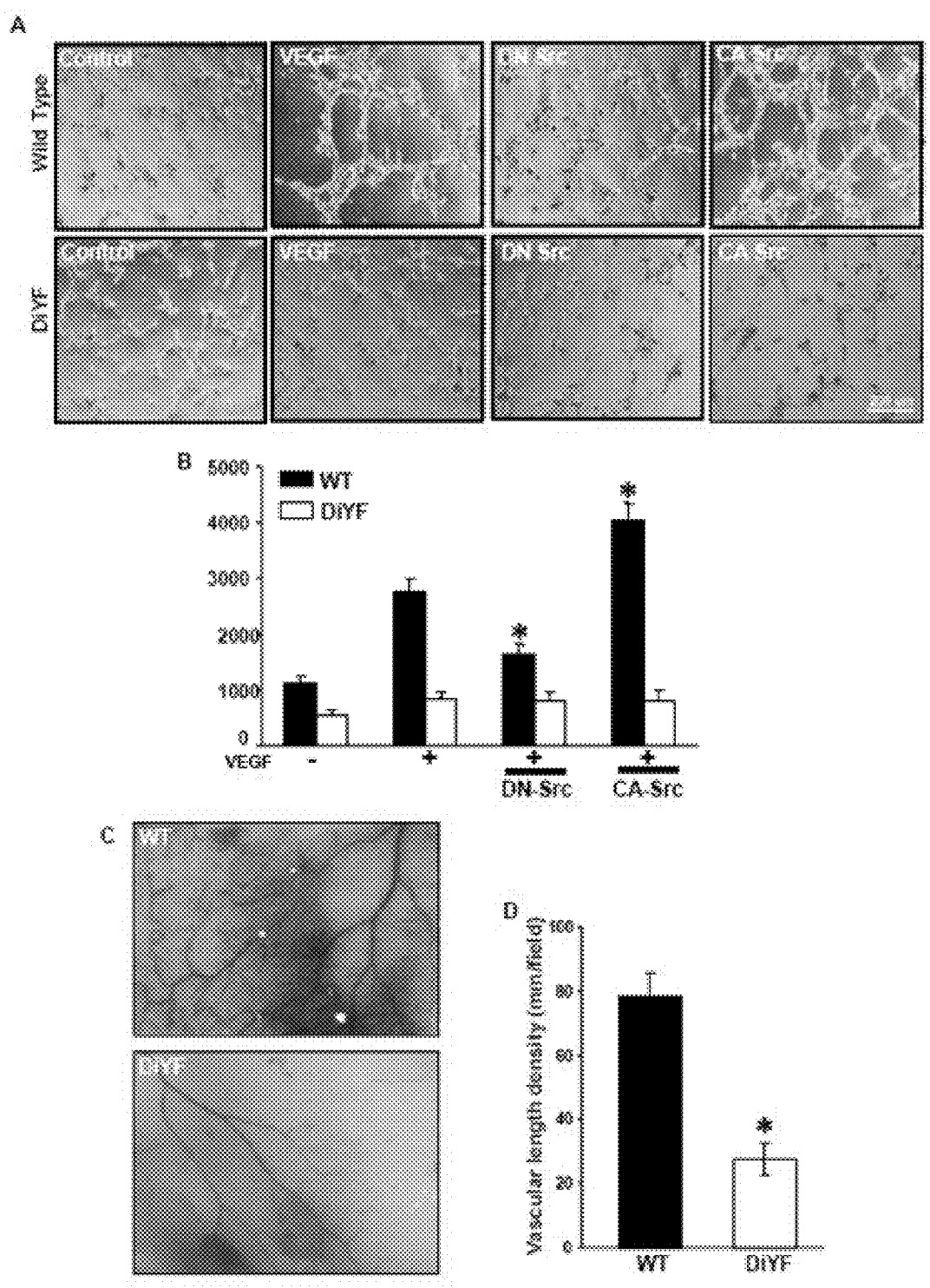

FIG. 24 illustrates β3 integrin cytoplasmic tyrosine phosphorylation is required for angiogenesis in vitro and in vivo. (A-B) Wild type and DiYF mouse lung microvascular endothelial cells were transfected with various forms of Src. These cells were transferred to Matrigel-coated plates and incubated in presence of VEGF for 8 h. (A) Three random fields were photographed using phase-contrast microscope. (B) Length of tubes in random fields from each well was analyzed using ImagePro software. (C) Tumor induced In vivo angiogenesis were assessed using hollow fiber filled with B16F10 mouse melanoma tumor cells as described in the example. (D) Cumulative vessel length were measured and indicated as bar diagram. Asterisks indicate significant difference over control (P<0.034).

DETAILED DESCRIPTION

The present invention relates generally to a method of modulating angiogenesis in a tissue, and thereby affecting events in the tissue that depend on angiogenesis. The method comprises administering to the tissue a therapeutically effective amount of an agent that modulates (e.g., inhibits or stimulates) complex formation of $\alpha_v\beta_3$ integrin and VEGFR2.

In accordance with one aspect of the invention, it was found that VEGF stimulation via activation of it major receptor VEGFR2 leads to the tyrosine phosphorylation of $\alpha_v\beta_3$ integrin and integrin activation. In vivo and in vitro experiments show that tyrosine residues within $\alpha_v\beta_3$ integrin are essential for complex formation with VEGFR2 and for sustained activation of VEGFR2. Impaired or inhibited cytoplasmic β3 integrin and VEGFR2 complex formation, reduced VEGFR2 activation, and inhibited angiogenesis. The inhibition of $\alpha_v\beta_3$ integrin and VEGFR2 complex formation suppresses the function of both receptors. This is exemplified by reduced angiogenesis in mice with impaired β3 tyrosine phosphorylation. A similar complex formation between $\alpha_v\beta_3$ integrin and VEGFR2 also occurs on tumor cells to promote tumor angiogenesis.

A population of cells or tissue that express $\alpha_v\beta_3$ integrin and VEGFR2, such as endothelial cells and tumor cells, can be contacted (e.g., directly or locally) with a therapeutically effective amount of an agent under conditions effective to inhibit complex formation of $\alpha_v\beta_3$ integrin and VEGFR2. The inhibition of the complex formation of $\alpha_v\beta_3$ integrin and VEGFR2 can be used to suppress angiogenesis in endothelial cells and tumor-induced angiogenesis. Moreover, since it was found that tumors express $\alpha_v\beta_3$ integrin and VEGFR2 and over-express VEGF resulting in VEGF dependent autocrine loop, the agents in accordance with the present invention can potentially suppress tumor cell-proliferation and metastatic activity.

Additionally, complex formation of $\alpha_v\beta_3$ integrin and VEGFR2 occurs only on cells stimulated with VEGF or exposed to certain integrin ligands (e.g., vitronectin). Stimulation and over stimulation with VEGF is associated with pathological conditions, such as tumor angiogenesis. On normal quiescent endothelial cells $\alpha_v\beta_3$ integrin may be expressed but it does not complex with VEGFR2. The method of the present invention can target activated endothelial cells associated with pathological conditions (e.g., pathological or aberrant angiogenesis) and tumor cells without targeting normal quiescent endothelial cells. This is in contrast to agents, such as VITAXIN, that block ligand binding to $\alpha_v\beta_3$ integrin or VEGFR2.

One aspect of the present invention therefore relates to a method of inhibiting pathological angiogenesis by administering a therapeutically effective amount of agent that substantially inhibits complex formation of $\alpha_v\beta_3$ integrin and VEGFR2 but does not block or inhibit binding of natural ligands to VEGFR2 and $\alpha_v\beta_3$ integrin. As used herein, "inhibit", "inhibiting" or "inhibition" includes any measurable reproducible substantial reduction in: the interaction of $\alpha_v\beta_3$ integrin and VEGFR2; angiogenesis; symptoms of diseases correlated to angiogenesis; or any other activities complex formation of $\alpha_v\beta_3$ integrin and VEGFR2 may mediate. A substantial reduction is a "reproducible", i.e., consistently observed reduction in complex formation. A "substantial reduction" in terms of the present application is defined as a reproducible reduction (in complex formation of $\alpha_v\beta_3$ integrin and VEGFR2) of at least about 25%, or about 50%.

The present method of inhibiting angiogenesis in a tissue comprises contacting a tissue in which angiogenesis is occurring, or is at risk for occurring, with a composition comprising a therapeutically effective amount of an agent that is capable of inhibiting complex formation of $\alpha_v\beta_3$ integrin and VEGFR2 (i.e., $\alpha_v\beta_3$ integrin/VEGFR2 complex inhibiting agent). Thus, the method comprises administering to a patient a therapeutically effective amount of a physiologically tolerable composition containing an agent that is an inhibitor of complex formation of $\alpha_v\beta_3$ integrin and VEGFR2.

The dosage ranges for the administration of the agent depend upon the form of the inhibitor, and its potency, and are amounts large enough to produce the desired effect in which angiogenesis and the disease symptoms mediated by angiogenesis are ameliorated. The dosage should not be so large as to cause adverse side effects. The dosage can also be adjusted by the individual physician in the event of any complication.

A therapeutically effective amount is an amount of agent that is an inhibitor of complex formation of $\alpha_v\beta_3$ integrin and VEGFR2 sufficient to produce a measurable inhibition of angiogenesis in the tissue being treated, i.e., an angiogenesis-inhibiting amount. Inhibition of angiogenesis can be measured in situ by immunohistochemistry or by other methods known to one skilled in the art.

In one aspect of the invention, the agent can comprise an inhibiting compound or inhibiting peptide that competes with $\alpha_v\beta_3$ integrin or VEGFR2 for interaction between the two receptors. The inhibiting peptide can have an amino acid sequence of about 5 to about 50 amino acids (e.g., about 5 to about 30 amino acids) that corresponds to an about 5 to about 50 amino acid cytoplasmic portion of the amino acid sequence of the VEGFR2 or $\alpha_v\beta_3$ integrin. By corresponding to, it is meant the inhibiting peptide has an amino acid sequence with a sequence identity that is substantially homologous to a portion of the amino acid sequence of $\alpha_v\beta_3$ integrin or VEGFR2. By substantially homologous, it is meant the inhibiting peptide has at least about 70%, about 80%, about 90% or about 100% sequence identity with a portion of the amino acid sequence of $\alpha_v\beta_3$ integrin or VEGFR2.

In one example, the inhibiting peptide can correspond to an about 5 to about 50 amino acid portion of the cytoplasmic domain of $\alpha_v\beta_3$ integrin or VEGFR2. Particular peptides include those that correspond to a cytoplasmic portion of $\alpha_v\beta_3$ integrin or VEGFR2 domain that comprises a tyrosine residue. It was found that phosphorylation of tyrosine is required for complex formation of $\alpha_v\beta_3$ integrin and VEGFR2. A peptide comprising an amino acid sequence that corresponds to a portion of the amino acid sequence of $\alpha_v\beta_3$ integrin or VEGFR2 containing a tyrosine residue can compete with the tyrosine residue for phosphorylation.

In another example, the inhibiting peptide can comprise about 5 to about 30 amino acids and have substantially the same sequence identity as an about 5 to about 30 amino acid portion of the cytoplasmic domain of $\beta_3$ that includes tyrosine. For example, the inhibiting peptide can have an amino acid sequence of about 5 to about 30 amino acids and correspond to (or have a sequence identity of) a portion of the cytoplasmic domain of $\beta_3$ integrin that includes tyrosine 747. An example of a peptide that can be used as an agent in accordance with the present invention has the amino acid sequence of:

```
    DTANNPLYpKEATSTFT-COOH.      (SEQ ID NO: 1)
```

This peptide includes a phosphorylated tyrosine residue and corresponds to a portion of the cytoplasmic domain of $\beta_3$ integrin comprising the amino acid sequence

```
    DTANNPLYKEATSTFTNITYRGT.     (SEQ ID NO: 3)
```

Other examples of peptides that can be used as an agent in accordance with the present invention and that correspond to a portion of the amino acid sequence of $\alpha_v\beta_3$ integrin can comprises an amino acid sequence selected from group consisting of:

```
         KEFAKFEEER          (SEQ ID NO: 4)
         and
         ARAKWDTANN.         (SEQ ID NO: 5)
```

Still other examples of peptides that can be used as an agent in accordance with the present invention and that correspond to a portion of the amino acid sequence of VEGRFR2 can comprises an amino acid sequence selected from group consisting of:

```
    CMEEEEVCDPKFHYDNTAGI;            (SEQ ID NO: 6)
    QTSGYQSGYHSDDTDTTVYS;            (SEQ ID NO: 7)
    RDIYKDPDYVRKGDARLPLK;            (SEQ ID NO: 8)
    WMAPETIFDRVYTIQSDVWSFGV;         (SEQ ID NO: 9)
    LGASPYPGVKIDEEFCRRLK;            (SEQ ID NO: 10)
    EGTRMRAPDYTTPEMYQTML;            (SEQ ID NO: 11)
    and
    GNLLQANAQQDGKDYIVLPISETLSMEEDS.  (SEQ ID NO: 12)
```

The peptides in accordance with the present invention can be subject to various changes, substitutions, insertions, and deletions where such changes provide for certain advantages in its use. In this regard, a peptide that is an inhibitor of complex formation of $\alpha_v\beta_3$ integrin and VEGFR2 corresponds to, rather than is identical to, the sequence of a recited peptide where one or more changes are made and it retains the ability to function as an inhibitor of complex formation of $\alpha_v\beta_3$ integrin and VEGFR2.

Thus, a peptide can be in any of a variety of forms of peptide derivatives, that include amides, conjugates with proteins, cyclized peptides, polymerized peptides, analogs, fragments, chemically modified peptides, and the like derivatives. In one example, the peptides in accordance with the present invention can include phosphorylated tyrosine residues to inhibit complexing of the cytoplasmic portions of $\alpha_v\beta_3$ integrin and VEGFR2.

The term "analog" includes any peptide having an amino acid residue sequence substantially identical to a sequence specifically shown herein in which one or more residues have been conservatively substituted with a functionally similar residue and that is an inhibitor of complex formation of $\alpha_v\beta_3$ integrin and VEGFR2 as described herein. Examples of conservative substitutions include the substitution of one nonpolar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite inhibition activity.

"Chemical derivative" refers to a subject peptide having one or more residues chemically derivatized by reaction of a functional side group. Such derivatized molecules include for example, those molecules in which free-amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides of the present invention also include any peptide having one or more additions and/or deletions or residues relative to the sequence of a peptide whose sequence is shown herein, so long as the requisite activity is maintained.

The term "fragment" refers to any subject peptide having an amino acid residue sequence shorter than that of a peptide whose amino acid residue sequence is shown herein.

Additional residues may also be added at either terminus of a peptide for the purpose of providing a "linker" by which the peptides of this invention can be conveniently affixed to a label or solid matrix, or carrier.

Labels, solid matrices and carriers that can be used with the polypeptides of this invention are described herein below.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a subject polypeptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

The polypeptide of the present invention can also be in the form of a conjugate protein or drug delivery construct having at least a transport subdomain(s) or moiety(ies) (i.e., transport moieties). The transport moieties can facilitate uptake of the complex inhibiting polypeptide into a mammalian (i.e., human or animal) tissue or cell. The transport moieties can be covalently linked to the polypeptide. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the polypeptide.

The transport moieties can be repeated more than once in the polypeptide. The repetition of a transport moiety may affect (e.g., increase) the uptake of the peptide by a desired cell. The transport moiety may also be located either at the amino-terminal region of an active agent or at its carboxy-terminal region or at both regions.

In an aspect of the invention, the transport moiety can include at least one transport peptide, such as the TAT-mediated protein delivery sequence described in Vives (1997) 272: 16010-16017. An example of a peptide in accordance with the present that includes a cell penetrating peptide can have the following amino acid sequence <u>YGKKRRQRRRG</u> DTAN-NPLYpKEATSTFT-COOH (SEQ ID NO: 2), where the underlined portion comprises the cell penetrating peptide portion.

Additional examples of transport sequences that can be used in accordance with the present invention include polyargine sequences (Wender et al. 2000, PNAS 24: 13003-13008) and antennapedia (Derossi (1996) J. Biol. Chem. 271: 18188-18193). Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157 (Crisanti et al,) incorporated by reference in their entirety). Similarly, HIV Tat protein was shown to be able to cross cellular membranes (Frankel A. D. et al., Cell, 55: 1189).

Any peptide or compound of the present invention may also be used in the form of a pharmaceutically acceptable salt. Acids, which are capable of forming salts with the peptides of the present invention, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g. ethanolamine, diethanolamine and the like).

A peptide of the present invention also referred to herein as a subject peptide, can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

In another aspect of the invention, the agent that inhibits complex formation of $\alpha_v\beta_3$ integrin and VEGFR2 can comprise a c-SRC kinase inhibitor. It was found that $\alpha_v\beta_3$ integrin tyrosine phosphorylation is crucial for VEGF tyrosine phosphorylation of VEGFR2 and the $\alpha_v\beta_3$ integrin tyrosine phosphorylation is directly mediated by c-SRC kinase, which is able to phosphorylate the cytoplasmic domain of $\alpha_v\beta_3$. Thus, c-SRC via direct phosphorylation of $\alpha_v\beta_3$ integrin cytoplasmic motif controls functional association between $\alpha_v\beta_3$ and VEGFR2, which in turn regulates activation of both receptors on endothelial cells.

In one aspect, the c-SRC inhibitor can comprise a 3-(4,5,6,7-tetrahydroinol-2-ylmethylidene)-2-indolinone derivative that inhibits $\alpha_v\beta_3$ cytoplasmic phosphorylation. Examples of 3-(4,5,6,7-tetrahydroinol-2-ylmethylidene)-2-indolinone derivatives include compounds having the following general formula:

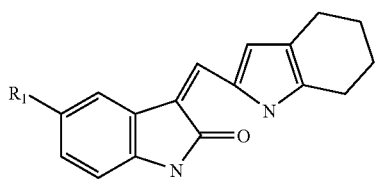

where $R_1$ is —S(O)$_n$R$_2$ (where n is 0, 1, or 2 and R$_2$ is alkyl or aralkyl) or —SO$_2$NR$_3$R$_4$ where R$_3$ and R$_4$ are independently hydrogen, alkyl, cycloalkyl, alkoxyalkyl, or hydroxyalkyl.

Examples of particular 3-(4,5,6,7-tetrahydroinol-2-ylmethylidene)-2-indolinone derivatives include 2-oxo-3(4,5,6,7-tetrahydro-1-H-indol-2-ylmethylene)-2,3-dihydro-1H-indole-5-sulfonic acid dimethylamide and 2-oxo-3(4,5,6,7-tetrahydro-1-H-indol-2-ylmethylene)-2,3-dihydro-1H-indole-5-sulfonic acid amide, both of which are commercially available from Sugen, Inc. (San Francisco, Calif.) under the tradenames SU6566 and SU6657.

Other examples of 3-(4,5,6,7-tetrahydroinol-2-ylmethylidene)-2-indolinone derivatives that can be potentially used as c-SRC inhibitors to $\alpha_v\beta_3$ cytoplasmic phosphorylation include 3-(4,5,6,7-tetrahydroinol-2-ylmethylidene)-2-indolinone derivatives disclosed in U.S. Pat. No. 6,777,417, which is herein incorporated by reference in its entirety. Still other examples of c-SRC inhibitors that can potentially be used in accordance with the present invention include c-SRC inhibitors disclosed in, for example, PCT application WO 01/00214 and US Patent Publication 2006/0223815, both of which are herein incorporated by reference in their entirety.

In a further aspect, the c-SRC inhibitor can include a biological agent that inhibits expression and/or activity of c-SRC-kinase. In one example, the biological agent can include an antisense oligonucleotide that inhibits expression and/or activity of the c-SRC-kinase. Antisense nucleotides are relatively short nucleic acids that are complementary (or antisense) to the coding strand (sense strand) of the mRNA encoding the c-SRC kinase. Although antisense oligonucleotides are typically RNA based, they can also be DNA based. Additionally, antisense oligonucleotides are often modified to increase their stability.

Without being bound by theory, the binding of these relatively short oligonucleotides to the mRNA of c-SRC kinase is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding the c-SRC kinase. Accordingly, antisense oligonucleotides decrease the expression and/or activity of the c-SRC kinase.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethylura-cil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetyl or analog thereof.

In yet a further embodiment, the antisense oligonucleotide is an -anomeric oligonucleotide. An -anomeric oligonucleotide forms specific double-stranded hybrids with complementary RNA in which, contrary to the usual -units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a c-SRC kinase, one of skill in the art can design antisense oligonucleotides that bind to the mRNA encoding the SRC-kinase, and test these oligonucleotides in an in vitro or in vivo system to confirm that they bind to and mediate the degradation of the mRNA encoding the particular protein. To design an antisense oligonucleotide that specifically binds to and mediates the degradation of the SRC-kinase, it is important that the sequence recognized by the oligonucleotide is unique or substantially unique to the SRC-kinase. For example, sequences that are frequently repeated across the SRC-kinase may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for the SRC-kinase.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive.

Such promoters include but are not limited to: the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

The c-SRC inhibitor can also include RNAi constructs that can specifically block expression of a c-SRC gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (I) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the c-SRC gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAI construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Examples of RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

The c-SRC inhibitors of the present invention can also include ribozymes molecules designed to catalytically cleave mRNA transcripts to prevent translation of mRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

The c-SRC kinase inhibitors can also include antibodies used as inhibitors of the activity of c-SRC kinase activity. Antibodies can have extraordinary affinity and specificity for particular epitopes. Antibodies that bind to a particular protein in such a way that the binding of the antibody to the epitope on the protein can interfere with the function of that protein. For example, an antibody may inhibit the function of the protein by sterically hindering the proper protein-protein interactions or occupying active sites. Alternatively, the binding of the antibody to an epitope on the particular protein may alter the conformation of that protein such that it is no longer able to properly function. Alternatively, the antibody may bind to a different site on the enzyme to sterically hinder the protein-protein interactions required for enzyme function. In still another example, the antibody may bind to a different site on the enzyme and alter the conformation of the enzyme such that the enzyme is no longer able to function.

Monoclonal or polyclonal antibodies can be made using standard protocols (See, for example, Antibodies: A Laboratory Manual ed. by Harlow and Lane (Cold Spring Harbor Press: 1988)). A mammal, such as a mouse, a hamster, a rat, a goat, or a rabbit can be immunized with an immunogenic form of the peptide. Techniques for conferring immunogenicity on a protein or peptide include conjugation to carriers or other techniques well known in the art.

Following immunization of an animal with an antigenic preparation of a polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a particular polypeptide and monoclonal antibodies isolated from a culture comprising such hybridoma cells.

In the context of the present invention, antibodies can be screened and tested to identify those antibodies that can inhibit the function of the SRC-kinase. One of skill in the art will recognize that not every antibody that is specifically immunoreactive with the SRC-kinase will interfere with the function of that protein. However, one of skill in the art can readily test antibodies to identify those that are capable of blocking the function of a particular protein.

The term antibody as used herein is intended to include fragments thereof which are also specifically reactive with a particular polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a particular protein conferred by at least one CDR region of the antibody.

Both monoclonal and polyclonal antibodies (Ab) directed against a particular polypeptides, and antibody fragments such as Fab, F(ab)$_2$, Fv and scFv can be used to block the action of a particular protein. Such antibodies can be used either in an experimental context to further understand the role of a particular protein in a biological process, or in a therapeutic context.

The present invention also relates to an agent that stimulates complex formation of $\alpha_v\beta_3$ integrin and VEGFR2 on endothelial cells expressing $\alpha_v\beta_3$ integrin and VEGFR2. It was found that angiogenesis of tissues can be increased, stimulated, or promoted by the administration of an agent that stimulates complexing of $\alpha_v\beta_3$ integrin and VEGFR2 (i.e, $\alpha_v\beta_3$ integrin/VEGFR2 complex stimulating agent). The term "stimulate", "stimulating" or "stimulant" includes any measurable reproducible increase in: speed, duration, or degree in the interaction of $\alpha_v\beta_3$ integrin and VEGFR2; angiogenesis; or any other activities complex formation of $\alpha_v\beta_3$ integrin and VEGFR2 may mediate.

A population of cells or tissue that express $\alpha_v\beta_3$ integrin and VEGFR2, such as endothelial cells, can be contacted with a therapeutically effective amount of a $\alpha_v\beta_3$ integrin/VEGFR2 complex stimulating agent under conditions effective to stimulate complex formation of $\alpha_v\beta_3$ integrin and VEGFR2. The stimulation of the complex formation of $\alpha_v\beta_3$ integrin and VEGFR2 can be used to increase angiogenesis in endothelial cells and promote angiogenesis in, for example, ischemic tissue. Additionally, the $\alpha_v\beta_3$ integrin/VEGFR2 complex stimulating agent can stimulate complex formation of $\alpha_v\beta_3$ integrin and VEGFR2 on cells stimulated not stimulated with VEGF or exposed to certain integrin ligands (e.g., vitronectin).

The stimulation of angiogenesis can play an important role in a variety of physiological processes such as embryonic development, wound healing, organ regeneration and female reproductive processes such as follicle development in the corpus luteum during ovulation and placental growth after pregnancy. Additionally, millions of patients per year in the U.S. suffer from myocardial infarction (MI) and/or critical limb ischemia. Many millions more suffer from related syndromes due to atherosclerosis. Many of these patients will benefit from the ability to stimulate angiogenesis in ischemic areas.

Where a composition is to be used for therapeutic purposes, the dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc.

In one aspect of the invention, the agent can comprise a stimulating compound or stimulating peptide that promotes complexing of $\alpha_v\beta_3$ integrin and VEGFR2. The stimulating peptide can have an amino acid sequence of about 5 to about 50 amino acids (e.g., about 10 to about 30 amino acids) that corresponds to an about 5 to about 50 amino acid portion of the amino acid sequence of the VEGFR2 or $\alpha_v\beta_3$ integrin. By corresponding to, it is meant the inhibiting peptide has an amino acid sequence with a sequence identity that is substantially homologous to a portion of the amino acid sequence of $\alpha_v\beta_3$ integrin or VEGFR2. By substantially homologous, it is meant the inhibiting peptide has at least about 70%, about 80%, about 90% or about 100% sequence identity with a portion of the amino acid sequence of $\alpha_v\beta_3$ integrin or VEGFR2.

In one example, the stimulating peptide can have an amino acid sequence identity of YGRKKRRQRRRGKEATSTFT-NITYpRGT-COOH (SEQ ID NO: 13) or KEATSTFTNI-TYpRGT-COOH (SEQ ID NO: 15). It was found that these peptides promote angiogenesis of epithelial cells expressing $\alpha_v\beta_3$ integrin and VEGFR2 both in the presence and the absence of VEGF.

The peptide in accordance with the present invention can be subject to various changes, substitutions, insertions, and deletions where such changes provide for certain advantages in its use. The peptide can be in any of a variety of forms of peptide derivatives, that include amides, conjugates with proteins, cyclized peptides, polymerized peptides, analogs, fragments, chemically modified peptides, and the like derivatives.

In another example, the $\alpha_v\beta_3$ integrin/VEGFR2 stimulating can comprise c-SRC kinase and/or an agent that up-regulates expression of the c-SRC kinase. It was found that $\alpha_v\beta_3$ integrin tyrosine phosphorylation is directly mediated by c-SRC kinase, which is able to phosphorylate the cytoplasmic domain of $\alpha_v\beta_3$. Thus, c-SRC via direct phosphorylation of $\alpha_v\beta_3$ integrin cytoplasmic motif controls functional association between $\alpha_v\beta_3$ and VEGFR2, which in turn regulates activation of both receptors on endothelial cells. The administration of c-SRC kinase an or agent that upregulates expression of c-SRC kinase to endothelial cells expressing $\alpha_v\beta_3$ and VEGFR2 can promote angiogenesis.

In another aspect, the $\alpha_v\beta_3$ integrin/VEGFR2 complex inhibiting/stimulating (i.e., modulating) agents in accordance with the present invention can be provided in a pharmaceutical compositions. The pharmaceutical compositions will generally comprise an effective amount of agent, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

In an aspect of the invention, the $\alpha_v\beta_3$ integrin/VEGFR2 complex modulating agents of the present invention can be formulated for parenteral administration, e.g., formulated for injection via the intravenous, intramuscular, sub-cutaneous, transdermal, intravitreal, or other such routes, including peristaltic administration and direct instillation into a tumor or disease site (intracavity administration). The preparation of an aqueous composition that contains such an $\alpha_v\beta_3$ integrin/VEGFR2 complex modulating agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms that can be used for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of the $\alpha_v\beta_3$ integrin/VEGFR2 complex modulating agents can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Examples of carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the $\alpha_v\beta_3$ integrin/VEGFR2 complex modulating agents can be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Examples of pharmaceutical compositions in accordance with the invention will generally include an amount of the $\alpha_v\beta_3$ integrin/VEGFR2 complex modulating agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

Formulations of the $\alpha_v\beta_3$ integrin/VEGFR2 complex modulating agents are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver $\alpha_v\beta_3$ integrin/VEGFR2 complex modulating agents in accordance with the present invention. The slow release formulations are typically implanted in the vicinity of the disease site, for example, at the site of a tumor.

Examples of sustained-release preparations include semipermeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773, 919; copolymers of L-glutamic acid and γ ethyl-L-glutamate; non-degradable ethylene-vinyl acetate; degradable lactic acid-glycolic acid copolymers, such as the Lupron Depot (injectable microspheres composed of lactic acid-glycolic acid copolymer and leuprolide acetate); and poly-D-(-)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the $\alpha_v\beta_3$ integrin/VEGFR2 complex modulating agents. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 µm, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

In an aspect of the invention, the $\alpha_v\beta_3$ integrin/VEGFR2 complex inhibiting agents may be advantageously employed in the preparation of pharmaceutical compositions suitable for use as ophthalmic solutions, including those for intravitreal and/or intracameral administration. For the treatment of any of the foregoing or other disorders a composition comprising $\alpha_v\beta_3$ integrin/VEGFR2 complex inhibiting agents of the invention can be administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation can contain the $\alpha_v\beta_3$ integrin/VEGFR2 complex inhibiting agents in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Examples of preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Examples of antioxidants and stabilizers include sodium bisulfite, sodium metabisulfite, sodium thiosulfite, thiourea and the like. Examples of wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

In another aspect, the $\alpha_v\beta_3$ integrin/VEGFR2 complex modulating agents can be formulated for topical administration. Topical formulations include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of $\alpha_v\beta_3$ integrin/VEGFR2 complex modulating agents for topical use, such as in creams, ointments and gels, includes the preparation of oleaginous or water-soluble ointment bases, as is well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

Local delivery via the nasal and respiratory routes is contemplated for treating various conditions. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Examples of formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 μm. Fine mists are produced by pressurized aerosols and hence their use in considered advantageous.

In accordance with another aspect of the present invention, the $\alpha_v\beta_3$ integrin/VEGFR2 complex inhibiting agents may be used to treat animals and patients with aberrant angiogenesis, such as that contributing to a variety of diseases and disorders. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Another example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stipulatory activity. VEGF expression in human coronary atherosclerotic lesions has been demonstrated. This evidences the pathophysiological significance of VEGF in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the present invention. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the present invention in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases.

The $\alpha_v\beta_3$ integrin/VEGFR2 complex inhibiting agents of the invention can also be utilized in the treatment of tumors. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs.

The $\alpha_v\beta_3$ integrin/VEGFR2 complex inhibiting agents provided by this invention are thus broadly applicable to the treatment of any malignant tumor having a vascular component. In using the $\alpha_v\beta_3$ integrin/VEGFR2 complex inhibiting agents of the invention in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using an anti-VEGF polypeptide.

Knowledge of the role of angiogenesis in the maintenance and metastasis of tumors has led to a prognostic indicator for cancers such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies of the present invention will reduce or negate the recurrence of such tumors.

The present invention is contemplated for use in the treatment of any patient that presents with a solid tumor. In light of the specific properties of the $\alpha_v\beta_3$ integrin/VEGFR2 complex inhibiting agents, the therapeutics of the present invention will have reduced side effects. Particular advantages will result in the maintenance or enhancement of host immune responses against the tumor, as mediated by macrophages, and in the lack of adverse effects on bone tissue. The invention will thus be the anti-angiogenic therapy of choice for the treatment of pediatric cancers and patients having, or at risk for developing, osteoporosis and other bone deficiencies.

Although all malignancies and solid tumors may be treated by the invention, the unconjugated polypeptides comprising $\alpha_v\beta_3$ integrin/VEGFR2 complex inhibiting agents are particularly contemplated for use in treating patients with more angiogenic tumors, or patients at risk for metastasis.

The present invention is also intended as a preventative or prophylactic treatment. These aspects of the invention include the ability of the invention to treat patients presenting with a primary tumor who may have metastatic tumors, or tumor cells in the earlier stages of metastatic tumor seeding. As an anti-angiogenic strategy, the present invention may also be used to prevent tumor development in subjects at moderate or high risk for developing a tumor, as based upon prognostic tests and/or close relatives suffering from a hereditary cancer.

Therapeutically effective doses of the $\alpha_v\beta_3$ integrin/VEGFR2 complex inhibiting agents are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors are widely used in pre-clinical testing.

In using the $\alpha_v\beta_3$ integrin/VEGFR2 complex inhibiting agents in anti-angiogenic therapies, one can also draw on other published data in order to assist in the formulation of doses for clinical treatment. For instance, although the agents and methods of the present invention have distinct advantages over those in the art, the information in the literature concerning treatment with other polypeptides and tyrosine kinase inhibitors can still be used in combination with the data and teaching in the present application to design and/or optimize treatment protocols and doses.

Any dose, or combined medicament of the $\alpha_v\beta_3$ integrin/VEGFR2 complex inhibiting agents, that results in any consistently detectable anti-angiogenic effect, inhibition of metastasis, tumor vasculature destruction, tumor thrombosis, necrosis and/or general anti-tumor effect will define a useful invention. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-angiogenic and/or tumor effects of the dose, or combined therapy of the $\alpha_v\beta_3$ integrin/VEGFR2 complex inhibiting agents, are towards the low end of the intended therapeutic range, it may be that this therapy is still equally or even more effective than all other known therapies in the context of the particular tumor target or patient. It is unfortunately evident to a clinician that certain tumors and conditions cannot be effectively treated in the intermediate or long term, but that does not negate the usefulness of the present therapy, particularly where it is at least about as effective as the other strategies generally proposed.

In designing appropriate doses of $\alpha_v\beta_3$ integrin/VEGFR2 complex inhibiting agents for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area ($m^2$) between the experimental animal and the human patient. All such calculations are well known and routine to those of ordinary skill in the art.

It will be understood that lower doses may be more appropriate in combination with other agents, and that high doses can still be tolerated.

The intention of the therapeutic regimens of the present invention is generally to produce significant anti-tumor effects while still keeping the dose below the levels associated with unacceptable toxicity. In addition to varying the dose itself, the administration regimen can also be adapted to optimize the treatment strategy. In administering the particular doses, one would preferably provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated.

Whether used for treating angiogenic diseases, such as arthritis, psoriasis, atherosclerosis, diabetic retinopathy, age-related macular degeneration, Grave's disease, vascular restenosis, hemangioma and neovascular glaucoma (or other diseases described above), or solid tumors, the present invention can be combined with other therapies.

The $\alpha_v\beta_3$ integrin/VEGFR2 complex inhibition based treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the polypeptides comprising $\alpha_v\beta_3$ integrin/VEGFR2 complex inhibiting based treatment, its combination with the present invention is contemplated.

In accordance with another aspect of the invention, methods of, and uses in, significantly inhibiting $\alpha_v\beta_3$ integrin and VEGFR2 complex formation without inhibiting natural ligand binding to $\alpha_v\beta_3$ integrin are provided. These methods comprise contacting, in the presence of VEGF, a population of cells or tissues that includes a population of endothelial cells that express VEGFR2 (KDR/Flk-1) and $\alpha_v\beta_3$ integrin with a composition comprising a biologically effective amount of at least one agent that inhibits tyrosine phosphorylation of $\alpha_v\beta_3$ integrin and/or VEGFR2.

Proliferation inhibition methods and uses are provided, including those to specifically inhibit VEGF-induced endothelial cell proliferation and/or migration, which generally comprise contacting a population of cells or tissues that includes a population of endothelial cells and VEGF with a composition comprising a biologically effective amount of the at least one $\alpha_v\beta_3$ integrin/VEGFR2 complex inhibiting agent under conditions effective to inhibit VEGF-induced endothelial cell proliferation and/or migration.

The foregoing methods and uses can be performed in vitro and in vivo. In the latter case the tissues or cells are located within an animal and the at least one $\alpha_v\beta_3$ integrin/VEGFR2 complex inhibiting agent is administered to the animal. In both cases, the methods and uses become methods and uses for inhibiting angiogenesis, comprising contacting a tissue comprising, or a population of, potentially angiogenic blood vessels, i.e., those potentially exposed to VEGF, with an anti-angiogenic composition comprising a biologically effective amount of the at least $\alpha_v\beta_3$ integrin/VEGFR2 complex inhibiting agent under conditions effective to inhibit angiogenesis.

Where populations of potentially angiogenic blood vessels are maintained ex vivo, the present invention has utility in drug discovery programs. In vitro screening assays, with reliable positive and negative controls, are useful as a first step in the development of drugs to inhibit or promote angiogenesis, as well as in the delineation of further information on the angiogenic process. Where the population of potentially angiogenic blood vessels is located within an animal or patient, the anti-angiogenic composition is administered to the animal as a form of therapy.

"Biologically effective amounts", in terms of each of the foregoing inhibitory methods are therefore amounts of the at least one $\alpha_v\beta_3$ integrin/VEGFR2 complex inhibiting agent effective to inhibit $\alpha_v\beta_3$ integrin and VEGFR2 complex formation without substantially inhibiting natural or native ligand binding to $\alpha_v\beta_3$ integrin.

The present invention thus further provides methods of, and uses in, treating a disease associated with angiogenesis, including all forms of cancer associated with angiogenesis, comprising administering to an animal or patient with such a disease or cancer a therapeutically effective amount of at least a first pharmaceutical composition that comprises at least $\alpha_v\beta_3$ integrin/VEGFR2 complex inhibiting agent.

The foregoing anti-angiogenic treatment methods and uses will generally involve the administration of the pharmaceutically effective composition to the animal or patient systemically, such as by transdermal, intramuscular, intravenous injection and the like. However, any route of administration that allows the therapeutic agent to localize to the angiogenic site or sites, including tumor or intratumoral vascular endothelial cells, will be acceptable. Therefore, other suitable routes of delivery include oral, rectal, nasal, topical, and vaginal. U.S. Pat. No. 5,712,291, is specifically incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the $\alpha_v\beta_3$ integrin/VEGFR2 complex inhibiting agent in an amount(s) and for a period of time(s) effective to exert anti-angiogenic and/or anti-tumor effects. The passive administration of proteinaceous therapeutics is generally preferred, in part, for its simplicity and reproducibility.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Integrin Phosphorylation and Signaling is Critical for VEGF-Induced Cellular Responses and Pathological Angiogenesis In Vivo We sought to directly establish the role of $\beta_3$ integrin tyrosine phosphorylation and integrin signaling in VEGF-stimulated responses of EC as well as in pathological angiogenesis in vivo. To this end, we knocked in a mutant form of $\beta_3$ integrin, in which both tyrosines 747 and 759 were substituted for phenylalanines ((DiYF $\beta_3$ integrin), instead of wild type in mice. In this study we combined in vivo and ex vivo angiogenesis assays with an extensive characterization of EC derived from both WT and DiYF mice in order to perform a complete analysis of the role of integrin $\beta_3$ and its signaling in functional responses to VEGF.

Results

Tyrosine Phosphorylation of $\beta_3$ Cytoplasmic Motif in EC Occurs Upon Adhesion to Integrin Ligands.

Figure 1:
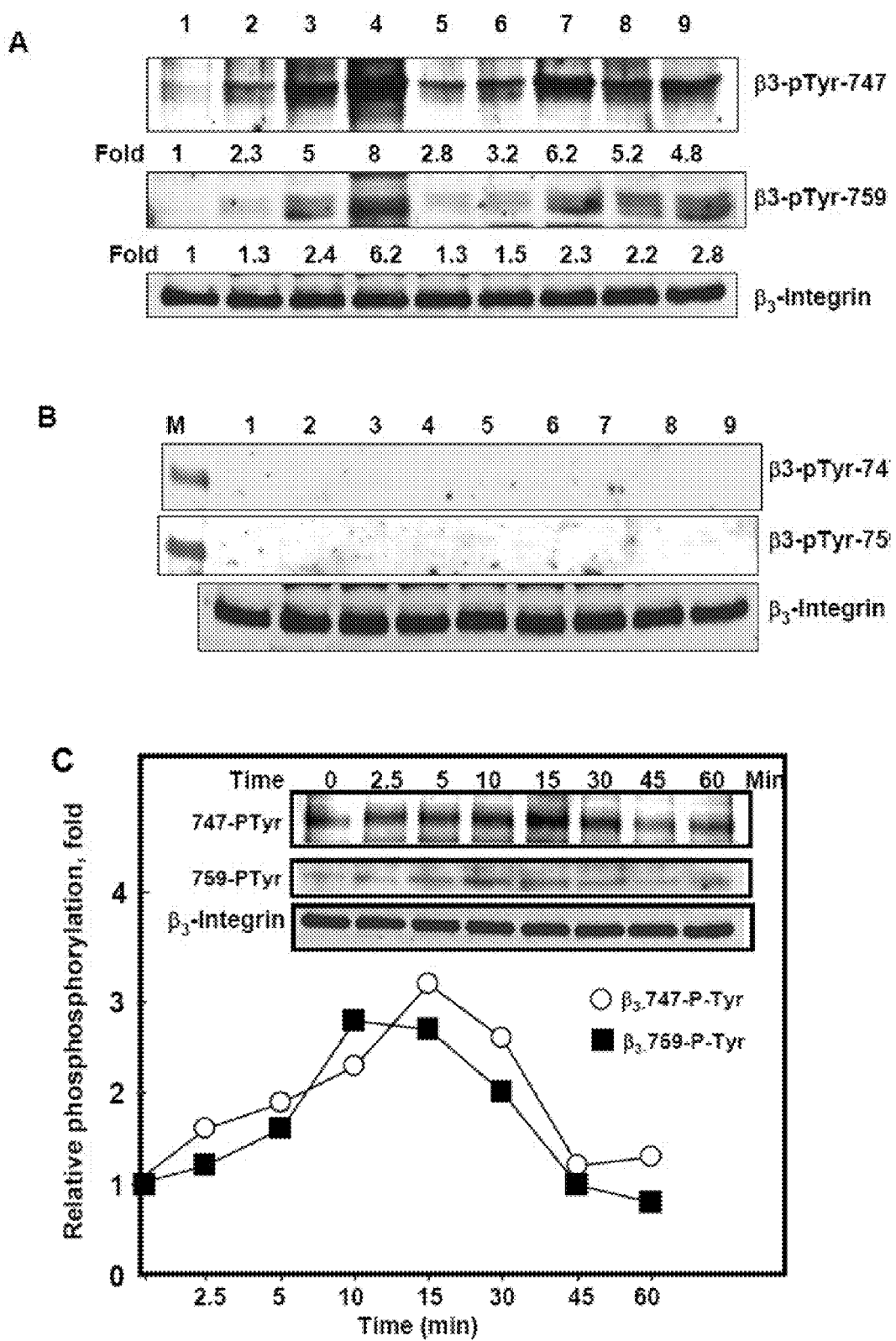
FIG. 1 illustrates extracellular matrix proteins and VEGF induce $\beta_3$ integrin cytoplasmic tyrosine motif phosphorylation. (A-B) $\beta_3$ integrin tyrosine phosphorylation upon adhesion to integrin ligands. Wild type (A) and DiYF (B) cells were either held in suspension (lane-1) or plated on poly-L-lysine (lane-2), gelatin (lane-3,4) with (lane 4) or without (lane 3) pervanadate treatment, laminin (lane-5), collagen (lane-6), vitronectin (lane-7), fibronectin (lane-8), fibrinogen (lane-9) and incubated at 37° C. for 60 mins. Cell lysates containing equal amount of protein were subjected to Western blot analysis using rabbit anti-integrin $\beta_3$ [pY$^{747}$] (upper panel A and B) and [pY$^{759}$] (middle panel A and B) antibody. Cell lysates were also analyzed for $\beta_3$ integrin expression as a loading control (lower panel A and B). (C) VEGF induces $\beta_3$ integrin tyrosine phosphorylation. WT and DiYF mouse lung EC were treated with 20 ng/ml of VEGF-A165 for 0 to 60 min as indicated. Phosphorylation status of $\beta_3$Y$^{747}$ (upper panel) and $\beta_3$ Y$^{759}$ (middle panel) was assessed as described in A. Amount of $\beta_3$ integrin in all samples is shown in lower panel.

Previous studies using model cell lines and platelets demonstrated that $\beta_3$ integrin cytoplasmic tyrosine phosphorylation is involved in outside-in integrin signaling. Therefore, we assessed whether EC adhesion to extracellular matrix proteins is able to induce beta 3 tyrosine phosphorylation. Accordingly, we isolated EC's from the lungs of wild type (WT) and DiYF mice, plated them on various substrates and assessed the phosphorylation of beta 3 on Tyr747 and Tyr459 (FIG. 1A). Very low levels of 747 as well as 759 $\beta_3$ phosphorylation were observed in cells kept in suspension or plated on the poly-lysine as a control substrate. Extracellular matrix proteins which serve as ligands for $\alpha_v\beta_3$ such as vitronectin, fibronectin, fibrinogen and gelatin strongly stimulated Tyr759 and Tyr747 phosphorylation. At the same time, laminin and collagen, which are recognized primarily not by integrins other than $\alpha_v\beta_3$ induced lower levels of tyrosine phosphorylation. Sodium pervanadate known to block phosphatase activity was used as a positive control in this experiment. As anticipated, no tyrosine phosphorylation of $\beta_3$ integrin was observed in DiYF EC under any conditions.

VEGF Treatment of EC Induces Tyrosine Phosphorylation of Beta 3.

The role of $\beta_3$ subunit phosphorylation in extracellular matrix recognition was previously assessed in model cell lines, such as CHO cells and K562 cells. This system does not provide any insight on the most important functions of the $\beta_3$ integrin, namely its role in angiogenesis and in the regulation of VEGF or FGF-induced EC responses. These processes can be only assessed in EC expressing appropriate receptors and signaling intermediates. Thus, we determined whether VEGF treatment is able to affect the phosphorylation status of $\beta_3$. Treatment of EC in suspension with VEGF-A165 induced Tyr747 as well as Tyr 759 phosphorylation of $\beta_3$ in a time-dependent manner. Both time curves of $\beta_3$ tyrosine phosphorylation followed a bell-shaped pattern which is typical for growth factor-induced responses. Thus, not only integrin engagement but also VEGF treatment in suspension stimulated tyrosine phosphorylation of $\beta_3$ subunit in EC, suggesting a possible regulatory role of this process in VEGF-induced angiogenesis.

Angiogenesis In Vivo is Impaired in DiYF Mice.

Thus, we determined whether $\beta_3$ integrin phosphorylation is crucial for a complete angiogenic response to VEGF in vivo. Accordingly, we implanted Matrigel containing VEGF-A subcutaneously into WT and DiYF mice and assessed angiogenic response based on the amount of hemoglobin extracted from Matrigel. As shown in FIG. 2A, hemoglobin concentration was at least 5 fold lower in Matrigel plugs isolated from DiYF mice compared to WT counterparts. The vascular density in Matrigel implants assessed by vWF staining was 4.2 fold lower in DiYF mice than in WT controls (p=0.01) (FIG. 2B). In Matrigel plugs from WT mice, large vWF-positive blood vessels were observed (FIG. 2C). In contrast, only 50% of Matrigel plugs from DiYF mice exhibited any staining for vWF and had a distinguishable vasculature (FIG. 2C). Thus, VEGF-induced angiogenesis was significantly impaired in DiYF mice.

Next, we assessed tumor-induced pathological angiogenesis in DiYF and WT mice. To this end, mouse melanoma cells were implanted subcutaneously into mice and 10 day after, tumors were excised. The vascular density in tumors grown in DiYF mice was 6 fold lower than that in WT mice (p=0.009) (FIG. 3A). Tissue section analysis revealed the presence of well-developed blood vessels which were positively stained for vWF, CD31 and laminin (basement membrane component) in tumors from WT mice. In contrast, in tumors formed in DiYF mice, blood vessels were sparse and thin-walled based on laminin staining (FIG. 3B). As a result of defective vascularization, the average weight of tumors formed in DiYF mice was at least 2 fold lower compared to WT (0.14 g vs 0.29 g) (FIGS. 3C and D). Thus, $\beta_3$ integrin phosphorylation plays a crucial role in the regulation of pathological angiogenesis in vivo.

DiYF Mutations within the $\beta_3$ Integrin Cytoplasmic Domain Impair Angiogenic Properties of EC.

Previous studies demonstrated that $\alpha_v\beta_3$ integrin controls cell growth rate, migration, invasive potential and angiogenic phenotype of EC. Therefore, we assessed whether impaired $\beta_3$ integrin tyrosine phosphorylation affects an ability of EC to form capillaries and tubes ex vivo. WT but not DiYF EC was able to form well-assembled and complete capillary cord-like structures in the presence of VEGF-A (FIG. 3A). In contrast, DiYF EC remained randomly scattered without any sings of organization (FIG. 4A). From FIG. 4B it is evident that the number of cords formed by WT EC was 5.4 fold higher compared to DiYF cells.

It is known that the major phenotypic characteristic of EC is its ability to assemble into the interconnected network of tube-like structures when grown in three dimensional matrix. WT but not DiYF EC formed clearly defined and well connected network of EC tubes (FIG. 4C). These structures were relatively stable and remained well-organized for at least 18 hours. As evident from FIG. 4C, DiYF EC were not able to complete the tube formation and no obvious pattern was formed even in the presence of VEGF. An extend of tube formation was quantified by measuring the length of tubes and mean values of three independent experiments are represented in FIG. 3 D. VEGF treatment induced about 3 fold increase in the length of the tubes formed by WT EC but had a little effect on DiYF EC.

Tyrosine Phosphorylation of $\beta_3$ Integrin Controls Ex Vivo Angiogenesis in Response to VEGF.

We next assessed whether DiYF mutations affected an outgrowth of vascular sprouts from aortic segments isolated from mice. First, ex vivo angiogenic assay was performed in Matrigel enriched with growth factors. It was evident that aortic rings from WT mice produced extensive network of vascular sprouts while DiYF aortic rings failed to do so (FIG. 4E). To elucidate the role of $\beta_3$ integrin in VEGF induced responses, aortic ring assay was performed in the presence or absence of VEGF using growth factor reduced Matrigel. Aortic rings from WT mice produced significantly higher number of vascular sprouts both in absence and presence of VEGF (FIG. 4F). The quantification of aortic ring sprouts revealed the ability of DiYF cells to form vascular sprouts ex vivo was at least 4 fold lower regardless of stimulation (FIG. 4G). VEGF produced a mild increase in capillary formation of DiYF rings, however, the number of sprouts was only 20-25% of that in WT aortic rings (FIG. 4G). To further analyze the capillary growth from aortic rings a detailed kinetic study was undertaken. The time curves of vascular growth are presented in FIG. 4H. In the absence of stimulation, a very few microvessels were detected in both WT and DiYF implants even after a prolonged incubation; where as serum-induced neovascularization was considerably higher in WT implants as compared to DiYF (FIG. 4H). The peak values of capillary growth were observed 8 days after implantation and were 10 and 45 microvessels per ring for DiYF and WT, respectively. VEGF served as a strongest stimulus and produced extensive formation of capillaries in WT but not in DiYF aortic rings (FIG. 4H). Taken together, these results indicate that the impaired pathological angiogenesis in DiYF mice was due to the defective functional responses of endothelial cells.

$\beta_3$ Integrin Cytoplasmic Domain Phosphorylation Regulates EC Adhesion, Spreading and Migration.

Next, in order to further define the nature of the angiogenic defect observed in DiYF mice, we compared angiogenesis-relevant functions of EC isolated from WT and DiYF mice. We first assessed whether the mutation in $\beta_3$ integrin cytoplasmic domain had any effect on EC adhesion and subsequent cell spreading on extracellular matrix substrates. To this end, WT and DiYF EC were plated on various integrin ligands and numbers of attached and spread cells per field were counted. WT and DiYF EC adhered and spread equally well on fibronectin, laminin-1 and collagen coated plates (FIGS. 5A and B). In contrast, a significant difference in the behavior of WT and DiYF EC was found using $\alpha_v\beta_3$ ligand, vitronectin. On this substrate, DiYF EC showed a 2 fold reduction in adhesion and a 4 fold decrease in the number of spread cells (FIGS. 5A and B). Next, we compared migration of WT and DiYF EC towards various extracellular matrix proteins known to be recognized by integrins. Similar to the results of adhesion assays, WT and DiYF EC migrated equally well towards fibronectin, laminin and collagen but not towards vitronectin, where a 3 fold reduction in migration of DiYF EC versus WT was observed (FIG. 5C).

Then, we compared a VEGF-induced migratory activity of WT and DiYF EC. Stimulation of WT EC with VEGF at 5, 10 and 20 ng/ml induced 1.5, 2.5 and 2.9 fold increases of migration compared to untreated EC (FIG. 5D). DiYF EC also responded to VEGF stimulation, however, the rate of migration was substantially reduced (FIG. 5D). Thus, tyrosine phosphorylation of $\alpha_v\beta_3$ integrin appears to play an important role in VEGF-induced EC migration to extracellular matrix. To further confirm these results, we utilized an alternative and more physiologically relevant method to assess EC migration. WT and DiYF EC were plated on various integrin ligands and were allowed to form a confluent monolayer. Then, a wound in the monolayer was created and the healing process was monitored at different time points. The quantitative aspects of wound recovery and representative images of EC are presented in FIGS. 5E and 5F, respectively. Where as WT and DiYF EC migrated equally well on fibronectin, laminin and collagen, a 3 fold reduction in migration on vitronectin was observed in DiYF EC compared to WT (FIG. 5E). Moreover, using live video microscopy, the process of EC migration and wound recovery was carefully monitored in order to characterize differences in cell movement between WT and DiYF EC (See supplemental data). Thus, it appears that DiYF mutation impairs $\alpha_v\beta_3$ integrin-dependent and VEGF-stimulated responses of EC indicating its potential role in the regulation of a cross-talk between $\alpha_v\beta_3$ and VEGF receptor(s).

$\beta_3$ Integrin Phosphorylation is Required for Sustained Activation of VEGF Receptor-2.

Next, we sought to identify a molecular mechanism responsible for abnormalities observed in DiYF EC. Previous studies using $\beta_3$ null mice demonstrated that the absence of $\beta_3$ leads to upregulation of VEGFR-2 and consequently to augmentation of angiogenic responses of EC. However, no differences in VEGFR-2 levels were observed between DiYF and WT EC of lung as well as of aortic origin (not shown). It was previously shown that integrin $\beta_3$ is able to form a complex with VEGFR-2 immediately upon stimulation with VEGF, and this association was proposed to be necessary for the activation of angiogenic program in EC. Therefore, we sought to determine whether DiYF mutations impaired an ability of $\beta_3$ integrin to interact with VEGFR-2. Low levels of $\beta_3$-VEGFR2 interactions were observed in nonstimulated WT EC in suspension or upon adhesion to extracellular matrix. VEGF stimulated a dramatic increase in a complex formation between $\beta_3$ and VEGFR-2 in WT EC plated on vitronectin, but not in suspension or on laminin, demonstrating a ligand specificity of this phenomenon. In contrast, no interaction between $\beta_3$ and VEGFR2 was observed in DiYF EC under any conditions. Thus, it appears that $\beta_3$ tyrosine phosphorylation is essential for an interaction between VEGFR-2 and $\alpha_v\beta_3$ integrin. In order to further investigate the mechanism of $\beta_3$ integrin-dependent VEGF signaling, we performed a detailed comparison of VEGFR-2 phosphorylation status in response to VEGF in WT and DiYF EC. A time course of VEGFR2 phosphorylation is presented in FIG. 6C. In WT EC, VEGF induced a bell-shaped response with a maximum 6 fold increase in VEGFR-2 phosphorylation over control. After 45 min, VEGFR-2 phosphorylation returned to the control levels. In contrast, VEGF exerted much lower increase in VEGFR-2 phosphorylation in DiYF EC with the maximum value of 2.5 fold over control. Importantly, VEGFR-2 in WT EC remained phosphorylated 3 times longer than in DiYF EC (FIG. 6C). Thus, the lack of integrin phosphorylation in DiYF EC resulted in reduced phosphorylation/activation of VEGFR-2 in response to VEGF, which, in turn, affected all the signaling events downstream of VEGFR-2.

Tyrosine Phosphorylation is Critical for VEGF-Induced $\alpha_v\beta_3$ Integrin Activation An intrinsic property of integrins is an increased soluble ligand binding in response to stimulation, a process referred to as integrin activation. We and others previously reported that VEGF via VEGFR-2 is able to activate $\alpha_v\beta_3$ integrin on EC. Accordingly, we sought to determine whether impaired activation of VEGFR-2 in DiYF EC results in defective $\alpha_v\beta_3$ activation by VEGF. VEGF induced at least 6 fold increase of fibrinogen binding to WT EC and only 3 fold increase of binding to DiYF EC (FIG. 6D). $MnCl_2$, an agonist known to activate integrins and at the same time to stimulate $\beta_3$ integrin tyrosine phosphorylation, produced at least 40 fold increase in fibrinogen binding to WT EC, compared to 17 fold increase observed in DiYF EC (FIG. 6E). The specificity of ligand binding was conformed by addition of 10 fold excess of unlabelled fibrinogen. Similar results were observed when integrin activation was monitored using a monovalent activation-dependent ligand WOW-1 Fab. VEGF and $MnCl_2$ stimulated 9 and 30 fold increases, respectively, in WOW-1 binding to WT EC and 3.5 and 14 fold increases, respectively, to DiYF EC (FIGS. 6F and 6G). Thus, it is apparent that DiYF mutations within the cytoplasmic domain of $\beta_3$ integrin significantly impair the process of integrin activation, which, in turn, results in defective cell adhesion and migration.

Discussion

To investigate the role played by $\beta_3$ integrin in pathological angiogenesis, we replaced a WT $\beta_3$ integrin in mice with its mutated form that is unable to undergo phosphorylation and, therefore, defective in signaling abilities (knockin mice). The major advantage of this experimental approach is the utilization of a new model that allows monitoring $\alpha_v\beta_3$ function in a context of angiogenesis in primary EC and not in model cell lines lacking appropriate receptors and signaling intermediates. This is a reason why our ex vivo and in vitro results provide novel information, which is somewhat distinct from the previously published results of in vitro studies and also from the observations in $\beta_3$ knockout mice. In DiYF EC $\beta_3$ integrin is present on the surface at the normal level; however, its function has been modified by the mutations. Thus, the second unique aspect of our experimental system is the lack of compensatory or over-compensatory responses, which are often observed in knockout models when the protein of interest, is absent during development. As discussed below in detail, the knockin technique seems to be more physiologically relevant and more direct compared to the knockout approach. Moreover, this particular technique is the most appropriate for the multifunctional proteins involved in various signaling pathways since it allows focusing on the certain function of the protein, in our case on the role of tyrosine phosphorylation without disturbing other aspects of $\beta_3$ integrin activity.

Using DiYF knockin mice, we assessed angiogenesis in vivo as well as performed an extensive analysis of the underlying mechanisms using numerous ex vivo models and the major findings of this manuscript are the following: 1) Phosphorylation of $\beta_3$ integrin in WT EC occurs in response to integrin ligation as well as VEGF stimulation; 2) Lack of $\beta_3$ integrin phosphorylation in DiYF knockin mice results in impaired angiogenic response and reduced tumor growth in vivo; 3) VEGF-induced functional responses of EC from DiYF mice (cell adhesion, spreading, migration and capillary tube formation) are defective compared to WT; 4) Lack of $\beta_3$ integrin phosphorylation in DiYF knockin EC leads to disruption of VEGFR-2/$\beta_3$ integrin complex formation and causes a deficiency of VEGFR-2 phosphorylation in response to VEGF; 5) VEGF-induced integrin activation (inside-out signaling) is suppressed in DiYF EC compared to WT.

Our data suggest that $\beta_3$ integrin is a positive regulator of angiogenesis and its phosphorylation is a critical step in EC responses during VEGF-induced neovascularization. Further, our findings provide an additional argument that increased angiogenesis observed in $\beta_3$ knockout mice is a result of molecular compensation via VEGFR2, which emphasizes a physiological importance of VEGFR2-$\alpha_v\beta_3$ cross-regulation in EC, but does not reflect a true function of $\alpha_v\beta_3$ integrin in angiogenesis in a context of an organism expressing normal amounts of this receptor. Since our experimental approach does not involve a complete deletion of $\beta_3$ integrin from the cell surface, it does not trigger compensatory responses, i.e. upregulation of VEGFR2 in EC. The phenomenon of molecular compensation or in many cases, over-compensation in knockout mice has been described in numerous reports and represents a major drawback of the knockout approach.

In the present study, impaired angiogenesis in DiYF knockin mice was traced to the defective functions of EC since in a series of ex-vivo assays the capillary formation induced by VEGF was abnormal in DiYF EC. At the cellular level, this defect resulted from the decreased cell adhesion, spreading and migration in response to VEGF. Interestingly, impaired cell adhesion and migration was observed only on vitronectin as a substrate but not on fibronectin or collagen. Nevertheless, ex vivo angiogenesis in Matrigel as well as in vivo angiogenesis was defective, which emphasizes a role of $\alpha_v\beta_3$ in this process.

At the molecular level, this study demonstrates that impaired tyrosine phosphorylation in DiYF EC abrogates $\alpha_v\beta_3$/VEGFR-2 complex formation and results in dramatically reduced phosphorylation of VEGFR-2 upon VEGF stimulation. Since VEGF (via VEGFR-2 as its major functional receptor on EC) induces phosphorylation of $\alpha_v\beta_3$, and phosphorylation of $\alpha_v\beta_3$, in turn, is required for complete and sustained phosphorylation of VEGFR-2, it can be concluded that these two receptors are able to cross-activate each other in EC, therefore, forming a functional partnership that is essential for successful angiogenesis.

Materials and Methods

Animals

DiYF mice were generated in the laboratory of Dr. David R. Phillips and maintained on C57/Bl6 background (7 generations of backcrossing). Six to eight week old wild-type (WT) and DiYF mice were used in study.

Primary Lung Endothelial Cell Isolation

Wild type and DiYF mouse lungs were excised, minced and digested using collagenase-dispase reagent (3 mg/ml). Digests were strained and the resulting cell suspension was plated on flasks coated with 1 mg/ml fibronectin. Endothelial cells were isolated and characterized.

Aortic Ring Assay

Thoracic aortas from WT and DiYF mice were removed under aseptic conditions and spliced into 1 mm thick rings. Thoracic aortic rings were placed between two layers of growth factor depleted Matrigel and allowed to solidify at room temperature. Matrigels were overlaid with either with DMEM or endothelial growth medium with or without VEGF (40 ng/ml). Microvessel outgrowth was visualized by phase contrast microscopy and numbers of vessels growing from each aortic ring were counted and photographed every two days using Leica phase contrast microscope.

Cell Adhesion and Cell Spreading Assay

Mouse lung endothelial cells were detached from the tissue culture flasks using 20 mM EDTA. Cells were washed twice with sterile PBS and re-suspended in DMEM. The cell suspensions were added to ligand-coated wells and placed in humidified incubator for 45 min. The wells were gently washed three times with DMEM and photographs were taken. The numbers of attached and spread cells per field were counted.

Cell Migration Assay

Transwell tissue culture inserts were coated with various integrin ligands for 24 h at 4° C. Both WT and DiYF lung endothelial cells were trypsinized and $1\times10^5$ cells were added into each well. The lower chamber contained varying concentrations of VEGF-A165 (0-20 ng/ml). Cells were allowed to migrate for 12 h and fixed with 3.7% formaldehyde/PBS for 15 min and stained with 0.5% crystal violet. The non-migrated cells adhered to the top surface were removed and three random 10× fields were photographed using Leica inverted phase contrast microscope.

Endothelial Wound Healing Assay

WT and DiYF mouse lung endothelial cells were grown to confluence in 12 well plates precoated with various integrin ligands. Cells were serum starved for 4 h and then a wound was created by a 1000 µl pipette tip. Wells were rinsed twice with sterile PBS to remove wound-derived loose and dislodged cells and further cultured DMEM medium containing 2% FBS. Images were recorded immediately after wounding (time zero) and 12 h later. Cell migration was quantified using image analysis of 5 randomly selected fields of denuded area. The mean wound area is expressed as percent of recovery (% R) from three identically treated plates using the equation % $R=[1-(T/T_0)]\times100$, where: $T_0$ is the wounded area at 0 h and $T_t$ is the wounded area after 12 h.

Fibrinogen Binding Assay

To assess fibrinogen binding, semiconfluent wild type and DiYF mouse lung endothelial cells were serum starved for 4 h and further induced with 20 ng/ml VEGF-165, 20 ng/ml b-FGF or 1 mm MnCl2. Fluorescein isothiocyanate (FITC)-labeled fibrinogen was added at a final concentration of 200 nM for 45 min. Cells were fixed with 3.7% formaldehyde/PBS for 15 min and washed twice with ice-cold 1×PBS. Fluorescence-activated cell sorting (FACS) was performed using a FACS Calibur (Becton Dickinson, San Jose, Calif.) and data were analyzed using CellQuest software program.

WOW-1 Binding Assay

Wild type and DiYF mouse lung endothelial cells were serum starved for 4 h and further stimulated with 20 ng/ml VEGF-165, 20 ng/ml b-FGF or 1 mm MnCl2 separately. WoW-1 Fab was added at a final concentration of 30 mg/ml, followed by addition of Fluorescein isothiocyanate (FITC) conjugated goat anti-mouse IgG at 10 µg/ml. After 30 min cells were fixed with 3.7% formaldehyde/PBS for 15 min, washed twice with 1×PBS and FACS was performed using a FACS Calibur (Becton Dickinson, San Jose, Calif.) instrument and data were analyzed using CellQuest software program.

Precapillary Cord Formation Assay

Wild type and DiYF mouse lung endothelial cells were trypsinized and washed twice with DMEM containing 10% FCS. These cells were seeded on Matrigel coated 6 well plate and cells were allowed to adhere. After 24 h, the medium was removed and cells were overlaid with 0.5 ml of Matrigel containing 40 ng/ml VEGF. All the wells were filled with 2 ml of endothelial growth medium and cells were observed and photographed every day using Leica phase contrast microscope.

Tube Formation Assay

The formation of vascular tube-like structures by wild type and DiYF mouse lung endothelial cells were assessed on the basement membrane matrix preparation. Six well plates were coated with 0.5 ml of Matrigel according to the manufacturer's instructions. Wild type and DiYF mouse lung endothelial cells were detached from the tissue culture flasks using 20 mM EDTA. Cells were washed twice with sterile 1×PBS and seeded on Matrigel coated plate. Medium was supplemented with or without 20 ng/ml VEGF and further incubated at 37° C. for 8 h. The tube formation was observed using an inverted phase contrast microscope (Leica) and photographs were taken from each well. Using ImagePro software, the degree of tube formation was quantified by measuring the length of tubes in random fields.

Immunoprecipitation and Western Blot Analysis

Semiconfluent endothelial cells grown on various integrin substrates were made quiescent by 4 h starvation in serum free DMEM medium. Cells were lysed in a 50 mM Tris-HCl buffer pH 7.4, containing 150 mM NaCl, 1% Triton X-100, and protease and phosphatase inhibitors. Cell lysates were cleared by centrifugation (10000 gx for 10 mins) and further incubated with rabbit polyclonal anti-b3 integrin antibody for 3 h at 4° C. and immune complexes were recovered using protein A-agarose. Immunoprecipitates were washed two times with lysis buffer, twice with high salt buffer and twice with no salt buffer. Integrin immune complexes from agarose beads samples were boiled for 5 min in SDS-PAGE sample buffer. Immunocomplexes were resolved by SDS-PAGE (6%), and transferred to nitrocellulose membrane. These blots were probed with anti-VEGFR-2 and anti-b3 integrin antibody respectively. Proteins were detected using enhanced chemiluminescence technique (Amersham).

To analyse the $\beta_3$ integrin tyrosine phosphorylation wild type and DiYF mouse lung microvascular endothelial cells suspended in various integrin ligand coated plates and further incubated at 37° C. for 60 mins. Cells were lysed and cell lysates containing equal amount of protein were subjected to Western blot analysis using rabbit anti-integrin $\beta_3$ [$pY^{747}$] and [$pY^{759}$] antibody. Cell lysates were also analyzed for $\beta_3$ integrin expression as a loading control.

Serum starved wild type and DiYF endothelial cells were also treated with 20 ng/ml VEGF for 0-60 mins. Cell lysates were analyzed by Western blot using anti-integrin $\beta_3$ [pY$^{747}$], anti-integrin [pY$^{759}$], anti-p-VEGFR-2, anti-VEGFR-2, anti-p-ERK1/2, anti-ERK1/2, anti-p-Akt, anti-Akt, anti-p-P38MAPK and anti-MAPK antibody. The wild type and DiYF endothelial cells were lysed and equal proteins from total cell lysates were subjected SDS-PAGS and analyzed by western blot using anti-VEGFR-2 and anti-CD-31 antibody.

Statistical Analysis

Values were expressed as mean plus or minus standard deviations (SD). P values were based on the paired t test. All the experiments were repeated at least 3 or more times unless indicated otherwise. Results were considered statically significant with P value less than 0.05.

Example 2

Integrin Affinity Modulation in Angiogenesis

The aim of this study was to assess the role of each individual subfamily of integrin receptors in VEGF-induced angiogenic cellular responses using a siRNA-based short-term knockdown approach in primary endothelial cells.

Experimental

Materials

Rabbit polyclonal anti-VEGFR-2, anti-β3-integrin, anti-β5-integrin, antiβ1-integrin, mouse monoclonal anti-phospho tyrosine (PY20 and PY99) antibodies, and β1, β3, and β5 integrin-specific siRNAs were purchased from Santa Cruz Biotechnology, Inc. (Santa Cruz, Calif.). Anti-VEGFR-2 and anti-phospho VEGFR-2 were from Cell Signaling Technology (Beverly, Mass.). Mouse monoclonal anti-β3-integrin blocking antibody was from Chemicon International Inc. (Temecula, Calif.). Anti-CD31 antibody was obtained from DAKO (Kyoto, Japan). Mouse monoclonal anti-β3-integrin activating antibodies were generated in our laboratory. Purified collagen, laminin, vitronectin, and VEGF were purchased from R&D Systems (Minneapolis, Minn.). Matrigel was obtained from BD Biosciences (San Jose, Calif.). The HUVEC nucleofector kit was obtained from Amaxa Biosystems (Gaithersburg, Md.). Alexa 488 conjugated goat anti-rabbit, goat anti-mouse IgG, and TRITC-conjugated goat anti-rabbit IgG were from Invitrogen (Carlsbad, Calif.). Purified WOW-1 Fab was provided by Dr. S. J. Shattil, The Scripps Research Institute, La Jolla, Calif. All other chemicals were analytical grade.

Cell Culture and Transfection

Human umbilical cord vein endothelial cells (HUVEC) cells were grown in Dulbecco's modified Eagle's medium (DMEM) supplemented with supplemented with 10% FBS, 90 μg/mL heparin sulphate, 90 μg/mL endothelial cell growth factor, 100 U/mL penicillin, 100 μg/mL streptomycin. Cells were used for the experiment between second and fifth passages. HUVECs were transiently transfected using the HUVEC nucleofector kit according to the manufacturer's instructions. Forty-eight hr after transfection, cells were serum starved and used for experiments. Cell surface expressions of integrins were detected as described previously.

Cell Adhesion Assay

HUVECs were detached from the tissue culture flasks using 20 mM EDTA. Cells were washed twice with sterile phosphate buffered saline (PBS) and re-suspended in serum-free DMEN. The cell suspensions were added to integrin ligand-coated wells and placed in a humidified incubator for 45 min. The wells were gently washed three times with DMEM and photographs were taken. The numbers of attached and spread cells per field were counted.

Endothelial Wound Healing Assay

HUVECs were grown to confluence in 12 well plates pre-coated with various integrin ligands. Cells were serum starved for 4 h and then a wound was created by a pipette tip. Wells were rinsed twice with sterile PBS to remove wound-derived loose and dislodged cells and further cultured in DMEM medium containing 2% FBS. Images were recorded immediately after wounding (time zero) and 12 h later. Cell migration was quantified using image analysis of five randomly selected fields of denuded area. The mean wound area is expressed as percent of recovery (% R) from three identically treated plates using the equation % R=[1−(Tt/T0)]×100, where T0 is the wounded area at 0 h and Tt is the wounded area after 12 h.

WOW-1 Binding Assay

Semiconfluent HUVECs were serum starved for 4 h and further stimulated with 20 ng/mL VEGF-A165 or VEGFDΔ-NΔC. WOW-1 Fab was added to a final concentration of 30 μg/mL, followed by addition of FITC-conjugated goat anti-mouse IgG at 10 μg/mL. After 30 min cells were fixed with 3.7% formaldehyde in PBS for 15 min, washed twice with PBS, and fluorescence-activated cell sorting (FACS) was performed using a FACS Calibur (Becton Dickinson, San Jose, Calif.) and data were analyzed using CellQuest software.

Tube Formation Assay

The formation of vascular tube-like structures by HUVECs was assessed on a basement membrane matrix preparation. Twelve-well plates were coated with 0.5 mL of Matrigel according to the manufacturer's instructions. HUVECs transfected with various β integrin-specific siRNAs. Cells were detached from tissue culture flasks using 20 mM EDTA in PBS. Cells were washed twice with sterile PBS and seeded on Matrigel-coated plates. Medium with or without 20 ng/mL VEGF was added and cells were further incubated at 37° C. for 8 h. The tube formation was observed using an inverted phase contrast microscope (Leica, Wetzlar, Germany) and photographs were taken. Using ImagePro software (Media Cybernetics, Silver Spring, Md.), the degree of tube formation was quantified by measuring the length of tubes in three random fields.

Immunohistochemistry and Immunocytochemistry Analysis

To study integrin activation status, HUVECs were grown in monolayer on glass slides and then treated with 1 mM MnCl$_2$ or 20 ng/mL VEGF for 10 min. These cells were further incubated with WOW-1 antibody for additional 30 min. These cells were fixed with paraformaldehyde for 10 min, blocked with 5% bovine serum albumin for 30 min, and incubated with FITC-conjugated anti-mouse IgG. These cells were washed, mounted with coverslips, and analyzed under a florescent microscope (Leica). Alternatively, cells were further incubated with anti-VEGFR-2 antibody and incubated with TRITC-conjugated anti-rabbit IgG. These cells were washed, mounted, and analyzed under confocal microscopy (Leica).

Western Blot Analysis

HUVECs were lysed following the experiment using lysis buffer (50 mM Tris-HCl (pH 7.4), 150 mM NaCl, 1% Nonidet P-40, 1% Triton X-100, 1% sodium deoxycholate, 0.1% SDS, 5 mM iodoacetamide, 2 mM phenylmethylsulfonyl fluoride, 2 mM EDTA, 10 mM NaF, 10 mM Na2P2O7, 10 μg/mL leupeptin, 4 μg/mL pepstatin, and 0.1 units/mL aprotinin). Cell lysates were centrifuged at 13,000×g for 10 min at 4° C. Supernatants were collected and assayed for protein concentration using the Bio-Rad protein assay method (Hercules, Calif.). Cell lysates were denatured using Laemmli sample buffer and proteins were separated by sodium dodecyl sulphate polyacrylamide gel electrophoresis and probed with indicated antibody. When appropriate, nitrocellulose membranes were stripped and blotted according to manufacturer's instructions.

Results

Silencing Effects of siRNA on Expression of Integrins in Endothelial Cells

We utilized small interfering RNAs (siRNAs) to down regulate expression of 1 subunits of various integrin heterodimers in primary EC. Upon transfection of EC with specific siRNAs, significant down-regulation of β1, β3, and β5 subunit expressions was achieved as evidenced by results of Western blotting analysis (FIGS. 7A, B, and C). Quantitative analysis revealed that the expression of β1, β3 and β5 integrins was down-regulated by 75, 70, and 80%, respectively, whereas the control siRNA did not show any effect on expression of any of the integrins tested (FIG. 7A, B, C). Cell surface expression of β1, β3, and β5 integrins following siRNA transfection were conformed by FACS analysis. Results revealed that transfection of HUVECs with specific siRNAs resulted in 74, 65, and 76% decreases in surface expression of β1, β3, and β5 integrins, respectively (FIG. 7D, E, F). Each siRNA was specific for its respective β subunit, since siRNAs did not affect expression levels of other subunits (not shown). These results conclusively indicated that siRNAs down-regulated the total expression, as well as cell surface levels, of specific β integrins in endothelial cells.

Cell Adhesion Profiling of EC Lacking β1, β3 and β5 Integrin Subunits.

Adhesion of endothelial cells to extracellular matrix (ECM) components through cell surface integrins are known to required for endothelial cell growth, differentiation, and survival. Endothelial cell adhesion to ECM induces cellular proliferation and programmed cell death of non-adherent cells in suspension. Integrin ligand ligation induces a wide variety of intracellular signaling, including tyrosine phosphorylation of FAK, increased inositol lipid synthesis, cyclin synthesis, and expression of several cell survival factors. Endothelial cell surface integrins mediate adhesion to ECM proteins, including vitronectin, laminin, collagen, von Willebrand factor, and fibrinogen. To examine endothelial cell adhesion to various ECM proteins following inhibition of expression of specific integrin subunits, HUVECs transfected with integrin-specific siRNA were plated on various integrin ligand coated plates and ability of EC to adhere to the distinct extracellular matrix components were tested. Representative images and quantitative results are shown in FIGS. 8A and 8B, respectively. Inhibition of expression of the β1 subunit abolished EC adhesion to both collagen and laminin, but not to vitronectin. Silencing of the β3 subunit completely inhibited EC adhesion to vitronectin, but not to collagen or laminin. Inhibition of expression of the β5 subunit only partially (~50%) inhibited cell attachment to vitronectin and had no substantial effect on adhesion to other tested extracellular matrix components. These observations indicated that sister integrins did not functionally compensate after expression of a specific integrin was silenced in HUVECs.

Vitronectin (αvβ3) and Collagen (α5β1) Receptors Modulate Endothelial Cell Migration.

Extracellular matrix provides critical support for proliferating vascular endothelium through adhesive interaction with endothelial cell surface integrins. Extracellular matrix also provides the scaffold essential for maintaining the organization of vascular endothelial cells in to blood vessels. Endothelial cell adhesion to extracellular matrix is required for endothelial cell proliferation, migration, and morphogenesis. Integrin-mediated migration of endothelial cells also plays a crucial role in vascular remodeling involved in angiogenesis, embryonic vasculogenesis, and re-endothelialization in arteries following angioplasty. To examine which of the endothelial integrins trigger endothelial cell migration, HUVECs were transfected with various β-integrin specific siRNAs and these cells were plated on various extracellular matrix components. A wound was created across the cell monolayer by scraping away a swath of cells and the extent of wound healing due to the transfected EC was measured after 12 hours. Representative images are shown in FIG. 9A. Percentages of wound recovery were quantified (FIG. 9B). Control EC were able to completely close the wound on vitronectin and was assigned value of 100%. EC plated on collagen and laminin shown 85% and 30% recovery respectively. EC transfected with siRNA targeting the β1 subunit were almost completely unable to heal wounds on collagen, but were not substantially different from control EC on vitronectin and laminin. Silencing of β3 and β5 subunits diminished wound recovery on vitronectin by 50 and 30%, respectively, without any effect on collagen and laminin. The results of these assays demonstrate that the critical integrin subunits for regulation of endothelial cell communication with extracellular matrix are β3 and β1. As above, no compensatory effects were observed.

αvβ3 Integrin is Crucial for Endothelial Cell Morphogenesis.

During angiogenesis, proliferating and migrating endothelial cells organize to form three-dimensional capillary networks. This processes initiates with transition of endothelial cells into spindle-shaped morphology. This is followed by endothelium alignment and connection into solid, multicellular, precapillary cord-like structures that form an integrated polygonal network. During this vascular morphogenesis, extracellular matrix serves as an adhesive support and, through interaction with integrins, provides crucial signaling to regulate endothelial cell shape and contractility. To examine which integrin is crucial during endothelial cell morphogenesis, HUVECs were transfected with various β-integrin specific siRNAs and angiogenic properties of EC were assessed using a capillary tube formation assay on Matrigel. Capillary tube forming ability of unstimulated as well as VEGF-stimulated cells was tested. Silencing of the β1 subunit affected capillary formation in the absence as well as in the presence of VEGF. As shown in FIG. 10A, the regularity of the typical honeycomb-like pattern was disturbed resulting in incomplete connections between cellular cords. Among three different siRNA transfections, knockdown of the β3 subunit produced the most severe inhibitory effect on capillary growth; silencing of β3 completely abolished the formation of cellular cords by these EC both in the absence and presence of VEGF (FIG. 10A). Down regulation of β5 integrin subunit substantially, but not completely, impaired capillary growth of unstimulated EC and, to a lesser extent, of VEGF-stimulated cells. Quantitative aspects of capillary growth of all three EC lines are shown in FIG. 10B. Thus, it appears that knockdown of β3 subunit was the most effective in inhibiting angiogenic response in vitro. Therefore, we further focused on β3 integrin which forms a complex exclusively with αV subunit on EC to produce $\alpha_v\beta_3$ heterodimer.

$\alpha_v\beta_3$ Integrin Affinity Modulation and Association with VEGFR-2.

Integrin affinity relates to conformational modification in the integrin heterodimer to strength of ligand binding. Usually non-integrin receptors cause alterations in the integrin cytoplasmic domain ultimately modulating integrin activation state. Several receptor tyrosine kinases (RTKs), G-protein coupled receptors, and cytokines have been shown to modulate integrin activation state. To study the synergism between $\alpha_v\beta_3$ integrin and RTKs such as VEGFR-2 on endothelial cell surface, HUVECs were induced with VEGF and integrin affinity was estimated. A genetically engineered antibody WOW-1 was used as a probe to detect $\alpha_v\beta_3$ in the high affinity state on the surface of EC in the monolayer. WOW-1 Fab is a monomeric soluble ligand which binds only to the activated form of $\alpha_v\beta_3$. Stimulation with VEGF-A165 increased WOW-1 binding to EC by 6-fold compared to resting cells as measured by FACS analysis (FIG. 11A). Importantly, the mature form of VEGF-D, VEGF-DΔNΔC, known to be specific for VEGFR-2 on EC of blood vessel origin, was also potent inducer of WOW-1 Fab binding, indicating that VEGFR-2 but not VEGFR-1 is primarily receptor mediating $\alpha_v\beta_3$ integrin activation.

The results of WOW-1 binding to HUVECs in a pre-confluent monolayer in response to VEGF-A165, VEGF-DΔNΔC, or $Mn^{2+}$ are shown in FIG. 11B. All treatments induced WOW-1 binding and binding was most evident at the cellular borders. To further investigate whether activated $\alpha_v\beta_3$ integrin forms a complex with VEGFR-2, HUVECs were induced with VEGF and stained with WOW-1 and VEGFR-2 antibody. Surprisingly on VEGF-stimulated EC, activated $\alpha_v\beta_3$ co-localized with VEGFR-2 on cell borders (FIG. 11C). Thus, our results establish that VEGFR-2-dependent activation of $\alpha_v\beta_3$ integrin leads to macromolecular interaction between $\alpha_v\beta_3$ integrin and the VEGF receptor-2 in endothelial cells.

Activated αVβ3 Integrin is Index for Enhanced Tumor Vasculature.

To further emphasize whether αvβ3 integrin interact with VEGFR-2 on endothelial cells of proliferating blood vessel, we have selected biopsy specimens of human prostate carcinomas that express high expression of VEGF. Triple staining of serial tissue sections of the prostate tumors with WOW-1 antibodies (to localize activated $\alpha_v\beta_3$), with Abs against CD31 (to identify EC), and with Abs against VEGFR-2 (to localize VEGFR-2) was used (FIG. 12A). As in the in vitro studies presented above, activated αVβ3 co-localized with VEGFR-2 in vasculature of prostate carcinomas (FIG. 12A). The distribution of VEGFR-2 and WOW-1 staining was virtually identical in most of carcinoma samples (FIG. 12B). This result clearly indicated that activated αvβ3 integrin physically associated with VEGFR-2 on endothelial cells of proliferating blood vessels.

Next, we performed WOW-1 staining of normal prostate tissues to compare to prostate carcinomas. Based on CD31 staining, the prostate carcinoma tissue is characterized by 6-fold increase in vascular density compared to normal tissue (FIGS. 12 C and D). The vessels of normal prostate tissue were poorly stained with the WOW-1 antibody, whereas prostate tumor vessels were clearly WOW-1-positive, suggesting that activation of $\alpha_v\beta_3$ might serve as a marker of pathological angiogenesis. Quantification of WOW-1 density revealed a 2.7-fold increase in $\alpha_v\beta_3$ activation in prostate carcinomas compared to normal prostate tissues (FIG. 12E). Thus, quantification of $\alpha_v\beta_3$ integrin could be used as index for tumor angiogenesis. Thus, our in vivo analyses provide evidence that $\alpha_v\beta_3$ is activated on EC at sites of angiogenesis. Co-localization of activated $\alpha_v\beta_3$ with VEGFR-2 indicates a possible cross-talk between these receptors not only in vitro but also in vivo.

VEGFR-2/β3 Integrin Cross-Talk in EC.

It was reported that knockouts of β3 and β5 subunits in mice resulted in upregulation of the expression level of VEGFR-2 on EC. However, as shown in FIGS. 13 A, B, and C, silencing of expression of β1, β3, or β5 integrin using siRNA had no effect on VEGFR-2 levels in EC. Thus, it is most likely that upregulation of VEGFR-2 in β3-null mice occurs during development as a compensatory mechanism due to the result of prolonged down-regulation of $\alpha_v\beta_3$ integrin. We also assessed how inhibition of expression of β subunits affected VEGFR-2 activation in EC. In control EC, treatment with VEGF induced substantial phosphorylation of VEGFR-2 (FIG. 14D). This response was not affected by silencing of β1 integrin (FIG. 14D). In contrast, ablation of β3 expression by a specific siRNA resulted in ~3-fold decrease of VEGFR-2 phosphorylation in response to VEGF. Silencing of the β5 subunit resulted in a modest decrease of phosphorylation VEGFR-2 (FIG. 14 D). Thus, it appears that β3, but not β1 or β5, integrin influenced VEGFR-2 activation on EC.

Next, we assessed whether activation of $\alpha_v\beta_3$ by externally added activating antibodies influenced activation of VEGFR-2 in response to VEGF. As shown in FIG. 14E, three different β3-specific activating antibodies, LIBS-1, AP-7.3, and CRC-54, augmented VEGFR-2 phosphorylation in VEGF-treated EC. In contrast, antibodies that blocked $\alpha_v\beta_3$ provided 2-fold inhibition of VEGFR-2 phosphorylation. Thus, not only expression but also activity of $\alpha_v\beta_3$ integrin appears to control VEGF-induced phosphorylation of VEGFR-2, demonstrating a functional cross-talk between these two receptors.

Discussion

This study aimed to assess the regulatory functions of individual β subunits of major endothelial cell surface integrins in VEGF-induced angiogenic responses. The major findings of this analysis are as follows: 1) Silencing of expression of individual β subunits resulted in downregulation of EC adhesion and migration on the corresponding primary ligand, while no effects on the recognition of other ligands were detected. 2) Among the three β subunits expressed on EC, loss of β3 had the most dramatic inhibitory effect on capillary growth of EC in response to VEGF. 3) $\alpha_v\beta_3$ activation triggered by VEGF/VEGFR-2 was detected in EC suspension as well as in a monolayer; on the monolayer activated αVβ3 was co-localized with VEGFR-2. 4) In vivo, activated $\alpha_v\beta_3$ co-localized with VEGFR-2 on endothelium. 5) Activation of $\alpha_v\beta_3$ in vivo was substantially increased in highly vascularized tumors as compared to normal tissues. 6) Silencing of expression of β1, β3, or β5 in EC did not affect expression levels of VEGFR-2. However, inhibition of expression of β3, but not β1 or β5, resulted in inhibition of VEGFR-2 phosphorylation in response to VEGF. 7) Exogenous activation of $\alpha_v\beta_3$ integrin stimulated, and blockade inhibited, VEGF-dependent phosphorylation of VEGFR-2. Together, these results show the prominent role of $\alpha_v\beta_3$ integrin in the functional cross-talk with VEGF/VEGFR-2 in a context of angiogenic endothelial functions.

Endothelial cells express a relatively wide range of integrin receptors, which permits interactions with numerous extracellular matrix ligands. Although the ligand recognition profile of each integrin is rather unique, there is a significant degree of redundancy and functional overlap. This is a case for $\alpha_v\beta_3$ and $\alpha_v\beta_5$, since both integrins are considered as primary receptors for vitronectin. However, our data indicate that of the several integrin receptors on EC, including $\alpha_v\beta_3$ has a distinct function in angiogenesis, which cannot be compensated by other integrins. First, affinity of $\alpha_v\beta_3$ on EC can be rapidly modulated by the treatment with VEGF, resulting in increased adhesive and migratory responses of EC. Importantly, we were able to document that $\alpha_v\beta_3$ is activated in endothelium of highly vascularized tumor as compared to normal tissues. Second, the pro-angiogenic role of $\alpha_v\beta_3$ integrin is not limited to interactions with vitronectin and other substrates; it is tightly linked to its ability to augment activation of VEGFR-2. We demonstrated that activated $\alpha_v\beta_3$ is co-localized with VEGFR-2 not only in cultured EC, but also on endothelial cells of proliferating blood vessels at the sites of pathological angiogenesis. Several other studies have indicated the unique nature of association between these two receptors. The functional consequences of such association are of supreme importance, since VEGFR-2 mediates the majority of VEGF-induced responses, including EC proliferation, migration, and permeability. The key role of the VEGF/VEGFR-2 system in angiogenesis is also underscored by the severe impairment of vasculature development leading to early embryonic lethality in mice lacking either of those genes. Thus, it appears that the ability of αVβ3 to regulate VEGFR-2 function makes this integrin a key player in VEGF-induced responses of endothelial cells.

Indeed, it has been previously demonstrated that the blockade of αVβ3 integrin with monoclonal antibodies or ligand antagonists leads to blunted blood vessel formation in the context of several models of pathological angiogenesis, including cancer, arthritis, and ischemic retinopathy. However, vascular development appears to be normal in mice lacking either αV or β3 integrins and pathological angiogenesis is enhanced in β3, β5, or β3/β5 null mice. The major difference between the siRNA-based knockdown approach used in our study and genetic ablation in knockout animals is centered on the transient nature of siRNA-based silencing versus permanent and complete loss of protein expression in development. If the function of targeted protein cannot be spared during development, such loss will ultimately result in embryonic lethality. In contrast to its prominent role in development, VEGF does not seem to be absolutely required for normal physiology of adult organisms, since neutralization of circulating VEGF has proven safe in patients. Likewise, based on results of β3 knockout, this integrin is not likely to be a crucial player during development but it does mediate pathological neovascularization in adults. Thus, it is not surprising that its loss does not cause lethality but rather triggers compensatory up-regulation of other pro-angiogenic molecules. Moreover, the lack of involvement of β3 in normal development and physiology makes it very attractive therapeutic target for a number of diseases.

We demonstrated that $\alpha_v\beta_3$ integrin on EC exists and functions as a part of a complex with VEGFR-2. We predict that the physical loss of one part of this complex might provoke up-regulation of its other part. It is possible that the physical presence of $\alpha_v\beta_3$ on the EC surface might also function to bind and sequester signaling molecules and otherwise enhance VEGFR-2-stimulated responses. Our data, in conjunction with the results of β3 knockout studies, emphasize the intimate connection between $\alpha_v\beta_3$ and VEGFR-2. The differential consequences of short term vs. long-term inhibition of $\alpha_v\beta_3$ may have relevance for pathological angiogenesis treatments with $\alpha_v\beta_3$ inhibitors as prolonged therapy may trigger the same compensatory responses observed in β3 null mice, leading to treatment failure.

Example 3

Method

Angiogenesis Assay in Matrigel

Experimental Details

The effect of $\alpha_v\beta_3$/VEGFR2 complex inhibiting peptides in accordance with the present invention on angiogenic function was assessed by tube formation assay on the basement membrane matrix preparation. Six well plates were coated with 0.5 mL of Matrigel according to the manufacturer's instructions. HUVECs (Human Umbilical vascular endothelial cells) were detached from the tissue culture flasks using 20 mM EDTA. Cells were washed twice with sterile PBS and seeded on Matrigel-coated plates in combination of presence/absence of VEGF and inhibitory peptide. Cells were further incubated at 37° C. for 8 h. The tube formation was observed using an inverted phase contrast microscope (Leica) and photographs were taken from each well. Using ImagePro software, the degree of tube formation was quantified by measuring the length of tubes in random fields.

FIG. 14 illustrates (A) photographs of endothelial cell tube formation in a matrigel assay for endothelials cells subjected to VEGF, a peptide in accordance with the present invention, and VEGF in conjunction with a peptide in accordance with the present invention; and (B) a graph showing the results.

Results

The results were indicated that VEGF induced the endothelial cell tube formation by at least 450 μm/mm². Treatment of endothelial cells with these peptides also inhibited the tube formation at least by 50%. Even upon induction with VEGF treatment. These data clearly indicate that pre-phosphorylated beta 3 integrin cytoplasmic peptide prevent VEGF induced endothelial tube formation in vitro.

Comparative Example

Data showing the phosphorylation status of beta 3 integrin upon LM609 treatment (original antibody used to create vitaxin) is indicated in FIG. 15. Phosphorylation of beta 3 depends on the complex formation (this is a functional readout). If phosphorylation still occurs, beta 3 integrin can still send a signal (in other words, the receptor is still operational). At the same time, its binding ability is completely blocked. Thus, we monitor integrin function at the different level. This set of data means that LM609 (vitaxin) blocks only ligand binding but not signaling. Comparison of this data with DiYF shows that phosphorylation occurs in response to VEGF and is a prerequisite for complex formation. One more time: complex formation and phosphorylation of beta 3 are inter-dependent events.

HUVEC cells were serum starved for 3 hours and further incubated with these antibodies for 2 hours at room temperature. Cells were induced with 20 ng/ml VEGF for 5 mins and analyzed for phosphorylation of beta3 integrin by Western blot analysis.

Example 4

Methods

Matrigel plug assays were performed in age- and sex-matched C57/Bl6 background mice. Each animal received an abdominal subcutaneous injection of 500 μL Matrigel mixed with VEGF (60 ng/mL), heparin (60 units/mL) and 50 mM of control (YGRKKRRQRRR G DTANNPL FKEATSTFT-COOH) (SEQ ID NO: 14) or beta-3 integrin cytoplasmic domain inhibitory peptide (YGRKKRRQRRRG DTANNPL Yp KEATSTFT-COOH) (SEQ ID NO: 2). After 7 days, the animals were euthanized and dissected. Matrigel plugs were removed and digested using 5 mL Drabkin reagent and neovascularization was assessed using a hemoglobin assay as per the manufacturer's protocol (FIG. 16).

Results

To examine the effect of beta-3 integrin cytoplasmic domain inhibitory peptide on angiogenesis we subcutaneously implanted VEGF-A-containing Matrigel with either 50 mM of control peptide (YGRKKRRQRRR G DTANNPL FKEATSTFT-COOH) (SEQ ID NO: 14) or with equal amount of beta-3 integrin cytoplasmic domain inhibitory peptide (YGRKKRRQRRR G DTANNPL Yp KEATSTFT-COOH) (SEQ ID NO: 2). Angiogenic response was measured based on the amount of hemoglobin extracted from Matrigel. As shown in FIG. 17, the hemoglobin concentration was at least 3.5 fold lower in Matrigel plugs treated with beta-3 integrin cytoplasmic domain inhibitory peptide compared to control peptide containing Matrigel.

Example 5

Additive Roles of Integrin on VEGF Receptor-2 Activation and Angiogenesis

The cross-activation of integrin and growth factor receptors at the cell surface appears to influence numerous intracellular signaling pathways, which, in turn, regulate the critical events, such as endothelial cell proliferation and apoptosis. The cross-activation process between integrin and growth factor receptors is "upstream" of all events triggered by any of these receptor systems. Surprisingly, this phenomenon has not been thoroughly studied and there are critical gaps in our understanding of molecular mechanisms underlying the process of receptor cross-activation.

Results $\beta$3 Integrin Tyrosine Phosphorylation is Induced in Endothelial Cell Adherent to Vitronectin and is Required for Maximum Tyrosine Phosphorylation of VEGFR-2.

As a first step to examine the relationship between integrin ligation, $\beta$3 integrin cytoplasmic tyrosine motifs phosphorylation and VEGFR-2 activation, we monitored phosphorylation of $\beta$3 at Tyr-747 and Tyr-759 in EC plated on the $\alpha_v\beta_3$ integrin ligand, vitronectin, or $\alpha2\beta1$ integrin ligand, collagen, or $\alpha6\beta1/\alpha6\beta4$ integrin ligand, laminin. As a control, the EC were maintained in suspension in the presence or absence of VEGF stimulation. As shown in FIG. 18A, vitronectin but not laminin or collagen was able to induce $\beta$3 integrin tyrosine phosphorylation, which was augmented upon VEGF treatment. At the same time, phosphorylation of $\beta$3 integrin was minimal in cells in suspension or plated on laminin or collagen despite the stimulation with VEGF (FIG. 18A). Analysis of VEGFR-2 phosphorylation at Tyr-1175 in the same set of samples revealed that basal level of VEGFR-2 activation can be triggered by $\alpha v\beta3$ integrin ligation by vitronectin but does not occur in cells plated on $\alpha2\beta1$ integrin ligand (collagen) or $\alpha6\beta1/\alpha6\beta4$ integrin ligand (laminin). Thus, while VEGF stimulation promotes phosphorylation of $\alpha v\beta3$ integrin, ligation of $\alpha v\beta3$ also stimulates VEGFR-2 phosphorylation and activation demonstrating a mutual relationship between VEGFR2 and $\alpha v\beta3$.

$\beta$3 Integrin Tyrosine Phosphorylation is Complementary for VEGF Induced Tyrosine Phosphorylation of VEGFR-2.

$\alpha v\beta3$ integrin is expressed on proliferating endothelial cells during angiogenesis and vascular remodeling and the blockade of $\alpha_v\beta_3$ integrin suppressed angiogenesis in several in vivo models. Therefore, we assessed whether the blockade of $\alpha v\beta3$ affected tyrosine phosphorylation of $\beta$3 subunit. Accordingly, HUVECs grown on gelatin coated plates were serum starved and further incubated with 10 μg/mL anti-$\alpha v$, anti-$\beta3$, anti-$\beta1$, anti-$\beta5$ blocking antibodies at 4° C. for 2 hours. Cells were also treated with non-immune IgG as control. These cells were washed and further induced with VEGF for 5 min at 37° C. Cell lysates were analyzed for phosphorylation of $\beta$3 integrin (Tyr-747 and 759). FIG. 18B shows that both anti-$\alpha v$ and anti-$\beta3$ blocking antibodies inhibited VEGF induced tyrosine phosphorylation of $\beta$3 integrin at both tyrosine-747 and tyrosine759. At the same time, control IgG, anti-$\beta1$ or anti-$\beta5$ blocking antibody did not have substantial effect on VEGF-induced tyrosine phosphorylation of $\beta$3 integrin. Basal level of $\beta$3 integrin tyrosine phosphorylation remains unaffected irrespective of different blocking antibody treatment. To further examine consequences of $\alpha v\beta3$ integrin blocking antibodies, cell lysates were analyzed for tyrosine phosphorylation of VEGFR-2 (Tyr-1175). Results indicated that only anti-$\alpha v$ and anti-$\beta3$ functional blocking antibodies suppressed VEGF induced tyrosine phosphorylation of VEGFR-2, whereas anti-$\beta1$ or anti-$\beta5$ blocking antibodies did not had any effect on VEGF induced activation of VEGFR-2 (FIG. 18 panel C). Further, treatment of HUVECs with VEGFR-2 inhibitor significantly reduced VEGF induced $\beta$3 integrin cytoplasmic tyrosine residue phosphorylation (FIG. 18 panel D). Taken together, these results demonstrate that there is a cross-activation between two receptors: $\alpha v\beta3$ integrin ligation controls not only tyrosine phosphorylation of the $\beta$3 subunit but also of VEGFR-2, and VEGF stimulation promotes not only VEGFR2 but also $\beta$3 integrin tyrosine phosphorylation.

As VEGFR-2 activation and signaling seems to be tightly associated with integrins, we intend to examine interaction of VEGFR-2 with various integrin on endothelial cell surface. Accordingly serum starved HUVECs were induced with VEGF for 5 min and cell lysates were immunoprecipitated with rabbit-antiVEGFR-2 antibody and immunoblotted with anti-integrin $\beta1$, anti-integrin $\beta3$ and anti-integrin $\beta5$ antibody as they are major $\beta$-integrins on endothelial cell surface. Results indicate that endothelial cells challenged with VEGF induced interaction of VEGFR-2 with $\beta$3 integrin (FIG. 18 panel E). Small fraction of VEGFR-2 also found to interact with $\beta$1 integrin but not with $\beta$5 integrin. VEGF induction did not enhanced interaction between VEGFR-2 and $\beta$1/$\beta$5 integrins under these conditions. Thus, it appears that out of three classes of integrins expressed on endothelial cells, only $\alpha v\beta3$ integrin forms a complex with VEGFR2 upon VEGF treatment.

VEGF Differentially Induces Interaction of Src Family Tyrosine Kinases (SFKs) with $\beta$3 Integrin in Endothelial Cells.

$\beta$ subunit of integrin heterodimers are known to associate with Src family tyrosine kinases (SFKs) and are required for early consequences of integrin signaling. Presence of SFKs is critical for the tyrosine phosphorylation of several intracellular signaling molecules following the integrin mediated cell adhesion and cell spreading. Therefore, we sought to analyze the degree of different SFKs interaction with $\beta$3 integrin and VEGFR-2 upon stimulation of endothelial cells with VEGF. Accordingly, HUVECs were induced with VEGF for 10 min and cell lysates were split in to two parts and immunoprecipitated with anti-$\beta3$ integrin and anti-VEGFR-2 antibody separately using ProFound co-immunoprecipitation kit. In resting EC, only small amounts of c-Src associated with both VEGFR-2 and $\beta$3 integrin. VEGF stimulation dramatically enhanced interaction of c-Src with VEGFR-2 and $\beta$3 integrin. No basal level or VEGF induced interaction was found between Fyn and $\beta$3 integrin or VEGFR-2. Moderate amount of Yes was always associated with $\beta$3 integrin and VEGFR-2, even after VEGF induction Yes interaction with either $\beta$3 integrin or VEGFR-2 did not altered significantly (FIG. 19 panel A and B). Therefore, we concluded that c-Src is a major tyrosine kinase associated with β3 integrin following stimulation of cells with growth factor and, therefore, might be a kinase responsible for phosphorylation of β3 integrin cytoplasmic tyrosine motifs. To further conform these observation kinetic analysis of β3 integrin and c-Src tyrosine phosphorylation were performed. VEGF induced tyrosine phosphorylation of β3 integrin at 2.5 min and remain phosphorylated up to 30 min. Maximum level of β3 integrin tyrosine phosphorylation was observed between 5 min to 15 min. VEGF also induced similar pattern of activation phosphorylation of c-Src in endothelial cells (FIG. 19 panel C). These observations let us consider activated c-Src might be directly or indirectly responsible for β3 integrin phosphorylation, which, in turn, is crucial for activation of β3 integrin dependent cellular signaling and endothelial cell functions.

Adhesion and Growth Factor Induced β3 Integrin Tyrosine Phosphorylation is Mediated through c-Src.

Cytoplasmic domains of integrin β subunits are highly conserved and represents region of structural homology between the various groups. Cytoplasmic tail consists of a membrane proximal sequence that forms an amphipathic helix and distal well conserved sequences, NPXY and NXXY that comprise tight beta turns. These regions have been linked to the ability of integrin to localize to focal contacts, FAK phosphorylation, ligand binding affinity, integrin dependent actin cytoskeletal reorganization, cellular adhesion and spreading. Therefore, we sought to examine the role of c-Src in adhesion and growth factor induced tyrosine phosphorylation of β3 integrin. Accordingly HUVECs cells were either kept in suspension (FIG. 20, panel A, lane-1) or plated on vitronectin (lane-2) and then treated with VEGF (lane-3) or c-Src inhibitor SU6656 (lane-4). Cell lysates were analyzed for the phosphorylation of β3 integrin. As anticipated, in comparison to HUVEC kept in suspension, cells plated on vitronectin showed high level of β3 integrin tyrosine phosphorylation at Tyr-747 and Tyr-759 which was further augmented by VEGF. Treatment of adherent endothelial cells with c-Src specific inhibitor SU6656 completely blocked β3 integrin tyrosine phosphorylation. As an independent approach, HUVEC were transfected with wild type (WT Src), dominant negative (DN Src) and catalytically active (CA Src) forms of Src. Cells transfected with dominant negative Src shown severe impairment in adhesion as well as VEGF failed to induce β3 integrin tyrosine phosphorylation (lane 5 and 6). In contrast, expression of catalytically active c-Src (CA Src) dramatically enhanced adhesion as well as VEGF-induced tyrosine phosphorylation of β3 integrin on both Tyr-747 and Tyr-759 residues (lane 9 and 10). Transfection of HUVECs with wild type c-Src did not significantly alter adhesion or VEGF induced β3 integrin tyrosine phosphorylation (lane 7 and 8).

To further substantiate the specific role of c-Src in β3-integrin tyrosine phosphorylation, we endeavor cellular system in which c-Src expression is highly regulated. Src++ cell line was derived from control mouse embryo, expresses endogenous wild type c-Src but lack the expression of Yes and Fyn kinases. SYF fibroblasts cell line was derived from c-Src, Fyn, and Yes triple knockout embryos and showed that integrin dependent signaling is dramatically impaired in these cells (28). SYF+c-Src cell line was generated by reintroducing wild type c-Src in SYF cells using retroviral vector pLXSH. As shown in FIG. 20B, no β3 integrin tyrosine phosphorylation was observed in any of these cell types plated on uncoated plastic surface or kept in suspension (lane 2 and 3). Attachment to vitronectin stimulated high level of β3 integrin tyrosine phosphorylation in Src++ and SYF+c-Src cells but not in SYF cells (lane 4). Cells plated on laminin or collagen shown very low β3 integrin tyrosine phosphorylation (lane 5). Upon growth factor stimulation, β3 integrin tyrosine phosphorylation was observed only in Src++ and SYF+c-Src cells but not in SYF-cells (FIG. 20 C). Thus, c-Src controls cell adhesion as well as VEGF induced β3 integrin tyrosine phosphorylation.

c-Src Directly Phosphorylates Cytoplasmic Tyrosine Motifs of β3 Integrin.

Principle mechanism by which integrins appear to mediate the transfer of information from extracellular environment to intracellular milieu is through phosphorylation of β-subunit at cytoplasmic tyrosine motifs. Ligand occupancy of αvβ3 is a prerequisite for the tyrosine phosphorylation events and implying an important role for outside-in integrin signaling in this process. To examine whether c-Src can directly mediate β3 integrin tyrosine phosphorylation, c-Src was immunoprecipitated from VEGF-stimulated HUVEC. Immunocomplex were incubated with a full-length purified β3 integrin cytoplasmic domain, and [$\gamma$-$^{32}$P] ATP incorporation into was monitored. As shown in FIG. 20D, the immunoprecipitated c-Src can phosphorylate β3 integrin cytoplasmic domain (lane 2). The specific inhibitor of c-Src SU6656 blocked this process, confirming the specificity of the reaction (lane 3). Recombinant protein tyrosine phosphatase also prevented phosphorylation, indicating that it is a tyrosine substrate that is being phosphorylated (lane 4). Recombinant purified c-Src also phosphorylated the β3 integrin whereas no phosphorylation was observed without the substrate, indicating the specificity of the reaction (lane 1 and 5). Together, these results clearly show that c-Src can directly phosphorylate cytoplasmic tyrosines of β3 integrin. To further investigate whether c-Src phosphorylates Tyr-747 or Tyr-759 of β3 integrin or both residues, kinase assay were performed using peptide derived from these two distinct sites of β3 integrin as substrates (FIG. 20 E). Pharmacological inhibitor of c-Src (SU6656), which blocks c-Src autophosphorylation, was used to demonstrate the specificity of the reaction. In the absence of integrin substrate, significant amount of c-Src autophosphorylation was observed indicating that c-Src immunocomplex is active. In the presence of Tyr-747/Tyr-759 β3 integrin cytoplasmic peptide, a dramatic increase in [$\gamma$-$^{32}$P] ATP incorporation was observed as compared to control peptides devoid of tyrosine motifs. Similar results were observed using purified recombinant c-Src protein. As anticipated, [$\gamma$-$^{32}$P] ATP incorporation was minimal in the presence of purified recombinant protein tyrosine phosphatase, indicating that the role of c-Src in phosphorylation of tyrosine residues. Together, these results clearly indicated that c-Src directly phosphorylates both tyrosine motifs (747/759) of β3 integrin cytoplasmic tail.

c-Src Mediated β3 Integrin Tyrosine Phosphorylation is Critical for VEGF Induced VEGFR-2-β3 Integrin Macromolecular Complex Formation.

Our previous results indicates that VEGF induced VEGFR-2 tyrosine phosphorylation was maximum in cell plated on only αvβ3-integrin ligand vitronectin. Only αv and β3 integrin functional blocking antibodies able to block VEGF induced VEGFR-2 tyrosine phosphorylation and VEGFR-2 show maximum interaction with β3 integrin in endothelial cells. As a next step, we sought to examine the role of Src-mediated β3 integrin phosphorylation in β3 integrin interaction with VEGFR-2. Accordingly, c-Src activity was modified by over expression of wild type, dominant negative or catalytically active form of Src or by treatment of cells with Src and VEGFR-2 inhibitors and then, interaction between VEGFR2 and β3 integrin was assessed. In non-stimulated cells, no interaction between β3 integrin and VEGFR-2 was observed (FIGS. 21A and B, Lane 1), whereas VEGF induced strong interaction between VEGFR-2 and β3 integrin (lane-2). Treatment of cells with pharmacological inhibitors of c-Src and VEGFR2 known to inhibit β3 integrin tyrosine phosphorylation prevented VEGF-stimulated interaction between β3 and VEGFR-2 (lane 3 and 4). Likewise, transfection with dominant negative Src reduced and catalytically active Src enhanced interaction between two receptors (lane 6 and 7). These results indicated that degree of tyrosine phosphorylation of β3 integrin essentially regulate interaction between the β3 integrin and VEGFR-2 in endothelial cells.

To further analyze the role of β3 integrin cytoplasmic tyrosine motifs in β3 integrin and VEGFR-2 interaction, we utilized lung EC derived from a β3 knock-in mouse in which Tyr747 and Tyr759 were mutated phenylalanines (DiYF). The cytoplasmic domain of DiYF integrin is unable to undergo phosphorylation, resulting in deficient integrin signaling. FIG. 21C shows that VEGF induced phosphorylation of β3 integrin at Tyr-747 and Tyr-759 in wild type but not in DiYF EC. To further assesses role of c-Src-mediated β3 integrin tyrosine phosphorylation in β3 integrin interaction with VEGFR-2, wild type and DiYF endothelial cells were transfected with dominant negative or catalytically active form of Src and interaction between VEGFR2 and β3 integrin was examined. VEGF induced interaction between β3 integrin and VEGFR-2 was observed only in wild type cells (FIG. 21D Lane-3) and in un-stimulated cells, no interaction found between β3 integrin and VEGFR-2 (Lane-2). Transfection of dominant negative Src diminished and catalytically active Src enhanced interaction between β3 integrin and VEGFR-2 only in wild type cells (lane 4 and 5). Under any of these conditions no interaction were found between β3 integrin and VEGFR-2 in DiYF cells. These results clearly demonstrate that c-Src mediated tyrosine phosphorylation of β3 integrin controls VEGF induced β3 integrin and VEGFR-2 interaction in endothelial cells.

c-Src is Critical for Growth Factor Induced β3 Integrin Activation and Ligand Binding An intrinsic property of integrin is an increase in soluble ligand binding in response to stimulation, a process referred to as integrin activation. Our results indicated that c-Src directly phosphorylates β3 integrin on cytoplasmic tyrosine motifs which, in turn, might affect integrin functional activity. To address this issue, HUVECs were transfected with wild type, dominant negative and catalytically active form of c-Src and stimulated with VEGF, and αvβ3 activation was assessed by WOW-1 binding as described in methods. As anticipated, VEGF induced 6-fold increase in WOW-1 binding (FIG. 21E). Dominant negative c-Src reduced αvβ3 integrin activation triggered by VEGF by at least 2 fold. In contrast, catalytically active form of c-Src promoted WOW-1 binding to unstimulated as well as to VEGF-stimulated cells. At the same time, wild type Src did not substantially affect WOW-1 binding (FIG. 21E). Similar results were observed using fibrinogen as a soluble ligand for αvβ3 integrin (FIG. 21F). Together, these results show that VEGF induced integrin activation as well as ligand binding is a c-Src dependent process. Next, the role of c-Src in αvβ3 integrin activation and ligand binding was assessed using Src++, SYF and SYF+Src cells. In Src++ and SYF+Src but not in SYF cells, VEGF stimulation resulted in a dramatic increase in integrin activation measured by WOW-1 binding (FIG. 21G). At the same time, no differences in expression levels of β3 integrin were found between these three cell lines (FIG. 21H). Experiments with soluble fibrinogen yielded data similar to that obtained using WOW-1 as a marker of integrin activation (FIG. 21 I). Thus, c-Src and c Src-dependent β3 integrin cytoplasmic tyrosine motifs phosphorylation is essential for VEGF induced αvβ3 integrin activation as well as ligand binding to activated integrin, which are crucial steps in integrin signaling.

c-Src Required for αvβ3 Integrin Dependent Cellular Adhesion to Distinct Ligand.

To examine the role of c-Src in αvβ3 integrin dependent cell adhesion to ECM ligands, we utilized the Src++, SYF, SYF+Src cell systems in which c-Src expression is tightly regulated. Src++ and SYF+Src cells displayed the highest level of adhesion to vitronectin, which is primarily recognized by αvβ3 integrin. SYF cells shown at least three fold lower adhesion on vitronectin compared to Src++ or SYF+ Src cells (FIGS. 22 A and B). At the same time, no differences in cell adhesion to collagen or laminin were observed. Further, adhesion of HUVECs on vitronectin was assessed upon expression of wild type, dominant negative, catalytically active form of Src or upon treatment with Src specific inhibitor SU6656 (FIG. 22 C). Catalytically active form of Src promoted αvβ3 integrin dependent cell adhesion while dominant negative Src or Src inhibitor caused impairment of cell adhesion to vitronectin. These results indicate that c-Src play very crucial role in αvβ3 dependent cell adhesion to ECM ligands. Our previous results indicated that Src phosphorylates β3 integrin on cytoplasmic tyrosine motifs and this phosphorylation is required for early events of angiogenesis such as phosphorylation of VEGFR-2 and interaction between VEGFR-2 and β3 integrin upon VEGF stimulation. To evaluate the role of β3 integrin cytoplasmic tyrosine motifs in cellular adhesion to αvβ3 integrin specific ligand, wild type and DiYF (where β3 integrin cytoplasmic tyrosine motifs were substituted to phenylalanines) mouse lung microvascular endothelial cells were suspended on vitronectin or bone sialoprotein (αvβ3 integrin specific ligands). DiYF endothelial cells shown significant impairment in adhesion on both vitronectin as well as bone sialoprotein (FIG. 22 D). No significance differences in adhesion were found between wild type and DiYF endothelial cells suspended on BSA coated plates. These results clearly indicated that β3 integrin cytoplasmic tyrosine motifs and c-Src mediated phosphorylation of these tyrosine residues are crucial for αvβ3 integrin dependent cellular adhesion to distinct extracellular matrix ligands.

c-Src Dependent Phosphorylation of β3 Integrin Cytoplasmic Tyrosine Motifs are Required for αvβ3 Integrin Dependent Directional Migration of Endothelial Cells.

EC motility is the defining feature of angiogenesis required for the organization of proliferating EC into vessel like structures. This process requires tight regulation of interactions between cells and surrounding ECM. To assess the role of Src-mediated β3 integrin tyrosine phosphorylation in αvβ3 integrin dependent EC migration, HUVECs transfected with various forms of Src were evaluated in migration assays using VEGF as an agonist and vitronectin as a substrate. Dominant negative Src (DN-Src) significantly reduced EC migration in response to VEGF. The constitutively active form of Src (CA-Src) dramatically increased both basal as well as VEGF induced EC migration. Pharmacological inhibitors of c-Src (SU6656) and VEGFR-2 (SU1498), which inhibit β3 integrin tyrosine phosphorylation, also reduced EC migration triggered by VEGF (FIG. 23A). To further evaluate the c-Src mediated β3 integrin cytoplasmic tyrosine motifs phosphorylation in αvβ3 integrin dependent endothelial cell migration, wild type and DiYF mouse lung microvascular endothelial cells were transfected with wild type, dominant negative and catalytically active form of c-Src and stimulated with VEGF (FIG. 23 B). VEGF stimulation induced 2.5 fold increase in WT-Src transfected and 3.5 fold increase in CA- Src transfected wild type endothelial cell migration. DN-Src significantly impaired VEGF induced endothelial cell migration only in wild type endothelial cells. Surprisingly c-Src activity modification did not show any significant difference in migration of DiYF endothelial cells. These results clearly indicated that c-Src mediate signaling through tyrosine phosphorylation of β3 integrin. Lack of these tyrosine residues in cytoplasmic domain of β3 integrin severely impaired c-Src mediated αvβ3 integrin dependent endothelial cell migration.

To examine the role of β3 integrin cytoplasmic tyrosine motifs in directional migration of endothelial cells, wild type and DiYF EC were plated on collagen, laminin or vitronectin coated plates. Wounds were created and VEGF-A165 stimulated cell migration was monitored by time-lapse video microscopy. Cell paths were recorded and presented in FIG. 23C using the same point as an origin of cell migration. Wild type and DiYF endothelial cells plated on laminin exhibited similar speed of migration, 53±4.8 μm/hour and 47±4.2 μm/hour, respectively. On collagen, wild type and DiYF EC also shown similar migration rate of 43±3.5 μm/hour and 44±3.3 μm/hour, respectively. On vitronectin, wild type and DiYF EC showed relatively slow but similar migration at 30±3.2 μm/hour and 28±2.7 μm/hour, respectively. However, when random movement of cells was distinguished from directed migration, the results became quite different. Despite the high speed of migration, the average distance of directed migration from site of origin was quite low for wild type cells on laminin and collagen, 71±6.2 and 92±7.2 μm respectively (FIG. 23C). No differences between wild type and DiYF cells were found. In contrast, wild type endothelial cells showed maximum directed migration when plated on vitronectin (229±6.6 μm). Importantly, directed migration in DiYF cells were dramatically impaired (77±5.4 μm vs 229±6.6 μm for wild type). Wild type EC plated on αvβ3 integrin ligand vitronectin following induction with VEGF-A165 resulted in higher directional persistence of cell migration. Even though VEGF induced the migration rates in the cells plated on laminin and collagen, but VEGF effects were only evident in the wild type cells plated on vitronectin. Simultaneously DiYF endothelial cells plated on vitronectin and induced with VEGF shown very random movement with no distinct pattern. These results clearly demonstrated that β3 integrin cytoplasmic tyrosine motifs are required for persistent and directional migration of EC during processes of angiogenesis.

β3 Integrin Cytoplasmic Tyrosine Phosphorylation is Crucial for Angiogenesis In Vitro and In Vivo To further evaluate the functional significance of c-Src dependent β3 integrin cytoplasmic tyrosine motifs phosphorylation on ability of endothelial cells to organize into precapillary tubes like structure were tested. Accordingly, wild type and DiYF mouse microvascular EC were transfected with various activation form of Src. These cells seeded on Matrigel coated plates and allowed to organize in to precapillary tube like structures. Non-transfected cells induced with induced with VEGF significantly enhanced cumulative tube length only in wild type cells (FIGS. 24 A and B). Over expression of dominant negative Src significantly reduced and constitutively active form of Src dramatically enhanced VEGF induced tube formation on Matrigel only in wild type cells. Either VEGF or various form of Src fails to modify degree of tube formation in DiYF endothelial cells. From all these results we concluded that c-Src dependent β3 integrin cytoplasmic tyrosine motifs phosphorylation is essential for αvβ3 integrin dependent endothelial cell migration as well as precapillary endothelial tube formation on extracellular matrix substrates.

To further examine the role of β3 integrin cytoplasmic tyrosine motif in processes of angiogenesis, wild type and DiYF mice were subcutaneously implanted with hollow fiber containing B16F10 mouse melanoma tumor cells. Growth factor secreted by tumor cells rapidly induced neovascularization only in wild type mice around the hollow fibers. No such dramatic increase in neovascularization found in DiYF mice (FIGS. 24 C and D). Analysis of blood vessel length also indicated significantly higher degree of neovascularization in wild type mice compared to DiYF (80 mm vs 25 mm). Thus, β3 integrin cytoplasmic tyrosine motifs are crucial for initiation of angiogenic program in endothelial cells and ultimately regulate the processes of angiogenesis.

Discussion

This study was focused on the mechanisms and molecular requirements for the cross-talk and cross-activation between two families of cell surface receptors on endothelium: integrins, receptors for extracellular matrix, and tyrosine kinase receptors, represented by VEGFR 2, a receptor for VEGF. The major findings of this manuscript were the following: 1) There was an intimate and coordinated relationship between VEGFR 2 and αvβ3 integrin; VEGFR 2 activation by VEGF induces β3 integrin tyrosine phosphorylation and αvβ3 ligation promoted VEGFR 2 phosphorylation; 2) β3 integrin tyrosine phosphorylation was crucial for VEGF induced tyrosine phosphorylation of VEGFR-2; 3) VEGF induced interaction of c-Src with β3 integrin; 4) Adhesion- and growth factor induced β3 integrin tyrosine phosphorylation is directly mediated by c-Src, which is able to phosphorylate the cytoplasmic domain of β3 in purified as well as in cellular systems; 5) c-Src activation and subsequent β3 integrin tyrosine phosphorylation were critical for interaction between VEGFR-2 and β3 integrin; 6) c-Src mediated growth factor-induced β3 integrin activation, ligand binding and αvβ3 integrin dependent cell adhesion; 7) β3 integrin cytoplasmic tyrosine motif phosphorylation by c-Src was required for directional migration of endothelial cells, tube formation and in vivo angiogenesis.

There are several studies indicating the possibility of functional interaction between integrins and tyrosine kinase receptors in different cell systems. Endothelial cells plated on αvβ3 ligand, vitronectin exhibit greater phosphorylation of VEGFR-2 resulting in increased proliferation and migration of endothelial cells in response to VEGF. Likewise, the treatment of endothelial cells with blocking antibodies against β3 integrin significantly reduced VEGFR-2 phosphorylation induced by VEGF, suggesting β3 integrin involved in VEGFR-2 activation. In epithelial cells, the blockade of αvβ3 integrin significantly inhibited EGF-induced EGF receptor phosphorylation and cell proliferation. Thus, αvβ3 integrin engagement by extracellular matrix proteins seems to be involved in the coordinated activation of tyrosine kinase receptors. Using DiYF knockin endothelial cells we have established that β3 integrin cytoplasmic tyrosine motifs are crucial for integrin-dependent augmentation of VEGF signaling.

We demonstrated that VEGF induces an association of its receptor VEGFR-2 with β3 subunit of αvβ3 integrin, but not with β1 or β5 integrins on endothelial cells. Blocking antibodies against either αv or β3 subunit independently blocked VEGF-induced phosphorylation of β3 integrin cytoplasmic tyrosine motifs and VEGF-induced VEGFR-2 phosphorylation. Thus, one might expect that integrin antagonists would affect not only integrin dependent signaling pathways but would also diminish intracellular responses to VEGF. We found that phosphorylation of both receptors occurred in an inter-dependent manner where phosphorylation of one component of the complex was necessary for complete activation of its partner molecule. Phosphorylation of tyrosine motifs within β3 integrin cytoplasmic domain occurred in response to VEGF and, in turn, was essential for VEGFR-2-β3 integrin association and VEGFR-2 activation and subsequent signaling. Thus, cross talk between the two receptors determines the cellular responses to VEGF as well as to integrin ligation, which, in turn, was regulated at the level of tyrosine phosphorylation events.

Our study explains observations regarding the role of Src in integrin and growth factor signaling in endothelial cells. We have identified c-Src as a molecule that directly phosphorylates the cytoplasmic tyrosine motifs of β3 integrin in response to VEGF stimulation. Further, c-Src is able to directly control VEGF-induced and integrin-mediated cellular responses such as cell adhesion and migration. Src, Yes and Fyn triple mutant cells (SYF) exhibited severely impaired β3 integrin tyrosine phosphorylation in response to growth factors and this was corrected by re-expression of c-Src alone. It is possible that in other cell types such as platelets or osteoclasts, the function of β3 phosphorylation might be performed by another member of Src family kinase (SFK) family due to the extensive functional redundancy among these kinases. In endothelial cells Src, but not Yes or Fyn, was able to interact with VEGFR-2 and β3 integrin in VEGF-dependent manner. Src appears to regulate the complex formation between integrin and VEGFR2, since expression of catalytically active Src stimulated and dominant negative Src and Src inhibitor reduced interaction between VEGFR-2 and β3 integrin in endothelial cells. Importantly, Src dependent β3 integrin cytoplasmic tyrosine motif phosphorylation is a key step in a receptors crosstalk, since phosphorylation deficient mutant of β3 (DiYF) did not form a complex with VEGFR-2 despite expression of constitutively active Src. As a consequence, Src might mediate a wide spectrum of growth factor-induced responses. Recent observations demonstrated that Src is required for VEGF-induced vascular permeability, a response triggered by VEGFR-2 activation. Moreover, v-src is able to modulate blood vessel development in several experimental animal models appears to be crucial for endothelial cell adhesion, motility as well as cellular response to shear stress.

Here we have for the first time demonstrated that growth factor-stimulated ligand binding to αvβ3 integrin on endothelial cells is c-Src dependent. In triple knockout cells (SYF), the lack of Src activity resulted in deficient β3 integrin phosphorylation, which, in turn, led to severe impairment in growth factor induced ligand binding. The latter event is a prerequisite for growth factor-modulated cell adhesion, spreading and migration. Consistent with this, over expression of catalytically active Src enhanced and dominant negative Src and Src inhibitor reduced αvβ3 integrin dependent endothelial cell adhesion. Thus, we concluded that Src is crucial for integrin activation in response to growth factors and also demonstrating intimate association of Src and integrin signaling. In fact, several features of the Src knockout phenotype, including osteopetrosis, show close resemblance to the phenotype of β3 null mice.

The presence of the β3/Src complex at the leading edges of adherent cells further demonstrates their intimate association in basic cellular processes. Further SFKs also involved in integrin signaling, are localized at podosomes, cytoskeletal structures located basally that are distinct from focal adhesion points. Mouse embryonic fibroblasts containing c-Src (Src++ and SYF+Src) shown greater tendency to adhere to vitronectin coated surface than collagen- or laminin-coated surface. These results further strengthen our conclusion that c-Src is required mainly for vitronectin receptor signaling (αvβ3) rather than collagen or laminin receptor signaling. Previous studies have demonstrated that SYF triple knockout cells are defective in migration and have impaired response to gradients of ECM proteins is due to the abnormalities of signaling pathway down stream of integrins. Our data clearly indicated that phosphorylation of β3 integrin cytoplasmic tyrosine motif by c-Src controls growth factor induced, integrin-mediated directional migration of endothelial cells. Interestingly, only Src, but not Fyn, knockout mice display impairment of VEGF induced vascular responses and tumor burden, indicating that Src is a main SFK's in regulation of endothelial cell functions. Our study also demonstrated that over expression of catalytically active form of Src potentates VEGF-induced tube formation, which is abolished by dominant negative Src and c-Src specific pharmacological inhibitors. Further, in vivo model of angiogenesis assay demonstrated the crucial role for c-Src dependent β3 integrin cytoplasmic tyrosine motifs phosphorylation in pathological angiogenesis. Thus, c-Src via direct phosphorylation of αvβ3 integrin cytoplasmic motif controls the functional association between αvβ3 and VEGFR2, which, in turn, regulates activation of both receptors on endothelial cells. This functional interplay is crucial for EC adhesion, migration and angiogenesis in vivo.

Methods

Reagents and Plasmids

Rabbit polyclonal anti-VEGFR-2, anti-β3-integrin, anti-β5-integrin, anti-β1-integrin, anti-Src, anti-Fyn, anti-Yes, and mouse monoclonal anti-phospho-tyrosine (PY20 and PY99) antibodies were purchased from Santa Cruz Biotechnology, Inc. (Santa Cruz, Calif.). Anti-phospho-Src (Tyr-416), anti-phospho-VEGFR-2, and purified, recombinant Src were from Cell Signaling Technology (Beverly, Mass.). Rabbit polyclonal anti-phospho-β3-integrin antibodies (Tyr 747 and Tyr 759) were from Biosource International, Inc. (Camarillo, Calif.). Mouse monoclonal anti-β3 integrin, anti-β5-integrin, anti-β1-integrin, anti-αv integrin blocking antibodies were from Chemicon International, Inc. (Temecula, Calif.). Purified collagen, laminin, vitronectin, bFGF, and VEGF were purchased from R&D Systems (Minneapolis, Minn.). Matrigel was obtained from BD Biosciences (San Jose, Calif.). Protein G agarose, Alexa-488 labeled fibrinogen, and [γ$^{32}$P] ATP were from Invitrogen (Carlsbad, Calif.). ProFound Co-Immunoprecipitation Kit was purchased from Pierce Biotechnology, Inc. (Rockford, Ill.). Wild type, dominant negative, and catalytically active forms of Src cDNA cloned in pUSEamp vector were obtained from Upstate Cell Signaling Solutions (Charlottesville, Va.). SU6656, SU1498, and recombinant protein tyrosine phosphatase were obtained from Calbiochem (San Diego, Calif.). Nucleofector transfection kits for primary endothelial cells were obtained from Amaxa Biosystems (Cologne, Germany). Boyden type cell migration chambers were obtained from Corning (Corning, N.Y.). All other chemicals were analytical grade.

Cell Culture and Transfection

Human umbilical cord vain endothelial cells (HUVEC) cells were grown in DMEM medium supplemented with supplemented with 10% FBS, 90 µg/mL heparin sulphate, 90 µg/mL endothelial cell growth factor, 10,000 U/mL penicillin, 10 µg/mL streptomycin. Cells were used between second and fifth passages. HUVECs were transiently transfected using the HUVEC Nucleofector kit according to manufacturer instructions. Forty-eight hours after transfection, cells were serum starved and used for experiments.

Src$^{++}$, SYF, and SYF+c-Src cells were obtained from American Type Culture Collection. Cells were maintained in Dulbecco-modified eagle medium (DMEM) supplemented with 10% fetal bovine serum (FBS), L-glutamine, and antibiotics and were grown at 37° C. in 6% CO2.

Isolation of Primary Mouse Endothelial Cells and Hollow Fiber Angiogenesis Assay DiYF mice were generated in the laboratory of Dr. David R. Phillips and maintained on a C57/Bl6 background (seven generations of backcrossing). Six- to eight-week old wild-type (WT) and DiYF mice were used in this study. We performed all procedures according to protocols approved by Cleveland Clinic Foundation Institutional Animal Care and Use Committee. WT and DiYF mouse lungs were removed by surgical procedure minced and digested using collagenase-dispase reagent (3 mg/mL). Digests were strained and the resulting cell suspension was plated on flasks coated with 5 μg/mL fibronectin. The hollow fiber angiogenesis assay was performed as described previously using B16F10 mouse melanoma cells. After 12 days mice were anesthetized and sites of fiber implantation were photographed and cumulative vessel lengths were calculated.

Cell Adhesion Assay

HUVECs or mouse embryonic fibroblasts (SYF and SYF+ Src) or mouse lung endothelial cells were detached from the tissue culture flasks using 20 mM EDTA. Cells were washed twice with sterile PBS and re-suspended in DMEM. The cell suspensions were added to ligand-coated wells and placed in humidified incubator for 45 min. Wells were gently washed three times with DMEM and photographs were taken. The numbers of attached and spread cells per field were counted.

Cell Migration Assay

Transwell tissue culture inserts were coated with αvβ3 integrin ligand vitronectin for 24 h at 4° C. Endothelial cells were transfected with various forms of c-Src or treated with inhibitors and were trypsinized; then $1 \times 10^5$ cells were added into each well. Cells were allowed to migrate for 12 h and fixed with 70% methanol for 15 min and stained with Giemsa. The non-migrated cells adhered to the top surface were removed and three random 10× fields were photographed using an inverted phase contrast microscopy.

Time-Lapse Video Microscopy

Endothelial cell motility on various extracellular matrix protein-coated plates induced with VEGF-A165 was analyzed by time-lapse videomicroscopy. Time-lapse imaging was performed using a Leica DM IRB microscope supported by the Metamorph program (Molecular Devices). Images were acquired every 10 min for 10 hr using a Photometric Cool Snap Camera (Roper Scientific) under 5% CO2 and at 37° C. in a stage incubator. Cell paths were generated from centroid positions and migration parameters were computed with ImagePro plus software.

In Vitro Kinase Assay

Purified β3 integrin cytoplasmic peptides specific for tyrosine-747 (DTANNPLYpKEATSTFT-COOH) (SEQ ID NO: 1), tyrosine-759 (KEATSTFTNITYpRGT-COOH) (SEQ ID NO: 15), and control peptides ((DTANNPLF KEATSTFT-COOH (SEQ ID NO: 16) and KEATSTFTNIT FRGT-COOH (SEQ ID NO: 17)) were mixed with c-Src immunoprecipitates or purified full-length c-Src and kinase assay buffer containing 5 μCi of [γ-$^{32}$P]ATP and 10 μm ATP and incubated at 30° C. for 30 min with or without SU6656 and recombinant protein tyrosine phosphatase (PTP). Fractions of reaction mixtures were transferred to phosphocellulose paper and washed with 150 mm of H3PO4. These membranes were rinsed briefly in ethanol, air dried, and transferred to scintillation vials. γ-ATP incorporation was counted using a Beckman LS600IC liquid scintillation counter (Beckman, Fullerton, Calif.).

Fibrinogen and WOW-1 Binding Assay

To assess fibrinogen binding, semiconfluent HUVECs were transfected with various forms of c-Src. Cells were serum starved for 4 h and further induced with 20 ng/mL bFGF or VEGF-A165. Fluorescein isothiocyanate (FITC)-labeled fibrinogen was added at a final concentration of 200 nM and cell were incubated for 30 min. Cells were fixed with 3.7% formaldehyde/PBS for 15 min and washed twice with ice-cold PBS. Fluorescence-activated cell sorting (FACS) was performed using a FACS Calibur (Becton Dickinson, San Jose, Calif.) and data were analyzed using CellQuest software program.

Semiconfluent HUVECs were transfected with various forms of c-Src or Src++. SYF, SYF+Src cells were serum starved for 4 h and further stimulated with 20 ng/mL VEGF-A165 or b-FGF. WOW-1 Fab was added at a final concentration of 30 μg/mL, followed by addition of FITC-conjugated goat anti-mouse IgG at 10 μg/mL. After 30 min cells were fixed with 3.7% formaldehyde/PBS for 15 min, washed twice with PBS, and FACS analysis was performed as described above.

Tube Formation Assay

The formation of vascular tube-like structures by endothelial cells was assessed on a basement membrane matrix preparation. Twelve-well plates were coated with 0.5 mL of Matrigel according to the manufacturer's instructions. Wild-type and DiYF mouse lung endothelial cells were transfected with various forms of c-Src and detached from the tissue culture flasks using 20 mM EDTA. Cells were washed twice with sterile PBS and seeded on Matrigel-coated plates. Medium with or without 20 ng/mL VEGF was added and cells were further incubated at 37° C. for 8 h. The tube formation was observed using an inverted phase contrast microscope (Leica, Wetzlar, Germany) and photographs were taken. Using ImagePro software, the degree of tube formation was quantified by measuring the length of tubes in three random fields.

Immunoprecipitation and Immunoblotting

Cells were lysed in immunoprecipitation lysis buffer (1% Noniodet P-40, 150 mM NaCl, 50 mM Tris-HCL (pH 7.8), 2 mM EDTA, 10 mM NaF, 10 mM Na2P2O7, 2 mM Na3VO4 10 μg/mL leupeptin, 4 μg/mL pepstatin and 0.1 U/mL aprotinin). Cell lysates were centrifuged at 13,000×g for 10 min at 40° C. Supernatants were collected and assayed for protein concentration using the Bio-Rad protein assay method. Cell lysates containing 700-800 μg of total protein were precleared and were immunoprecipitated with the indicated antibody. Immunocomplexes were denatured using Laemmli sample buffer and proteins were separated by sodium dodecylsulphate polyacrylamide gel electrophoresis (SDS-PAGE) and probed with indicated antibody. When appropriate, nitrocellulose membranes were stripped and blotted according to manufacturer's instructions. Endothelial cell surface biotinylation and Western blot analysis were performed. Co-immunoprecipitation of Src family tyrosine kinases with VEGF receptor-2 and β3-integrin were performed with ProFound Co-Immunoprecipitation Kit according to manufacturer's instructions. Bands were analyzed by densitomeric analysis using Kodak 1D software and fold changes were indicated.

Statistical Analysis

Values were expressed as mean plus or minus standard deviations (SD). P values were based on the paired t-test. All the experiments were repeated at least three times unless indicated otherwise. Results were considered statically significant with P value less than 0.05.

It will be appreciated that all patents and publications disclosed in this application are incorporated by reference in their entirety.

Having described the invention, the following is claimed:

1. A method of inhibiting complexing of αvβ3 integrin and VEGFR2 in a cell population, the method comprising contacting the cell population including cells that express $\alpha_v\beta_3$ integrin and VEGFR2 with a therapeutically effective amount of a peptide that inhibits complexing $\alpha_v\beta_3$ integrin and VEGFR2, wherein the peptide consisting of the amino acid sequence selected from the group consisting of SEQ ID NO: 1, SEQ ID NO: 2, SEQ ID NO: 4, and SEQ ID NO: 5.

2. The method of claim 1, wherein the peptide inhibiting tyrosine phosphorylation of at least one of the expressed $\alpha_v\beta_3$ integrin and VEGFR2.

3. The method of claim 1, wherein the peptide does not inhibiting natural ligand binding to the $\alpha_v\beta_3$ integrin.

4. The method of claim 1, wherein the peptide inhibiting tyrosine phosphorylation of the $\alpha_v\beta_3$ integrin.

5. The method of claim 1, wherein the peptide inhibiting tyrosine phosphorylation of VEGFR2 upon VEGF stimulation.

6. The method of claim 1, wherein the peptide competing with $\alpha_v\beta_3$ integrin for interaction with VEGFR2.

7. The method of claim 1, wherein the peptide comprising a phosphorylated tyrosine residue and the peptide corresponding to a portion of the cytoplasmic domain of at least one of $\alpha_v\beta_3$ integrin.

8. The method of claim 7, wherein the peptide containing a tyrosine residue, which is capable of being phosphorylated upon complex formation of the $\alpha_v\beta_3$ integrin and VEGFR2.

9. The method of claim 1, wherein the cells comprising at least one of tumor cells or endothelial cells.

10. A method of treating aberrant angiogenesis in a tissue, the method comprising administering to the tissue a therapeutically effective amount of a peptide that inhibits complex formation of $\alpha_v\beta_3$ integrin and VEGFR2, wherein the peptide consisting of the amino acid sequence selected from the group consisting of SEQ ID NO: 1, SEQ ID NO: 2, SEQ ID NO: 4, and SEQ ID NO: 5.

11. The method of claim 10, wherein the peptide does not inhibiting natural ligand binding to the $\alpha_v\beta_3$ integrin.

12. The method of claim 10, wherein the peptide inhibiting phosphorylation of the $\alpha_v\beta_3$ integrin.

13. The method of claim 10, wherein the peptide inhibiting phosphorylation of VEGFR2 upon VEGF stimulation.

14. The method of claim 10, wherein the peptide competing with $\alpha_v\beta_3$ integrin for interaction with VEGFR2.

15. The method of claim 10, wherein the peptide comprising a phosphorylated tyrosine residue and the peptide sequence corresponding to a portion of the cytoplasmic domain of at least one of $\alpha_v\beta_3$ integrin or.

16. The method of claim 15, wherein the peptide containing a tyrosine residue which is capable of being phosphorylated upon complex formation of the $\alpha_v\beta_3$ integrin and VEGFR2.

17. The method of claim 10, wherein the cells comprising at least one of tumor cells or endothelial cells.

18. A method of treating an angiogenic disorder in a subject, comprising:
administering to cells of the subject expressing $\alpha_v\beta_3$ integrin and VEGFR2 a therapeutically effective amount of peptide that inhibits complexing of $\alpha_v\beta_3$ integrin and VEGFR2, wherein the peptide consisting of the amino acid sequence selected from the group consisting of SEQ ID NO: 1, SEQ ID NO: 2, SEQ ID NO: 4, and SEQ ID NO: 5.

19. The method of claim 18, wherein the peptide does not inhibiting natural ligand binding to the $\alpha_v\beta_3$ integrin.

20. The method of claim 18, wherein the peptide inhibiting tyrosine phosphorylation of the $\alpha_v\beta_3$ integrin.

21. The method of claim 18, wherein the peptide inhibiting tyrosine phosphorylation of VEGFR2 upon VEGF stimulation.

22. The method of claim 18, wherein the peptide competing with $\alpha_v\beta_3$ integrin for interaction with VEGFR2.

23. The method of claim 18, wherein the peptide comprising a phosphorylated tyrosine residue and the peptide corresponding to a portion of the cytoplasmic domain of at least one of $\alpha_v\beta_3$ integrin or.

24. The method of claim 18, wherein the peptide containing a tyrosine residue, which is capable of being phosphorylated upon complex formation of the $\alpha_v\beta_3$ integrin and VEGFR2.

25. The method of claim 18, wherein the angiogenic disorder is aberrant tumor growth.

26. The method of claim 18, wherein the angiogenic disorder is age-related macular degeneration.

* * * * *

UNITED STATES PATENT AND TRADEMARK OFFICE
CERTIFICATE OF CORRECTION

PATENT NO.       : 8,080,252 B2
APPLICATION NO.  : 12/357186
DATED            : December 20, 2011
INVENTOR(S)      : Tatiana Byzova et al.

It is certified that error appears in the above-identified patent and that said Letters Patent is hereby corrected as shown below:

Column 72, line 6, after "integrin" delete "or"

Signed and Sealed this
Thirteenth Day of March, 2012

David J. Kappos
*Director of the United States Patent and Trademark Office*